US006632919B1

(12) United States Patent
Nielsen et al.

(10) Patent No.: US 6,632,919 B1
(45) Date of Patent: *Oct. 14, 2003

(54) PEPTIDE NUCLEIC ACID MONOMERS AND OLIGOMERS

(75) Inventors: Peter E. Nielsen, Kokkedal (DK); Gerald Haaima, Toowong (AU); Anne B. Eldrup, Frederiksberg (DK)

(73) Assignee: Peter Nielsen (DK)

(*) Notice: Subject to any disclaimer, the term of this patent is extended or adjusted under 35 U.S.C. 154(b) by 0 days.

This patent is subject to a terminal disclaimer.

(21) Appl. No.: 09/083,235

(22) Filed: May 22, 1998

Related U.S. Application Data

(63) Continuation-in-part of application No. 08/862,629, filed on May 23, 1997.

(51) Int. Cl.$^7$ .................................................. C07K 2/00
(52) U.S. Cl. ......................... 530/300; 435/6; 536/23.1; 536/24.3; 536/24.31; 536/24.32; 514/45; 514/49; 530/332; 530/323
(58) Field of Search ............................ 435/6; 536/24.3, 536/24.31, 24.32, 23.1; 514/45, 49; 530/332, 300, 323

(56) References Cited

U.S. PATENT DOCUMENTS

| | | | |
|---|---|---|---|
| 3,687,808 A | | 8/1972 | Merigan, Jr. et al. ...... 435/91.3 |
| 5,502,177 A | | 3/1996 | Matteucci et al. ......... 536/26.6 |
| 5,539,082 A | * | 7/1996 | Nielsen ....................... 530/300 |
| 5,539,083 A | | 7/1996 | Cook et al. .................. 530/333 |
| 5,786,461 A | * | 7/1998 | Buchardt .................... 536/18.7 |

FOREIGN PATENT DOCUMENTS

| WO | WO 92/20702 | 11/1992 |
|---|---|---|
| WO | WO 92/20703 | 11/1992 |
| WO | WO 93/12129 | 6/1993 |

(List continued on next page.)

OTHER PUBLICATIONS

Luyten, Eur. J. Med. Chem. 33, 515–576, 1998.*
Ferrer, Bioorg. Med. Chem. 8, 291, 2000.*
Srinivasan, J Am Chem Soc 120, 492, 1998.*
Wittung, J. Am. Chem. Soc. 119, 3189, 1997.*
Best et al., "Energetics of Formation of Sixteen Triple Helical Complexes Which Vary at a Single Position within a Pyrimidine Motif", *J. Am. Chem. Soc.*, 1995, 117(4), 1187–1193.
Crooke and Lebleu (eds.), *Antisense Research and Application*, CRC Press, 1993, Chapter 15, 274–288.
Egholm et al., "PNA hybridizes to complementary oligonucleotides obeying the Watson–Crick hydrogen–bonding rules", *Nature*, 1993, 365, 566–568.
Egholm et al., "Peptide Nucleic Acids (PNA). Oligonucleotide Analogues with an Achiral Peptide Backbone", *J. Am. Chem. Soc.*, 1992, 114, 1895–1897.

Egholm et al., "Recognition of Guanine and Adenine in DNA by Cytosine and Thymine Containing Peptide Nucleic Acids (PNA)", *J. Am. Chem. Soc.*, 1992, 114, 9677–9678.
Greenberg et al., "Energetics of Formation of Sixteen Triple Helical Complexes Which Vary at a Single Position within a Purine Motif", *J. Am. Chem. Soc.*, 1995, 117, 5016–5022.
Hyrup et al., "Peptide Nucleic Acids (PNA): Synthesis, Properties and Potential Applications", *Bioorganic Med. Chem.*, 1996, 4(1), 5–23.
Knudsen et al., "Antisense properties of duplex– and triplex–forming PNAs", *Nucl. Acids Res.*, 1996, 24(3), 494–500.
Lin et al., "Tricyclic 2'–Deoxycytidine Analogs: Synthesis and Incorporation into Oligodeoxynucleotides Which Have Enhanced Binding to Complementary RNA", *J. Am. Chem.*, 1995, 117, 3873–3874.
Lehninger, "The amino acid building blocks of proteins", *Biochemistry*, Second Edition, Worth Publishers, Inc., 1975, Ch. 4, 73–77.
Matteucci et al., "Hybridization Properties of Oligonucleotides Bearing a Tricyclic 2'–Deoxycytidine Analog Based on a Carbazole Ring System", *Tetra. Lett.*, 1996, 37(29), 5057–5060.
Moser et al., "Sequence–Specific Cleavage of Double Helical DNA by Triple Helix Formation", *Science*, 1987, 238, 645–650.
Nielsen et al., "Strand Displacement Binding of a Duplex–Forming Homopurine PNA to a Homopyrimidine Duplex DNA Target", *J. Am. Chem. Soc.*, 1996, 118, 2287–2288.
Nielsen et al., "Sequence–Selective Recognition of DNA by Strand Displacement with a Thymine–Substituted Polyamide", *Science*, 1991, 254, 1497–1500.
Nielsen, "Peptide nucleic acid (PNA): A lead for gene therapeutic drugs", Trainor (ed.), *Perspectives Drug Disc. Des.*, 1996, 4, 76–84.
Patel, "Marriage of convenience", *Nature*, 1993, 364, 490–492.
Shanmugam, "Another Approach to the Synthesis of Furo(2, 3–b) quinolines", *Naturforsh*, 1973, 196, 551–553.
Uhlmann et al., "Antisense Oligonucleotides: A New Therapeutic Principle", *Chem. Rev.*, 1990, 90(4), 544–584.
Dueholm, K.L. et al., "An Efficient Synthesis of BOC–Aminoacetaldehyde and its Application to the Synthesis of N–(2–BOC–Aminoethyl)Glycine Esters", *Organic Prep. & Proc.*, 1993, 25, 457–461.
Turner, J.A., "A General Approach to the Synthesis of 1,6–, 1–7–, and 1,8–Naphthyridines", *J. Org. Chem.*, 1990, 55, 4744–4750.

*Primary Examiner*—Christopher S. F. Low
*Assistant Examiner*—David Lukton
(74) *Attorney, Agent, or Firm*—Woodcock Washburn LLP

(57) ABSTRACT

Novel peptide nucleic acid (PNA) oligomers and their constituent monomers are disclosed. The PNA oligomers and linked PNAs form triple stranded structures with nucleic acids that show an increased specificity for thymidine in nucleic acid targets relative to naturally occurring nucleobases.

42 Claims, No Drawings

FOREIGN PATENT DOCUMENTS

| WO | WO 93/25706 | 12/1993 |
| WO | WO 94/28171 | 12/1994 |
| WO | WO 95/14708 | 6/1995 |
| WO | WO 95/14789 | 6/1995 |
| WO | WO 95/15974 | 6/1995 |
| WO | WO 95/16202 | 6/1995 |
| WO | WO 96/025588 | 2/1996 |

* cited by examiner

SEQUENCE LISTING

<160> NUMBER OF SEQ ID NOS: 87

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence: Novel

```
                                         Sequence

<400> SEQUENCE: 1
cgcagatagt aaacgc                                                     16

<210> SEQ ID NO 2
<211> LENGTH: 13
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (10)..(11)
<223> OTHER INFORMATION: Bases 10 and 11 are linked via three
      consecutive 8-amino-3, 6-dioxaoctanoic acid groups (egl)

<400> SEQUENCE: 2
tctatcattt ttt                                                        13

<210> SEQ ID NO 3
<211> LENGTH: 13
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (10)..(11)
<223> OTHER INFORMATION: Bases 10 and 11 are linked via three
      consecutive 8-amino-3, 6-dioxaoctanoic acid groups (egl)

<400> SEQUENCE: 3
tctatcattt ttt                                                        13

<210> SEQ ID NO 4
<211> LENGTH: 13
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (10)..(11)
<223> OTHER INFORMATION: Bases 10 and 11 are linked via three
      consecutive 8-amino-3, 6-dioxaoctanoic acid groups (egl)

<400> SEQUENCE: 4
tctatcattt ttt                                                        13

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 5
cgcagacagc aaacgc                                                     16

<210> SEQ ID NO 6
<211> LENGTH: 13
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
```

```
<222> LOCATION: (10)..(11)
<223> OTHER INFORMATION: Bases 10 and 11 are linked via three
      consecutive 8-amino-3, 6-dioxaoctanoic acid groups (egl)

<400> SEQUENCE: 6
tctgtcgttt ttt                                                    13

<210> SEQ ID NO 7
<211> LENGTH: 13
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (10)..(11)
<223> OTHER INFORMATION: Bases 10 and 11 are linked via three
      consecutive 8-amino-3, 6-dioxaoctanoic acid groups (egl)

<400> SEQUENCE: 7
tctgtcgttt ttt                                                    13

<210> SEQ ID NO 8
<211> LENGTH: 13
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (10)..(11)
<223> OTHER INFORMATION: Bases 10 and 11 are linked via three
      consecutive 8-amino-3, 6-dioxaoctanoic acid groups (egl)

<400> SEQUENCE: 8
tctgtcgttt ttt                                                    13

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 9
cgcagatagt aaacgc                                                 16

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 10
cgcagaaagt aaacgc                                                 16

<210> SEQ ID NO 11
<211> LENGTH: 16
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 11
```

```
cgcagagagt aaacgc                                                    16
```

<210> SEQ ID NO 12
<211> LENGTH: 16
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 12

```
cgcagacagt aaacgc                                                    16
```

<210> SEQ ID NO 13
<211> LENGTH: 16
<212> TYPE: DNA
<213> ORGANISM: Artificial Sequence
<220> FEATURE:
<223> OTHER INFORMATION: Description of Combined DNA/RNA Molecule:
      Oligonucleotide
<223> OTHER INFORMATION: Description of Artificial Sequence: Novel
      Sequence

<400> SEQUENCE: 13

```
cgcagauagu aaacgc                                                    16
```

<210> SEQ ID NO 14
<211> LENGTH: 16
<212> TYPE: DNA
<213> ORGANISM: Artificial Sequence
<220> FEATURE:
<223> OTHER INFORMATION: Description of Combined DNA/RNA Molecule:
      Oligonucleotide
<223> OTHER INFORMATION: Description of Artificial Sequence: Novel
      Sequence

<400> SEQUENCE: 14

```
cgcagaaagu aaacgc                                                    16
```

<210> SEQ ID NO 15
<211> LENGTH: 16
<212> TYPE: DNA
<213> ORGANISM: Artificial Sequence
<220> FEATURE:
<223> OTHER INFORMATION: Description of Combined DNA/RNA Molecule:
      Oligonucleotide
<223> OTHER INFORMATION: Description of Artificial Sequence: Novel
      Sequence

<400> SEQUENCE: 15

```
cgcagagagu aaacgc                                                    16
```

<210> SEQ ID NO 16
<211> LENGTH: 15
<212> TYPE: DNA
<213> ORGANISM: Artificial Sequence
<220> FEATURE:
<223> OTHER INFORMATION: Description of Combined DNA/RNA Molecule:
      Oligonucleotide
<223> OTHER INFORMATION: Description of Artificial Sequence: Novel
      Sequence

<400> SEQUENCE: 16

```
cgcagacagu aaacg                                                     15
```

<210> SEQ ID NO 17
<211> LENGTH: 16
<212> TYPE: DNA

```
<213> ORGANISM: Artificial Sequence
<220> FEATURE:
<223> OTHER INFORMATION: Description of Artificial Sequence: Novel
      Sequence

<400> SEQUENCE: 17
cgcagacagc aaacgc                                                    16

<210> SEQ ID NO 18
<211> LENGTH: 16
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 18
cgcagaaagc aaacgc                                                    16

<210> SEQ ID NO 19
<211> LENGTH: 16
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 19
cgcagagagc aaacgc                                                    16

<210> SEQ ID NO 20
<211> LENGTH: 16
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 20
cgcagatagc aaacgc                                                    16

<210> SEQ ID NO 21
<211> LENGTH: 10
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 21
agtgatctac                                                           10

<210> SEQ ID NO 22
<211> LENGTH: 10
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 22
agtgatctac                                                           10

<210> SEQ ID NO 23
<211> LENGTH: 10
<212> TYPE: DNA
<213> ORGANISM: Artificial Sequence
```

<220> FEATURE:
<223> OTHER INFORMATION: Description of Artificial Sequence: Novel
      Sequence

<400> SEQUENCE: 23
gtagatcact                                                                  10

<210> SEQ ID NO 24
<211> LENGTH: 10
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (6)
<223> OTHER INFORMATION: n is an incorporated N-(benzo [b] [1,8]
      naphthyridin-2-(1H)-on-3-yl) acetyl)-N-(2-Boc-aminoethyl) glycine
      monomer.

<400> SEQUENCE: 24 gtagancact                                                                  10

<210> SEQ ID NO 25
<211> LENGTH: 10
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (2)
<223> OTHER INFORMATION: n is an incorporated N-(benzo [b] [1,8]
      naphthyridin-2-(1H)-on-3-yl) acetyl)-N-(2-Boc-aminoethyl) glycine
      monomer.
<221> NAME/KEY: misc_feature
<222> LOCATION: (6)
<223> OTHER INFORMATION: n is an incorporated N-(benzo [b] [1,8]
      naphthyridin-2-(1H0-on-3-yl) acetyl)-N-(2-Boc-aminoethyl) glycine
      monomer.
<221> NAME/KEY: misc_feature
<222> LOCATION: (10)
<223> OTHER INFORMATION: n is an incorporated N-benzo [b] [1,8]
      naphthyridin-2-(1H)-on-3-yl) acetyl)-N-(2-Boc-aminoethyl) glycine
      monomer.

<400> SEQUENCE: 25 gnagancacn                                                                  10

<210> SEQ ID NO 26
<211> LENGTH: 10
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (6)
<223> OTHER INFORMATION: n is 7-chloro-1, 8-naphthyridin-2(1H)-one

<400> SEQUENCE: 26 gtagancact                                                                  10

<210> SEQ ID NO 27
<211> LENGTH: 10
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature

```
<222> LOCATION: (6)
<223> OTHER INFORMATION: n is 6-chloro-1,8-naphthyridin-2(IH)-one

<400> SEQUENCE: 27 gtagancact                                                          10

<210> SEQ ID NO 28
<211> LENGTH: 10
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (6)
<223> OTHER INFORMATION: 7-methyl-1,8-naphthyridin-2(1H)-one

<400> SEQUENCE: 28 gtagancact                                                          10

<210> SEQ ID NO 29
<211> LENGTH: 10
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (6)
<223> OTHER INFORMATION: n is 6-methyl-1,8-naphthyridin-2(1H)-one

<400> SEQUENCE: 29 gtagancact                                                          10

<210> SEQ ID NO 30
<211> LENGTH: 10
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (6)
<223> OTHER INFORMATION: n is 5-methyl-1,8-naphthyridin-2 (1H)-one

<400> SEQUENCE: 30 gtagancact                                                          10

<210> SEQ ID NO 31
<211> LENGTH: 10
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 31
catcatctac                                                          10

<210> SEQ ID NO 32
<211> LENGTH: 10
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 32
```
catcatctac                                                              10

<210> SEQ ID NO 33
<211> LENGTH: 10
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 33
gtagatgatg                                                              10

<210> SEQ ID NO 34
<211> LENGTH: 10
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (2)
<223> OTHER INFORMATION: n is N-(benzo [b] [1,8]
      naphthyridin-2(1H)-on-3-yl) acetyl)-N-(2-Boc-aminoethyl) glycine
<221> NAME/KEY: misc_feature
<222> LOCATION: (6)
<223> OTHER INFORMATION: n is N-(benzo[b] [1,8]
      naphthyridin-2(1H)-on-3-yl) acetyl)-N-(2-Boc-aminoethyl) glycine
<221> NAME/KEY: misc_feature
<222> LOCATION: (9)
<223> OTHER INFORMATION: n is N-(benzo [b] [1,8]
      naphthyridin-2(1H)-on-3-yl) acetyl)-N-(2-Boc-aminoethyl) glycine

<400> SEQUENCE: 34 gnagangang                                                              10

<210> SEQ ID NO 35
<211> LENGTH: 10
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (2)
<223> OTHER INFORMATION: n is 7-chloro-1,8-naphthyridin-2(1H)-one
<221> NAME/KEY: misc_feature
<222> LOCATION: (6)
<223> OTHER INFORMATION: n is 7-chloro-1,8-naphthyridin-2(1H)-one
<221> NAME/KEY: misc_feature
<222> LOCATION: (9)
<223> OTHER INFORMATION: n is 7-chloro-1,8-naphthyridin-2(1H)-one

<400> SEQUENCE: 35 gnagangang                                                              10

<210> SEQ ID NO 36
<211> LENGTH: 10
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (2)
<223> OTHER INFORMATION: n is 6-chloro-1,8-naphthyridin-2(1H)-one
<221> NAME/KEY: misc_feature
<222> LOCATION: (6)
<223> OTHER INFORMATION: n is 6-chloro-1,8-naphthyridin-2(1H)-one
<221> NAME/KEY: misc_feature
<222> LOCATION: (9)
<223> OTHER INFORMATION: n is 6-chloro-1,8-naphthyridin

```
<400> SEQUENCE: 36 gnagangang                                                           10

<210> SEQ ID NO 37
<211> LENGTH: 10
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (2)
<223> OTHER INFORMATION: 7-methyl-1, 8-naphthyridin-2(1H)-one
<221> NAME/KEY: misc_feature
<222> LOCATION: (6)
<223> OTHER INFORMATION: 7-methyl-1,8-naphthyridin-2(1H)-one
<221> NAME/KEY: misc_feature
<222> LOCATION: (9)
<223> OTHER INFORMATION: 7-methyl-1,8-naphthyridin-2(1H)-one

<400> SEQUENCE: 37 gnagangang                                                           10

<210> SEQ ID NO 38
<211> LENGTH: 10
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (2)
<223> OTHER INFORMATION: n is 6-methyl-1,8-naphthyridin-2(1H)-one
<221> NAME/KEY: misc_feature
<222> LOCATION: (6)
<223> OTHER INFORMATION: n is 6-methyl-1,8-naphthyridin-2(1H)-one
<221> NAME/KEY: misc_feature
<222> LOCATION: (9)
<223> OTHER INFORMATION: n is 6-methyl-1,8-naphthyridin-2(1H)-one

<400> SEQUENCE: 38 gnagangang                                                           10

<210> SEQ ID NO 39
<211> LENGTH: 10
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (2)
<223> OTHER INFORMATION: n is 5-methyl-1,8-naphthyridin-2(1H)-one
<221> NAME/KEY: misc_feature
<222> LOCATION: (6)
<223> OTHER INFORMATION: n is 5-methyl-1,8-naphthyridin-2(1H)-one
<221> NAME/KEY: misc_feature
<222> LOCATION: (9)
<223> OTHER INFORMATION: n is 5-methyl-1,8-naphthyridin-2(1H)-one

<400> SEQUENCE: 39 gnagangang                                                           10

<210> SEQ ID NO 40
<211> LENGTH: 10
<212> TYPE: DNA
<213> ORGANISM: Artificial Sequence
<220> FEATURE:
<223> OTHER INFORMATION: Description of Artificial Sequence: Novel
      Sequence
```

```
<400> SEQUENCE: 40
ctcaaactct                                                              10

<210> SEQ ID NO 41
<211> LENGTH: 10
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 41
ctcaaactct                                                              10

<210> SEQ ID NO 42
<211> LENGTH: 10
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 42
agagtttgag                                                              10

<210> SEQ ID NO 43
<211> LENGTH: 10
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (5)..(7)
<223> OTHER INFORMATION: n is N-(benzo [b] [1,8]
      naphthyridin-2(1H)-on-3-yl) acetyl)-N-(2-Boc-aminoethyl) glycine

<400> SEQUENCE: 43 agagnnngag                                                              10

<210> SEQ ID NO 44
<211> LENGTH: 10
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (5)..(7)
<223> OTHER INFORMATION: n is 7-chloro-1,8-naphthyridin-2(1H)-one

<400> SEQUENCE: 44 agagnnngag                                                              10

<210> SEQ ID NO 45
<211> LENGTH: 10
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (5)..(7)
<223> OTHER INFORMATION: n is 6-chloro-1,8-naphthyridin-2(1H)-one

<400> SEQUENCE: 45 agagnnngag                                                              10
```

<210> SEQ ID NO 46
<211> LENGTH: 10
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (5)..(7)
<223> OTHER INFORMATION: n is 7-methyl-1,8-naphthyridin-2(1H)-one

<400> SEQUENCE: 46 agagnnngag                                                              10

<210> SEQ ID NO 47
<211> LENGTH: 10
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (5)..(7)
<223> OTHER INFORMATION: n is 6-methyl-1,8-naphthyridin-2(1H)-one

<400> SEQUENCE: 47 agagnnngag                                                              10

<210> SEQ ID NO 48
<211> LENGTH: 10
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (5)..(7)
<223> OTHER INFORMATION: n is 5-methy-1,8-naphthyridin-2(1H)-one

<400> SEQUENCE: 48 agagnnngag                                                              10

<210> SEQ ID NO 49
<211> LENGTH: 10
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 49
agtgatctac                                                              10

<210> SEQ ID NO 50
<211> LENGTH: 10
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 50
agtggtctac                                                              10

<210> SEQ ID NO 51
<211> LENGTH: 10
<212> TYPE: DNA

```
<213> ORGANISM: Artificial Sequence
<220> FEATURE:
<223> OTHER INFORMATION: Description of Artificial Sequence: Novel
      Sequence

<400> SEQUENCE: 51
agtgctctac                                                              10

<210> SEQ ID NO 52
<211> LENGTH: 10
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 52
agtgttctac                                                              10

<210> SEQ ID NO 53
<211> LENGTH: 10
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 53
agtgatctac                                                              10

<210> SEQ ID NO 54
<211> LENGTH: 10
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 54
agtggtctac                                                              10

<210> SEQ ID NO 55
<211> LENGTH: 10
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 55
agtgctctac                                                              10

<210> SEQ ID NO 56
<211> LENGTH: 10
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 56
agtgttctac                                                              10

<210> SEQ ID NO 57
<211> LENGTH: 10
<212> TYPE: DNA
<213> ORGANISM: Artificial Sequence
```

```
<220> FEATURE:
<223> OTHER INFORMATION: Description of Artificial Sequence: Novel
      Sequence

<400> SEQUENCE: 57
gtagatcact                                                                10

<210> SEQ ID NO 58
<211> LENGTH: 10
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (6)
<223> OTHER INFORMATION: n is N-(benzo [b] [1,8]
      naphthridin-2(1H)-on-3-yl) acethyl)-N-(2-Boc-aminoethyl) glycine

<400> SEQUENCE: 58 gtagancact                                                                10

<210> SEQ ID NO 59
<211> LENGTH: 10
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (6)
<223> OTHER INFORMATION: n is 7-chloro-1,8-naphthyridin-2(1H)-one

<400> SEQUENCE: 59 gtagancact                                                                10

<210> SEQ ID NO 60
<211> LENGTH: 14
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (3)
<223> OTHER INFORMATION: n is pseudoisocytosine
<221> NAME/KEY: misc_feature
<222> LOCATION: (7)
<223> OTHER INFORMATION: n is pseudoisocytosine
<221> NAME/KEY: misc_feature
<222> LOCATION: (7)..(8)
<223> OTHER INFORMATION: Bases 7 and 8 are linked via three consecutive
      8-amino-3, 6-dioxaoctanoic acid groups (egl)

<400> SEQUENCE: 60
ttntttnctt tctt                                                           14

<210> SEQ ID NO 61
<211> LENGTH: 14
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (2)
<223> OTHER INFORMATION: n is N-(benzo [b] [1,8]
      naphthyridin-2(1H)-on-3-yl) acetyl)-N-(2-Boc-aminoethyl) glycine
<221> NAME/KEY: misc_feature
<222> LOCATION: (3)
<223> OTHER INFORMATION: n is pseudoisocytosine
```

```
<221> NAME/KEY: misc_feature
<222> LOCATION: (4)
<223> OTHER INFORMATION: n is N-(benzo [b] [1,8]
      naphthyridin-2(1H)-on-3-yl) acetyl)-N-(2-Boc-aminoethyl) glycine
<221> NAME/KEY: misc_feature
<222> LOCATION: (6)
<223> OTHER INFORMATION: n is N-(benzo [b] [1,8] naphthyridin-2
      (1H)-on-3-yl) acetyl)-N-(2-Boc-aminoethyl) glycine
<221> NAME/KEY: misc_feature
<222> LOCATION: (7)
<223> OTHER INFORMATION: n is pseudoisocytosine
<221> NAME/KEY: misc_feature
<222> LOCATION: (7)..(8)
<223> OTHER INFORMATION: Bases 7 and 8 are linked via three consecutive
      8-amino-3, 6-dioxactanoic acid groups (egl)

<400> SEQUENCE: 61
tnnntnnctt tctt                                                     14

<210> SEQ ID NO 62
<211> LENGTH: 14
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (2)
<223> OTHER INFORMATION: n is 7-chloro-1,8-naphthyridin-2(1H)-one
<221> NAME/KEY: misc_feature
<222> LOCATION: (3)
<223> OTHER INFORMATION: n is pseudoisocytosine
<221> NAME/KEY: misc_feature
<222> LOCATION: (4)
<223> OTHER INFORMATION: n is 7-chloro-1,8-naphthyridin-2(1H)-one
<221> NAME/KEY: misc_feature
<222> LOCATION: (6)
<223> OTHER INFORMATION: n is 7-chloro-1,8-naphthyridin-2(1H)-one
<221> NAME/KEY: misc_feature
<222> LOCATION: (7)
<223> OTHER INFORMATION: n is pseudoisocytosine
<221> NAME/KEY: misc_feature
<222> LOCATION: (7)..(8)
<223> OTHER INFORMATION: Bases 7 and 8 are linked via three consecutive
      8-amino-3, 6-dioxaoctanoic acid groups (egl)

<400> SEQUENCE: 62
tnnntnnctt tctt                                                     14

<210> SEQ ID NO 63
<211> LENGTH: 14
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (2)
<223> OTHER INFORMATION: n is 6-chloro-1,8-naphthyridin-2(1H)-one
<221> NAME/KEY: misc_feature
<222> LOCATION: (3)
<223> OTHER INFORMATION: n is pseudoisocytosine
<221> NAME/KEY: misc_feature
<222> LOCATION: (4)
<223> OTHER INFORMATION: n is 6-chloro-1,8-naphthyridin-2(1H)-one
<221> NAME/KEY: misc_feature
<222> LOCATION: (6)
<223> OTHER INFORMATION: n is 6-chloro-1,8-naphthyridin-2(1H)-one
<221> NAME/KEY: misc_feature
<222> LOCATION: (7)
<223> OTHER INFORMATION: n is pseudoisocytosine
<221> NAME/KEY: misc_feature
<222> LOCATION: (7)..(8)
<223> OTHER INFORMATION: Bases 7 and 8 are linked via three consecutive
      8-amino-3, 6-dioxaoctanoic acid groups (egl)
```

```
<400> SEQUENCE: 63
tnnntnnctt tctt                                                    14

<210> SEQ ID NO 64
<211> LENGTH: 14
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (2)
<223> OTHER INFORMATION: n is 7-methyl-1,8-naphthyridin-2(1H)-one
<221> NAME/KEY: misc_feature
<222> LOCATION: (3)
<223> OTHER INFORMATION: n is pseudoisocytosine
<221> NAME/KEY: misc_feature
<222> LOCATION: (4)
<223> OTHER INFORMATION: n is 7-methyl-1,8-naphthyridin-2(1H)-one
<221> NAME/KEY: misc_feature
<222> LOCATION: (6)
<223> OTHER INFORMATION: n is 7-methyl-1,8-naphthyridin-2(1H)-one
<221> NAME/KEY: misc_feature
<222> LOCATION: (6)
<223> OTHER INFORMATION: n is 7-methyl-1,8-naphthyridin-2(1H)-one
<221> NAME/KEY: misc_feature
<222> LOCATION: (7)
<223> OTHER INFORMATION: n is pseudoisocytosine
<221> NAME/KEY: misc_feature
<222> LOCATION: (7)..(8)
<223> OTHER INFORMATION: Bases 7 and 8 are linked via three consecutive
      8-amino-3, 6-dioxaoctanoic acid groups (egl)

<400> SEQUENCE: 64
tnnntnnctt tctt                                                    14

<210> SEQ ID NO 65
<211> LENGTH: 14
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (2)
<223> OTHER INFORMATION: n is 6-methyl-1,8-naphthyridin-2(1H)-one
<221> NAME/KEY: misc_feature
<222> LOCATION: (3)
<223> OTHER INFORMATION: n is pseudoisocytosine
<221> NAME/KEY: misc_feature
<222> LOCATION: (4)
<223> OTHER INFORMATION: n is 6-methyl-1,8-naphthyridin-2(1H)-one
<221> NAME/KEY: misc_feature
<222> LOCATION: (6)
<223> OTHER INFORMATION: n is 6-methyl-1,8-naphthyridin-2(1H)-one
<221> NAME/KEY: misc_feature
<222> LOCATION: (7)
<223> OTHER INFORMATION: n is pseudoisocytosine
<221> NAME/KEY: misc_feature
<222> LOCATION: (7)..(8)
<223> OTHER INFORMATION: Bases 7 and 8 are linked via three consecutive
      8-amino-3, 6-dioxaoctanoic acid groups (egl)

<400> SEQUENCE: 65
tnnntnnctt tctt                                                    14

<210> SEQ ID NO 66
<211> LENGTH: 14
<212> TYPE: DNA
<213> ORGANISM: Artificial Sequence
<220> FEATURE:
<223> OTHER INFORMATION: Description of Artificial Sequence: Novel
```

```
      Sequence
<221> NAME/KEY: misc_feature
<222> LOCATION: (2)
<223> OTHER INFORMATION: n is 5-methyl-1,8-naphthyridin-2(1H)-one
<221> NAME/KEY: misc_feature
<222> LOCATION: (3)
<223> OTHER INFORMATION: n is pseudoisocytosine
<221> NAME/KEY: misc_feature
<222> LOCATION: (4)
<223> OTHER INFORMATION: n is 5-methyl-1,8-naphthyridin-2(1H)-one
<221> NAME/KEY: misc_feature
<222> LOCATION: (6)
<223> OTHER INFORMATION: n is 5-methyl-1,8-naphthyridin-2(1H)-one
<221> NAME/KEY: misc_feature
<222> LOCATION: (7)
<223> OTHER INFORMATION: n is pseudoisocytosine
<221> NAME/KEY: misc_feature
<222> LOCATION: (7)..(8)
<223> OTHER INFORMATION: Bases 7 and 8 are linked via three consecutive
      8-amino-3,6-dioxaoctanoic acid groups (elg)

<400> SEQUENCE: 66 tnnntnncttt tctt                                                     14

<210> SEQ ID NO 67
<211> LENGTH: 14
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (2)
<223> OTHER INFORMATION: n is pseudoisocytosine
<221> NAME/KEY: misc_feature
<222> LOCATION: (7)
<223> OTHER INFORMATION: n is pseudoisocytosine
<221> NAME/KEY: misc_feature
<222> LOCATION: (7)..(8)
<223> OTHER INFORMATION: Bases 7 and 8 are linked via three consecutive
      8-amino-3, 6-dioxaoctanoic acid groups (egl)

<400> SEQUENCE: 67 tntttnctt ttct                                                       14

<210> SEQ ID NO 68
<211> LENGTH: 14
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (2)
<223> OTHER INFORMATION: n is pseudoisocytosine
<221> NAME/KEY: misc_feature
<222> LOCATION: (3)..(5)
<223> OTHER INFORMATION: n is N-(benzo [b] [1,8]
      naphthyridin-2(1H)-on-3-yl) acetyl)-N-(2-Boc-aminoethyl) glycine
<221> NAME/KEY: misc_feature
<222> LOCATION: (7)
<223> OTHER INFORMATION: n is pseudoisocytosine
<221> NAME/KEY: misc_feature
<222> LOCATION: (7)..(8)
<223> OTHER INFORMATION: Bases 7 and 8 are linked via three consecutive
      8-amino-3, 6-dioxaoctanoic acid groups (egl)

<400> SEQUENCE: 68 tnnnntncttt ttct                                                     14

<210> SEQ ID NO 69
<211> LENGTH: 14
<212> TYPE: DNA
```

```
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (2)
<223> OTHER INFORMATION: n is pseudoisocytosine
<221> NAME/KEY: misc_feature
<222> LOCATION: (3)..(5)
<223> OTHER INFORMATION: n is 7-chloro-1,8-naphthyridin-2(1H)-one
<221> NAME/KEY: misc_feature
<222> LOCATION: (7)
<223> OTHER INFORMATION: n is pseudoisocytosine
<221> NAME/KEY: misc_feature
<222> LOCATION: (7)..(8)
<223> OTHER INFORMATION: Bases 7 and 8 are linked via three consecutive
      8-amino-3,6-dioxaoctanoic acid groups (egl)

<400> SEQUENCE: 69
tnnnntnctt ttct                                                     14

<210> SEQ ID NO 70
<211> LENGTH: 14
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (2)
<223> OTHER INFORMATION: n is pseudoisocytosine
<221> NAME/KEY: misc_feature
<222> LOCATION: (3)..(5)
<223> OTHER INFORMATION: n is 6-chloro-1,8-naphthyridin-2(1H)-one
<221> NAME/KEY: misc_feature
<222> LOCATION: (7)
<223> OTHER INFORMATION: n is pseudoisocytosine
<221> NAME/KEY: misc_feature
<222> LOCATION: (7)..(8)
<223> OTHER INFORMATION: Bases 7 and 8 are linked via three consecutive
      8-amino-3,6-dioxaoctanoic acid groups (egl)

<400> SEQUENCE: 70
tnnnntnctt ttct                                                     14

<210> SEQ ID NO 71
<211> LENGTH: 14
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (2)
<223> OTHER INFORMATION: n is pseudoisocytosine
<221> NAME/KEY: misc_feature
<222> LOCATION: (3)..(5)
<223> OTHER INFORMATION: n is 7-methyl-1,8-naphthyridin-2(1H)-one
<221> NAME/KEY: misc_feature
<222> LOCATION: (7)
<223> OTHER INFORMATION: n is pseudoisocytosine
<221> NAME/KEY: misc_feature
<222> LOCATION: (7)..(8)
<223> OTHER INFORMATION: Bases 7 and 8 are linked via three consecutive
      8-amino-3,6-dioxaoctanoic acid groups (egl)

<400> SEQUENCE: 71
tnnnntnctt ttct                                                     14

<210> SEQ ID NO 72
<211> LENGTH: 14
<212> TYPE: DNA
<213> ORGANISM: Artificial Sequence
```

```
<220> FEATURE:
<223> OTHER INFORMATION: Description of Artificial Sequence: Novel
      Sequence
<221> NAME/KEY: misc_feature
<222> LOCATION: (2)
<223> OTHER INFORMATION: n is pseudoisocytosine
<221> NAME/KEY: misc_feature
<222> LOCATION: (3)..(5)
<223> OTHER INFORMATION: 6-methyl-1,8-naphthyridin-2(1H)-one
<221> NAME/KEY: misc_feature
<222> LOCATION: (7)
<223> OTHER INFORMATION: n is pseudoisocytosine
<221> NAME/KEY: misc_feature
<222> LOCATION: (7)..(8)
<223> OTHER INFORMATION: Bases 7 and 8 are linked via three consecutive
      8-amino-3,6-dioxaoctanoic acid groups (egl)

<400> SEQUENCE: 72 tnnnntncttt ttct                                                    14

<210> SEQ ID NO 73
<211> LENGTH: 14
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (2)
<223> OTHER INFORMATION: n is pseudoisocytosine
<221> NAME/KEY: misc_feature
<222> LOCATION: (3)..(5)
<223> OTHER INFORMATION: n is 5-methyl-1,8-naphthyridin-2(1H)-one
<221> NAME/KEY: misc_feature
<222> LOCATION: (7)
<223> OTHER INFORMATION: n is pseudoisocytosine
<221> NAME/KEY: misc_feature
<222> LOCATION: (7)..(8)
<223> OTHER INFORMATION: Bases 7 and 8 are linked via three
      consecutive8-amino-3, 6-dioxaoctanoic acid groups
      (egl)

<400> SEQUENCE: 73 tnnnntncttt ttct                                                    14

<210> SEQ ID NO 74
<211> LENGTH: 13
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 74
cgcagagaaa cgc                                                      13

<210> SEQ ID NO 75
<211> LENGTH: 14
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (7)..(8)
<223> OTHER INFORMATION: Bases 7 and 8 are linked via three consecutive
      8-amino-3,6-dioxaoctanoic acid groups (egl)

<400> SEQUENCE: 75 tctcttttttt ctct                                                    14
```

```
<210> SEQ ID NO 76
<211> LENGTH: 14
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (2)
<223> OTHER INFORMATION: n is pseudoisocytosine
<221> NAME/KEY: misc_feature
<222> LOCATION: (4)
<223> OTHER INFORMATION: n is pseudoisocytosine
<221> NAME/KEY: misc_feature
<222> LOCATION: (7)..(8)
<223> OTHER INFORMATION: Bases 7 and 8 are linked via three consecutive
      8-amino-3, 6-dioxaoctanoic acid groups (egl)

<400> SEQUENCE: 76
tntntttttt ctct                                                      14

<210> SEQ ID NO 77
<211> LENGTH: 14
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (2)
<223> OTHER INFORMATION: n is 1,8-naphthyridin-2,7(1,8H)-dione
<221> NAME/KEY: misc_feature
<222> LOCATION: (4)
<223> OTHER INFORMATION: n is 1,8-naphthyridin-2,7(1,8H)-dione
<221> NAME/KEY: misc_feature
<222> LOCATION: (7)..(8)
<223> OTHER INFORMATION: Bases 7 and 8 are linked via three consecutive
      8-amino-3,6-dioxaoctanoic acid groups (egl)

<400> SEQUENCE: 77
tntntttttt ctct                                                      14

<210> SEQ ID NO 78
<211> LENGTH: 13
<212> TYPE: DNA
<213> ORGANISM: Artificial Sequence
<220> FEATURE:
<223> OTHER INFORMATION: Description of Artificial Sequence: Novel
      Sequence

<400> SEQUENCE: 78
cgcagagaga cgc                                                       13

<210> SEQ ID NO 79
<211> LENGTH: 14
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (7)..(8)
<223> OTHER INFORMATION: Bases 7 and 8 are linked via three consecutive
      8-amino-3, 6-dioxaoctanoic acid groups (egl)

<400> SEQUENCE: 79
tctctcttct ctct                                                      14

<210> SEQ ID NO 80
<211> LENGTH: 14
<212> TYPE: DNA
```

```
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (2)
<223> OTHER INFORMATION: n is pseudoisocytosine
<221> NAME/KEY: misc_feature
<222> LOCATION: (4)
<223> OTHER INFORMATION: n is pseudoisocytosine
<221> NAME/KEY: misc_feature
<222> LOCATION: (6)
<223> OTHER INFORMATION: n is pseudoisocytosine
<221> NAME/KEY: misc_feature
<222> LOCATION: (7)..(8)
<223> OTHER INFORMATION: Bases 7 and 8 are linked via three consecutive
      8-amino-3, 6-dioxaoctanoic acid groups (egl)

<400> SEQUENCE: 80
tntntnttct ctct                                                      14

<210> SEQ ID NO 81
<211> LENGTH: 14
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (2)
<223> OTHER INFORMATION: n is phenothiazine
<221> NAME/KEY: misc_feature
<222> LOCATION: (4)
<223> OTHER INFORMATION: n is phenothiaine
<221> NAME/KEY: misc_feature
<222> LOCATION: (6)
<223> OTHER INFORMATION: n is phenothiane
<221> NAME/KEY: misc_feature
<222> LOCATION: (7)..(8)
<223> OTHER INFORMATION: Bases 7 and 8 are linked via three consecutive
      8-amino-3, 6-dioxaoctanoic acid groups (egl)

<400> SEQUENCE: 81
tntntnttct ctct                                                      14

<210> SEQ ID NO 82
<211> LENGTH: 14
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (2)
<223> OTHER INFORMATION: n is 1,8-naphthyridin-2, 7(1,8H)-dione
<221> NAME/KEY: misc_feature
<222> LOCATION: (4)
<223> OTHER INFORMATION: n is 1,8-naphthyridin-2,7 (1,8H)-dione
<221> NAME/KEY: misc_feature
<222> LOCATION: (6)
<223> OTHER INFORMATION: n is 1,8-naphthyridin-2,7 (1,8H)-dione
<221> NAME/KEY: misc_feature
<222> LOCATION: (7)..(8)
<223> OTHER INFORMATION: Bases 7 and 8 are linked via three consecutive
      8-amino-3, 6-dioxaoctanoic acid groups (egl)

<400> SEQUENCE: 82
tntntnttct ctct                                                      14

<210> SEQ ID NO 83
<211> LENGTH: 13
<212> TYPE: DNA
<213> ORGANISM: Artificial Sequence
```

```
<220> FEATURE:
<223> OTHER INFORMATION: Description of Artificial Sequence: Novel
      Sequence

<400> SEQUENCE: 83
cgcaagggaa cgc                                                          13

<210> SEQ ID NO 84
<211> LENGTH: 14
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (7)..(8)
<223> OTHER INFORMATION: Bases 7 and 8 are linked via three consecutive
      8-amino-3, 6-dioxaoctanoic acid groups (egl)

<400> SEQUENCE: 84
ttcccttttc cctt                                                         14

<210> SEQ ID NO 85
<211> LENGTH: 14
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (3)..(5)
<223> OTHER INFORMATION: n is pseudoisocytosine
<221> NAME/KEY: misc_feature
<222> LOCATION: (7)..(8)
<223> OTHER INFORMATION: Bases 7 and 8 are linked via three consecutive
      8-amino-3, 6-dioxaoctanoic acid groups (egl)

<400> SEQUENCE: 85
ttnnnttttc cctt                                                         14

<210> SEQ ID NO 86
<211> LENGTH: 14
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (3)..(5)
<223> OTHER INFORMATION: n is phenothiazine
<221> NAME/KEY: misc_feature
<222> LOCATION: (7)..(8)
<223> OTHER INFORMATION: Bases 7 and 8 are linked via three consecutive
      8-amino-3, 6-dioxaoctanoic acid groups (egl)

<400> SEQUENCE: 86
ttnnnttttc cctt                                                         14

<210> SEQ ID NO 87
<211> LENGTH: 14
<212> TYPE: DNA
<213> ORGANISM: Artificial Sequence
<220> FEATURE:
<223> OTHER INFORMATION: Description of Artificial Sequence: Novel
      Sequence
<221> NAME/KEY: misc_feature
<222> LOCATION: (3)..(5)
<223> OTHER INFORMATION: n is 1,8-naphthyridin-2, 7 (1,8H)-dione
<221> NAME/KEY: misc_feature
<222> LOCATION: (7)..(8)
```

```
<223> OTHER INFORMATION: Bases 7 and 8 are linked via three consecutive
      8-amino-3, 6-dioxaoctanoic acid groups (egl)

<400> SEQUENCE: 87
ttnnnttttc cctt                                                            14
```

PEPTIDE NUCLEIC ACID MONOMERS AND OLIGOMERS

CROSS REFERENCE TO RELATED APPLICATIONS

This application is a continuation in part of U.S. Ser. No. 08/862,629, filed May 23, 1997, the disclosure of which is hereby incorporated by reference in its entirety.

FIELD OF THE INVENTION

The present invention is directed to oligomeric compounds and their constituent monomers, especially peptide nucleic acid (PNA) oligomers and monomers. The peptide nucleic acid oligomers are useful for forming triple helix (triplex) structures with nucleic acids with increased binding specificity. In one aspect of the present invention novel PNA oligomers have increased specificity for thymidine and deoxyuridine in triplex structures.

BACKGROUND OF THE INVENTION

Peptide nucleic acids are useful surrogates for oligonucleotides in binding to both DNA and RNA. See Egholm et al., *Nature*, 1993, 365, 566–568 and references cited therein).

PNA binds both DNA and RNA to form PNA/DNA or PNA/RNA duplexes. The resulting PNA/DNA or PNA/RNA duplexes are bound with greater affinity than corresponding DNA/DNA or DNA/RNA duplexes as evidence by their higher melting temperatures (Tm). This high thermal stability has been attributed to the neutrality of the PNA backbone, which does not encounter the charge repulsion present in DNA or RNA duplexes. The neutral backbone of the PNA also renders the Tms of PNA/DNA(RNA) duplexes practically independent of salt concentration. Thus the PNA/DNA duplex offers a further advantage over DNA/DNA duplex interactions which are highly dependent on ionic strength. Homopyrimidine PNAs have been shown to bind complementary DNA or RNA forming $(PNA)_2$/DNA(RNA) triplexes of high thermal stability (see, e.g., Nielsen, et al., *Science*, 1991, 254, 1497; Egholm, et al., J. Am. Chem. Soc., 1992, 114, 1895; Egholm, et al., J. Am. Chem. Soc., 1992, 114, 9677).

In addition to increased affinity, PNA has also been shown to bind to DNA with increased specificity. When a PNA/DNA duplex mismatch is melted relative to the DNA/DNA duplex there is seen an 8 to 20° C. drop in the Tm. This magnitude of a drop in Tm is not seen with the corresponding DNA/DNA duplex with a mismatch present. See Egholm, M., et al., *Nature* 1993 365 p. 566.

The binding of a PNA strand to a DNA or RNA strand can occur in one of two orientations. The orientation is said to be anti-parallel when the DNA or RNA strand in a 5' to 3' orientation binds to the complementary PNA strand such that the carboxyl end of the PNA is directed towards the 5' end of the DNA or RNA and amino end of the PNA is directed towards the 3' end of the DNA or RNA. In the parallel orientation the carboxyl end and amino end of the PNA are in reverse orientation with respect to the 5'-3' direction of the DNA or RNA.

Because of their properties, PNAs are known to be useful in several different applications. In particular, PNAs have been used to form duplexes and triplexes with complementary RNA or DNA (see e.g., Knudsen et al., *Nucleic Acids Res.*, 1996, 24, 494–500; and Nielsen et al., *J. Am. Chem. Soc.*, 1996, 118, 2287–2288). Additionally, several review articles have recently been published in this area. See e.g., Hyrup et al., *Bioorganic & Med. Chem.*, 1996, 4, 5–23; Nielsen, "Peptide nucleic acid (PNA): A lead for gene therapeutic drugs," in Trainor (Ed.), *Perspectives Drug Disc. Des.*, 1996, 4, 76–84.

Since PNAs have stronger binding and greater specificity than oligonucleotides, they are of great utility as probes in cloning, blotting procedures, and in applications such as fluorescence in situ hybridization (FISH). Homopyrimidine PNAs are used for strand displacement in homopurine targets. The local triplex inhibits gene transcription. Additionally, the restriction sites that overlap with or are adjacent to the D-loop will not be cleaved by restriction enzymes. The binding of PNAs to specific restriction sites within a DNA fragment can inhibit cleavage at those sites. Such inhibition is useful in cloning and subcloning procedures. Labeled PNAs are also used to directly map DNA molecules by hybridizing PNA molecules having a fluorescent or other type of detectable label to complementary sequences in duplex DNA using strand invasion.

PNAs also have been used to detect point mutations in PCR-based assays (PCR clamping). In PCR clamping, PNA is used to detect point mutations in a PCR-based assay, e.g. the distinction between a common wild type allele and a mutant allele, in a segment of DNA under investigation. Typically, a PNA oligomer complementary to the wild type sequence is synthesized and included in the PCR reaction mixture with two DNA primers, one of which is complementary to the mutant sequence. The wild type PNA oligomer and the DNA primer compete for hybridization to the target. Hybridization of the DNA primer and subsequent amplification will only occur if the target is a mutant allele. With this method, the presence and exact identity of a mutant can be determined.

Considerable research is being directed to the application of oligonucleotides and oligonucleotide analogs that bind complementary DNA and RNA strands for use as diagnostics, research reagents and potential therapeutics. For many uses, the oligonucleotides and oligonucleotide analogs must be transported across cell membranes or taken up by cells to express activity.

PCT/EP/01219 describes novel peptide nucleic acid (PNA) compounds which bind complementary DNA and RNA more tightly than the corresponding DNA. It is desirable to append to these compounds groups which modulate or otherwise influence their activity or their membrane or cellular transport. One method for increasing such transport is by the attachment of a pendant lipophilic group.

The synthesis of peptide nucleic acids via preformed monomers has been described in International patent applications WO 92/20702 and WO 92/20703, the contents of each of which are incorporated herein by reference in their entirety. Recent advances have also been reported on the synthesis, structure, biological properties, and uses of PNAs. See for example WO 93/12129 and U.S. Pat. No. 5,539,083 to Cook et al., Egholm et al., *Nature*, 1993, 365, 566–568, Nielsen et al., *Science*, 1991, 254, 1497–1500; and Egholm et al., *J. Am. Chem. Soc.*, 1992, 114, 1895–1897. Peptide nucleic acids also have been demonstrated to effect strand displacement of double stranded DNA (see Patel, D. J., *Nature*, 1993, 365, 490–492). The contents of each of the foregoing patents and publications are incorporated herein by reference in their entirety.

Triple helix formation by oligonucleotides has been an area of intense investigation since sequence-specific cleavage of double-stranded deoxyribonucleic acid (DNA) was demonstrated by Moser et al., *Science*, 1987, 238, 645–650.

Triplex-forming oligonucleotides are believed to be of potential use in gene therapy, diagnostic probing, and other biomedical applications. See e.g., Uhlmann et al., *Chemical Reviews*, 1990, 90, 543–584.

Pyrimidine oligonucleotides have been shown to form triple helix structures through binding to homopurine targets in double-stranded DNA. In these structures the new pyrimidine strand is oriented parallel to the purine Watson-Crick strand in the major groove of the DNA, and binds through sequence-specific Hoogsteen hydrogen bonds. The sequence-specificity is derived from thymine recognizing adenine (T:A-T) and protonated cytosine recognizing guanine ($C^+$:G-C). See Best et al.,*J. Am. Chem. Soc.*, 1995, 117, 1187–1193). In a less well-studied triplex motif, purine-rich oligonucleotides bind to purine targets of double-stranded DNA. The orientation of the third strand in this motif is anti-parallel to the purine Watson-Crick strand, and the specificity is derived from guanine recognizing guanine (G:G-C) and thymine or adenine recognizing adenine (A:A-T or T:A-T). See Greenberg et al., *J. Am. Chem. Soc.*, 1995, 117, 5016–5022.

Homopyrimidine PNAs form highly stable PNA:DNA-PNA complexes with complementary oligonucleotides. The formation of triple helix structures involving two PNA strands and one nucleotide strand has been previously reported in U.S. patent application Ser. No. 08/088,661, filed Jul. 2, 1993, entitled Double-Stranded Peptide Nucleic Acids, the contents of which are incorporated herein by reference in their entirety. The formation of triplexes in which the Hoogsteen strand is parallel to the DNA purine target strand is preferred to formation of anti-parallel complexes. This allows for the use of bis-PNAs to obtain triple helix structures with increased pH-independent thermal stability using pseudoisocytosine instead of cytosine in the Hoogsteen strand. See, Egholm et al., *J. Am. Chem. Soc.*, 1992, 114, 1895–1897, also see Published PCT application WO 96/02558 the entire contents of each of which are incorporated herein by reference.

Peptide nucleic acids have been shown to have higher binding affinities (as determined by their melting temperatures) for both DNA and RNA than that of DNA or RNA to either DNA or RNA. This increase in binding affinity makes these peptide nucleic acid oligomers especially useful as molecular probes and diagnostic agents for nucleic acid species.

It has been previously shown that a carbazole-like 2′-deoxycytidine analog incorporated into oligonucleotides will pair specifically with guanine in complementary RNA in a duplex motif (U.S. Pat. No. 5,502,177, issued Mar. 26, 1996, entitled Pyrimidine Derivatives for Labeled Binding Partners; Matteucci, M. D., von Krosigk, U., *Tetrahetron Letters*, 1996, 37, 5057–5060; Kuei-Ying, L., et al., *J. Am. Chem.*, 1995, 117, 3873–3874).

The current limitations in the formation of triplex structures (such as the limitation to homopurine targets) is one of the major difficulties for sequence-specific recognition of defined sites of DNA by peptide nucleic acids. See Nielsen, *J. Am. Chem. Soc.*, 1996, 118, 2287–2288. Accordingly, there is a need for new PNA oligomers containing nucleobase-binding moieties that can bind Watson-Crick base pairs, preferentially within the pyrimidine triple helix motif.

SUMMARY OF THE INVENTION

Provided in accordance with the present invention are oligomeric compounds, particularly peptide nucleic acids, comprising a moiety having the Formula I:

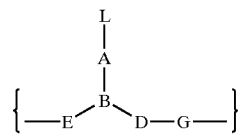

wherein:
L is an adenosine-thymidine nucleobase pair recognition moiety;
A is a single bond, a methylene group or a group of formula:

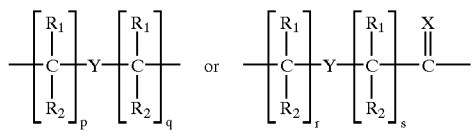

where:
X is O, S, Se, $NR_3$, $CH_2$ or $C(CH_3)_2$;
Y is a single bond, O, S or $NR_4$;
each p, q, r and s is, independently, zero or an integer from 1 to 5;
each $R_1$ and $R_2$ is, independently, selected from the group consisting of hydrogen, ($C_1$–$C_4$)alkyl which may be hydroxy- or alkoxy- or alkylthio-substituted, hydroxy, alkoxy, alkylthio, amino and halogen; and
each $R_3$ and $R_4$ is, independently, selected from the group consisting of hydrogen, ($C_1$–$C_4$)alkyl, hydroxy- or alkoxy- or alkylthio-substituted ($C_1$–$C_4$) alkyl, hydroxy, alkoxy, alkylthio and amino;
B is N or $R_3$—$N^+$, where $R_3$ is as defined above;
E is $CR_6R_7$, $CHR_6CHR_7$ or $CR_6R_7CH_2$, where $R_6$ is hydrogen and $R_7$ is selected from the group consisting of the side chains of naturally occurring alpha amino acids, or $R_6$ and $R_7$ are independently selected from the group consisting of hydrogen, ($C_2$–$C_6$)alkyl, aryl, aralkyl, heteroaryl, hydroxy, ($C_1$–$C_6$)alkoxy, ($C_1$–$C_6$) alkylthio, $NR_3R_4$ and $SR_5$, where $R_3$ and $R_4$ are as defined above, and $R_5$ is hydrogen, ($C_1$–$C_6$)alkyl, hydroxy-, alkoxy-, or alkylthio-substituted ($C_1$–$C_6$) alkyl, or $R_6$ and $R_7$ taken together complete an alicyclic or heterocyclic system;
D is $CR_6R_7$, $CH_2CR_6R_7$ or $CHR_6CHR_7$, where $R_6$ and $R_7$ are as defined above; and
G is —$NR_3CO$—, —$NR_3CS$—, —$NR_3SO$— or —$NR_3SO_2$—, in either orientation, where $R_3$ is as defined above.

In preferred embodiments, the monomeric unit has the Formula II:

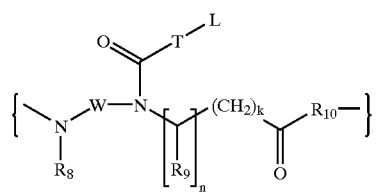

wherein:
R$_8$ is H, COCH$_3$ or an amino protecting group;
R$_9$ is hydrogen or a side chain of a naturally occurring amino acid;
R$_{10}$ is O, NH, O-alkylene or a lysine residue;
W is —(CH$_2$)$_m$— where m is from 0 to about 6, or

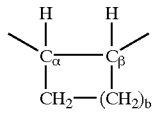

where b is an integer from 0 to 4;
k is from 0 to about 5;
n is 0 or 1;
L has the formula

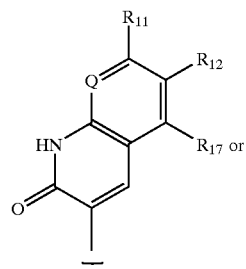

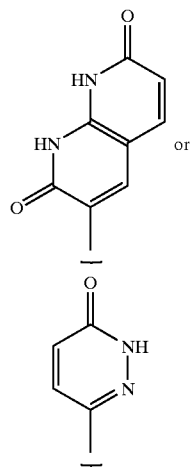

Q is CH or N;
R$_{17}$ is H or C$_1$–C$_8$ alkyl;
each R$_{11}$ and R$_{12}$ is, independently, H, C$_1$–C$_8$ alkyl, or halogen;
or R$_{11}$ and R$_{12}$ together with the carbon atoms to which they are attached form a phenyl group;
T has the formula:

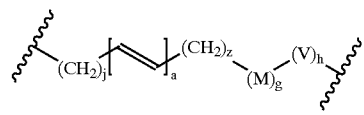

j and z are each, independently, from 0 to about 5 with the sum of j and z being from 1 to 7;
M is C(=O), S(O)$_2$, phenyl or P(O)$_2$;
V is NH, S, or CH$_2$; and
a, h and g are each independently 0 or 1.

Also provided in accordance with the present invention are monomeric compounds having the Formula III:

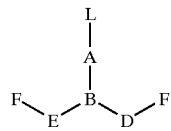

wherein:
L, A, B, D and E have the meaning described above, and each F is, independently, NHR$_3$ or NPgR$_3$, where R$_3$ is as defined above, and Pg is an amino protecting group.

In preferred embodiments, the monomeric compounds of the invention have the Formula IV:

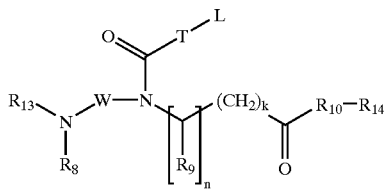

wherein:
R$_8$, R$_9$, T, L, W, k and n have the meaning described above, and R$_{13}$ and R$_{14}$ are each independently H or a protecting group.

In some preferred embodiments of the compounds of the invention, g and h are each 0. In more preferred embodiments g and h are each 0, and a is 0. In further preferred embodiments a is 0, g is 0, X is NH and h is 1.

In some preferred embodiments, L one of the formulas:

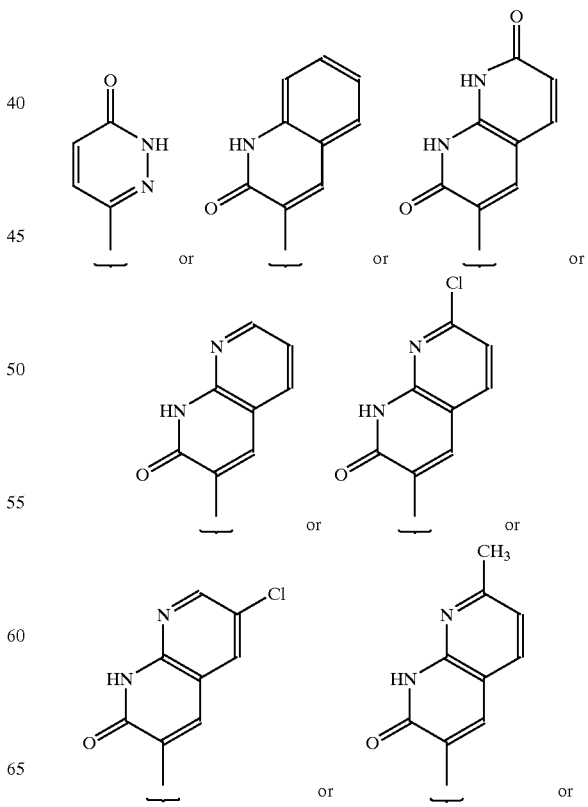

-continued

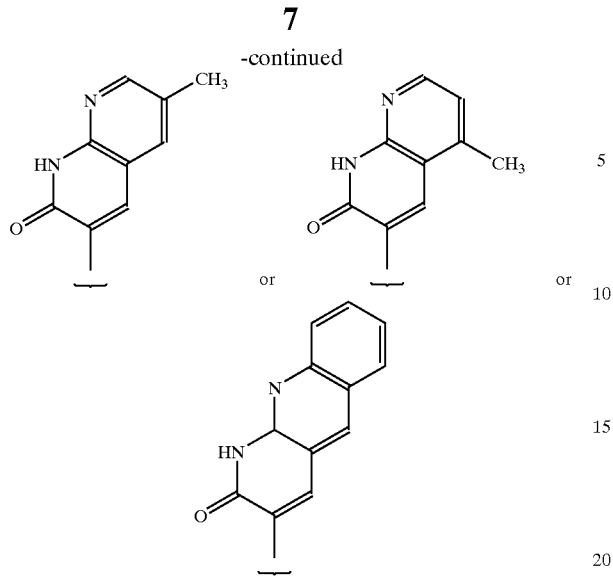

In some preferred embodiments $R_4$ and $R_5$ are each H. In further preferred embodiments $R_4$ and $R_5$ together with the atoms to which they are attached from a phenyl ring.

In some preferred embodiments Q is N; and in other preferred embodiments Q is CH.

Preferably T is lower alkyl or alkylamino. In especially preferred embodiments T is $—CH_2—CH_2—NH—$, $—CH_2—$, $—CH_2—CH_2—$, $—O—CH_2—CH_2—$, $—O—CH_2—CH_2—CH_2—$, $—(CH_2)_m—$.

In other preferred embodiments W has the formula:

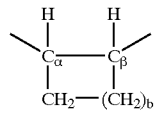

where b is preferably an integer between 0 and 4, with 2 and 3 being particularly preferred. In further preferred embodiments at least one of Cα or Cβ is in the S configuration.

In some preferred embodiments, the compounds of the invention are peptide nucleic acids. In other preferred embodiments the compounds of the invention comprise a plurality of peptide nucleic acid oligomers, preferably 2 oligomers, that are linked by linking groups, wherein at least one of the peptide nucleic acid oligomers comprises a moiety having Formula II. In particularly preferred embodiments two peptide nucleic acid oligomers are linked by a linking moiety, which is preferably one or more 8-amino-3,6-dioxaoctanoic acid groups and more preferable three 8-amino-3,6-dioxaoctanoic acid groups.

Some particularly preferred embodiments of the compounds of the invention have the formula:

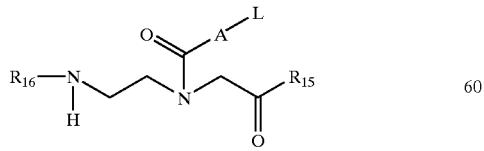

$R_{15}$ is OH, a protected hydroxyl group, or a protecting group; and $R_{16}$ is H or an amino protecting group.

L has the formula:

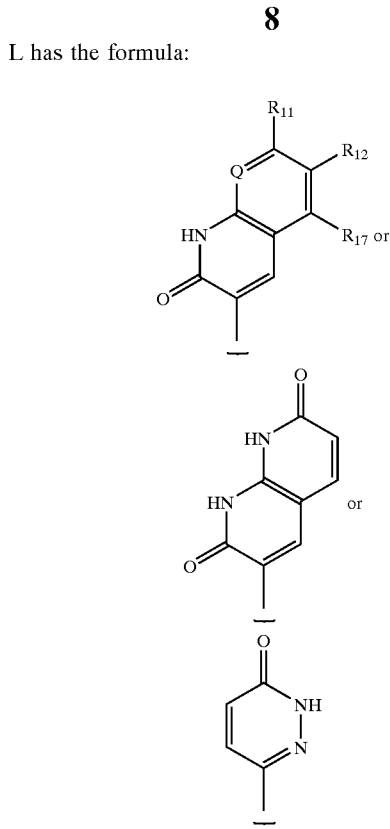

Q is CH or N;

$R_{17}$ is H or $C_1$–$C_8$ alkyl;

each $R_{11}$ and $R_{12}$ is, independently, H, $C_1$–$C_8$ alkyl, or halogen;

or $R_{11}$ and $R_{12}$ together with the carbon atoms to which they are attached form a phenyl group;

A is a single bond, a methylene group or a group of formula:

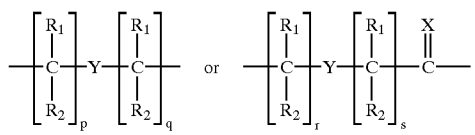

where:

X is O, S, Se, $NR_3$, $CH_2$ or $C(CH_3)_2$;

Y is a single bond, O, S or $NR_4$;

each p, q, r and s is, independently, zero or an integer from 1 to 5;

each $R_1$ and $R_2$ is, independently, selected from the group consisting of hydrogen, $(C_1$–$C_4)$alkyl which may be hydroxy- or alkoxy- or alkylthio-substituted, hydroxy, alkoxy, alkylthio, amino and halogen; and each $R_3$ and $R_4$ is, independently, selected from the group consisting of hydrogen, $(C_1$–$C_4)$alkyl, hydroxy- or alkoxy- or alkylthio-substituted $(C_1$–$C_4)$ alkyl, hydroxy, alkoxy, alkylthio and amino.

Also provided in accordance with the present invention are compositions, preferably triplex compounds, comprising a single stranded DNA coding for a sequence suspected of being implicated in a disease state and containing one or more thymine residues; a first peptide nucleic acid oligomer that comprises a region that is complementary to a region of the single stranded nucleic acid; and a second peptide nucleic acid oligomer comprising a sequence that is complementary to a region of the single stranded nucleic acid, the second peptide nucleic acid oligomer having at one or more positions complementary to the thymine residues of the single stranded nucleic acid a residue having a non purine nucleobase, preferably a residue of Formula II.

The present invention also provides methods for forming a triplex compound comprising the steps of:

(a) selecting a single stranded nucleic acid containing one or more thymine residues;

(b) providing a first oligomer that comprises a region that is complementary to a region of the single stranded nucleic acid;

(c) contacting the single stranded nucleic acid and the first oligomer with a second oligomer, where the second oligomer is a peptide nucleic acid oligomer comprising a sequence that is complementary to a region of the single stranded nucleic acid and has at one or more positions complementary to the thymine residues of the single stranded nucleic acid a residue of Formula II, for a time and under conditions effective to form the triple helix compound. Preferably, the first oligomer is PNA or DNA.

In preferred embodiments of the methods of the invention the first oligomer is oriented antiparallel to the single stranded nucleic acid, and the second oligomer is oriented parallel to the single stranded nucleic acid in the triplex compound. In particularly preferred embodiments the triplex compound has the formula PNA-DNA-PNA.

Preferably, the single stranded nucleic acid is DNA or RNA.

In further preferred embodiments the first oligomer is a peptide nucleic acid, and the first oligomer is linked to the second oligomer by a linking moiety.

In some preferred embodiments of the methods of the invention the first and second oligomers are each from 4 to about 20 nucleobases in length.

The present invention also provides methods for the detection of a chemical or microbiological entity which contains a known nucleobase sequence comprising:

selecting a nucleobase sequence from the chemical or microbiological entity which contains one or more thymine residues;

providing a PNA oligomer that contains a region that complementary to the selected nucleobase sequence;

contacting the selected nucleobase sequence of the chemical or microbiological entity and the complementary PNA oligomer with a further peptide nucleic acid oligomer which contains a sequence that is complementary to the selected nucleobase sequence, where the further peptide nucleic acid oligomer has at one or more positions complementary to the thymine residues of the selected nucleobase sequence a residue of Formula II, to form a triple helix compound; and detecting the triple helix compound.

Methods are also provided for the sequence-specific recognition of a double-stranded polynucleotide, comprising contacting the polynucleotide with a compound having a residue of Formula II.

Methods are also provided for the sequence-specific recognition of a double-stranded polynucleotide, comprising contacting the polynucleotide with an oligomeric compound that binds to the polynucleotide to form a triplex structure, wherein the oligomeric compound comprises a monomeric unit having Formula I, more preferably Formula II.

DESCRIPTION OF PREFERRED EMBODIMENTS

In one aspect, the present invention provides novel oligomeric compounds, especially peptide nucleic acids, that are useful as research reagents, and as specific probes for complementary nucleic acid. The present invention also provides monomeric synthons useful in the preparation of the oligomeric compounds.

In preferred embodiments the compounds of the invention contain a moiety of Formula I:

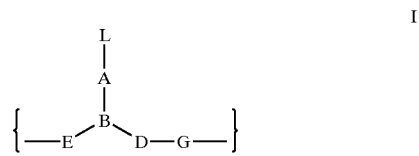

wherein:

L is an adenosine-thymidine nucleobase pair recognition moiety;

A is a single bond, a methylene group or a group of formula:

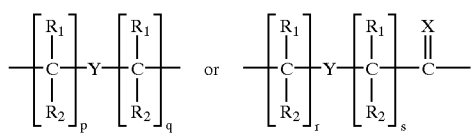

where:

X is O, S, Se, $NR_3$, $CH_2$ or $C(CH_3)_2$;

Y is a single bond, O, S or $NR_4$;

each p, q, r and s is, independently, zero or an integer from 1 to 5;

each $R_1$ and $R_2$ is, independently, selected from the group consisting of hydrogen, $(C_1-C_4)$alkyl which may be hydroxy- or alkoxy- or alkylthio-substituted, hydroxy, alkoxy, alkylthio, amino and halogen; and each $R_3$ and $R_4$ is, independently, selected from the group consisting of hydrogen, $(C_1-C_4)$alkyl, hydroxy- or alkoxy- or alkylthio-substituted $(C_1-C_4)$ alkyl, hydroxy, alkoxy, alkylthio and amino;

B is N or $R_3$—$N^+$, where $R_3$ is as defined above;

E is $CR_6R_7$, $CHR_6CHR_7$ or $CR_6R_7CH_2$, where $R_6$ is hydrogen and $R_7$ is selected from the group consisting of the side chains of naturally occurring alpha amino acids, or $R_6$ and $R_7$ are independently selected from the group consisting of hydrogen, $(C_2-C_6)$alkyl, aryl, aralkyl, heteroaryl, hydroxy, $(C_1-C_6)$alkoxy, $(C_1-C_6)$ alkylthio, $NR_3R_4$ and $SR_5$, where $R_3$ and $R_4$ are as defined above, and $R_5$ is hydrogen, $(C_1-C_6)$alkyl, hydroxy-, alkoxy-, or alkylthio-substituted $(C_1-C_6)$ alkyl, or $R_6$ and $R_7$ taken together complete an alicyclic or heterocyclic system;

D is $CR_6R_7$, $CH_2CR_6R_7$ or $CHR_6CHR_7$, where $R_6$ and $R_7$ are as defined above; and G is —$NR_3CO$—, —$NR_3CS$—, —$NR_3SO$— or —$NR_3SO_2$—, in either orientation, where $R_3$ is as defined above.

In more preferred embodiments the compounds of the present invention contain a moiety of Formula II:

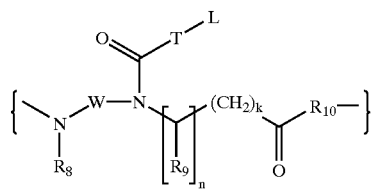

wherein:

$R_8$ is H, $COCH_3$ or an amino protecting group;

$R_9$ is hydrogen or a side chain of a naturally occurring amino acid;

$R_{10}$ is O, NH, O-alkylene or a lysine residue;

W is —$(CH_2)_m$— where m is from 0 to about 6, or

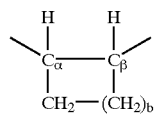

where b is an integer from 0 to 4;

k is from 0 to about 5;

n is 0 or 1;

L has the formula

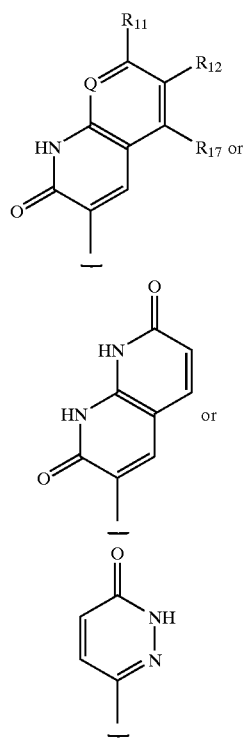

Q is CH or N;

$R_{17}$ is H or $C_1$–$C_8$ alkyl;

each $R_{11}$ and $R_{12}$ is, independently, H, $C_1$–$C_8$ alkyl, or halogen;

or $R_{11}$ and $R_{12}$ together with the carbon atoms to which they are attached form a phenyl group;

T has the formula:

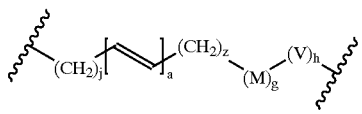

j and z are each, independently, from 0 to about 5 with the sum of j and z being from 1 to 7;

M is C(=O), $S(O)_2$, phenyl or $P(O)_2$;

V is NH, S, or $CH_2$; and a, h and g are each independently 0 or 1.

Preferred embodiments of the compounds of the invention include oligomeric compounds that contain one or more moieties of Formula II. There can be as few as one moiety of Formula II in the oligomer, or the majority of monomeric units in the oligomer can be moieties of Formula II.

Further preferred embodiments of the compounds of the invention include two PNA oligomers that are linked together by one or more linking moieties, wherein one or both of the PNA oligomers contain at least one moiety of Formula II ("bis-PNA oligomers"). The present invention also includes higher order linked PNA oligomers, wherein a plurality of PNA oligomers are linked by linking moieties, wherein one or more of the linked PNA oligomers contain at least one moiety of Formula II.

As used herein, the term "peptide nucleic acid" (PNA) refers to compounds that in some respects are analogous to oligonucleotides, but which differ in structure. In peptide nucleic acids, the deoxyribose backbone of oligonucleotides has been replaced with a backbone having peptide linkages. Each subunit has attached a naturally occurring or non-naturally occurring base. One such backbone is constructed of repeating units of N-(2-aminoethyl)glycine linked through amide bonds.

The present invention also provides PNA monomers, which are useful, for example, in the preparation of the PNA oligomers of the invention. In some preferred embodiments the PNA monomers of the present invention have an achiral backbone. One preferred example of an achiral PNA backbone is the 2-aminoethylglycine backbone. See, for example, International patent applications WO 92/20702 and WO 92/20703, the contents of each of which are incorporated herein by reference.

In other preferred embodiments, the invention provides PNA monomers containing a chiral backbone. In some preferred embodiments, chirality is introduced into the PNA backbone through the incorporation of an aliphatic cyclic structure. In one particularly preferred embodiment, the aliphatic cyclic structure includes the α and β carbons of the 2-aminoethyl portion of an aminoethylglycine backbone, and has the formula:

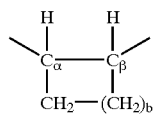

where b is an integer from 0 to 4; α denotes the carbon that is adjacent to the glycyl amino group; and β denotes the carbon that is one adjacent to the a carbon. The aliphatic cyclic structure may be a 4, 5, 6 or 7 membered ring. In preferred embodiments the aliphatic cyclic structure is a 5 or 6 membered ring, with 6 being especially preferred.

The use of optically active reagents permits the synthesis of pure SS, RR, SR, and RS isomers. The SS isomer is preferred in some embodiments of the present invention.

Typically, monomers having a chiral backbone are prepared using (1,2)-diaminocyclohexane, which is available as the cis, or the trans isomer. The cis-(1,2)-diaminocyclohexane is a meso compound. Use of such meso compound requires resolution of a racemic mixture. The trans-(1,2)-diaminocyclohexane is commercially available in enantiomerically pure form, making it well suited for monomers of predetermined chirality about both the Cα and the Cβ of the 2-aminoethyl portion of the backbone.

The diamine is typically protected at one of the amino groups with di-t-butylpyrocarbonate ($Boc_2O$), followed by N-alkylation with methyl bromoacetate to give the chiral backbone. Coupling of a ligand (suitably protected where necessary) with the chiral backbone using DCC/DhbtOH followed by basic hydrolysis will give the desired monomer containing the chiral backbone. In this manner the SS and RR monomers may be synthesized. The RS and the SR isomers can be synthesized using the cis-(1,2)-diaminocyclohexane, and resolving the resulting racemic mixture. Resolution can be achieved, for example, by liquid chromatography.

The resulting monomer has increased conformational restriction, and is expected to increase the lipophilicity of the monomer. PNA monomers containing chiral backbones are disclosed in copending U.S. Pat. No. 5,972,296, the contents of which are hereby incorporated by reference in their entirety.

PNA oligomers comprising at least one chiral monomer of the invention are prepared in accordance with methods known to those skilled in the art. Established methods for the stepwise or fragmentwise solid-phase assembly of amino acids into peptides normally employ a beaded matrix of slightly cross-linked styrene-divinylbenzene copolymer, the cross-linked copolymer having been formed by the pearl polymerization of styrene monomer to which has been added a mixture of divinylbenzenes. A level of 1–2% cross-linking is usually employed. Such a matrix also can be used in solid-phase PNA synthesis in accordance with the present invention.

In some preferred embodiments, the PNA oligomers of the invention contain one or more chiral monomeric subunits. The PNA oligomers of the invention can contain one chiral subunit, a plurality of chiral subunits, or can be composed primarily or entirely of chiral subunits.

Preferably, the PNA oligomer is prepared to be complementary to a target molecule, i.e. at least a portion of the PNA oligomer has the ability to hybridize due to Watson-Crick base pair attraction to the target molecule, or due to Hoogsteen hydrogen bonds in triplex structures.

In preferred embodiments the aminoalkyl nitrogen of the PNA backbone can bear a substituent, which is denoted $R_8$ in Formulas II and IV. Preferably, $R_8$ is hydrogen, $COCH_3$, or an amino protecting group.

Functional groups present on the compounds of the invention may contain protecting groups. Protecting groups are known per se as chemical functional groups that can be selectively appended to and removed from functionalities, such as amino groups and carboxyl groups. These groups are present in a chemical compound to render such functionality inert to chemical reaction conditions to which the compound is exposed. Any of a variety of protecting groups may be employed with the present invention. One preferred protecting group for amino groups is the Boc group. Other preferred protecting groups according to the invention may be found in Greene, T. W. and Wuts, P. G. M., "*Protective Groups in Organic Synthesis*" 2d. Ed., Wiley & Sons, 1991.

Substituent $R_9$ is hydrogen, or the sidechain of a naturally occurring amino acid. As used herein, the term "amino acid" denotes a molecule containing both an amino group and a carboxyl group, and has the general formula CH(COOH)($NH_2$)—(side chain). A naturally occurring amino acid is an amino acid that is found in nature; i.e., one that is produced by living organisms. One representative amino acid side chain is the lysyl side chain, —$(CH_2)_4$—$NH_2$. Other representative naturally occurring amino acids can be found, for example, in Lehninger, *Biochemistry*, Second Edition, Worth Publishers, Inc, 1975, pages 73–77.

In preferred embodiments $R_{10}$ is O, NH, O-alkylene, or a lysine residue. As used herein, the term "alkyl" includes straight-chain, branched and cyclic hydrocarbon groups such as, for example, ethyl, isopropyl and cyclopropyl groups. Preferred alkyl groups have 1 to about carbon atoms. The term "alkylene" denotes divalent alkyl groups; i.e., methylene (—$CH_2$—), ethylene (—$CH_2CH_2$—), propylene (—$CH_2CH_2CH_2$—), etc.

The term "alkoxy" has its accustomed meaning as an —O-alkyl group. An "alkylthio" group denotes a group of formula —S-alkyl. Halogens include fluorine, chlorine, Bromine, and iodine.

The term aryl is intended to denote monocyclic and polycyclic aromatic groups including, for example, phenyl, naphthyl, xylyl, pyrrole, and furyl groups. Although aryl groups (e.g., imidazole groups) can include as few as 3 carbon atoms, preferred aryl groups have 6 to about 14 carbon atoms, more preferably 6 to about 10 carbon atoms. Aralkyl and alkaryl groups according to the invention each include alkyl and aryl portions. Aralkyl groups are attached through their alkyl portions, and alkaryl groups are attached through their aryl portions. Benzyl groups provide one example of an aralkyl group, and p-toluyl provides an example of an alkaryl group. As used herein, the term "heterocyclic" denotes a ring system that includes at least one hetero atom, such as nitrogen, sulfur or oxygen. The term "heteroaryl" specifically denotes aryl heterocyclic groups.

In the context of this invention, the term "polynucleotide" refers to an oligomer or polymer of ribonucleic acid or deoxyribonucleic acid.

In the PNA monomers of the present invention, an adenosine-thymidine nucleobase pair recognition moiety is connected to the PNA backbone by a tether, denoted as substituent A in Formula I. In some preferred embodiments, the tether terminates in a carbonyl group, which is preferably attached to a nitrogen atom of the PNA backbone. In more preferred embodiments the tether terminates in a carbonyl group which is attached to the glycyl nitrogen of a 2-aminoethylgylcine backbone. In further preferred embodiments the tether terminates in a carbonyl group which is attached to the glycyl nitrogen of a chiral derivative of a 2-aminoethylgylcine backbone, wherein the α and β carbons of the 2-aminoethyl portion of the aminoethylglycine backbone participate in an alicyclic ring, as described above.

In some preferred embodiments the portion of the tether attached to the PNA-bound carbonyl group has the formula:

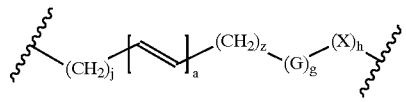

where j and z are each, independently, from 0 to about 5 with the sum of j and z being from 1 to 7; G is C(=O), S(O)$_2$, phenyl or P(O)$_2$; X is NH, S, or CH$_2$; and a, h and g are each independently 0 or 1. In some preferred embodiments, the tether is alkyl or alkylamino, preferably having fewer than about six carbons, with two carbons being especially preferred. Particularly preferred tethers include —CH$_2$—CH$_2$—NH—, —CH$_2$—, —CH$_2$—CH$_2$—, —O—CH$_2$—CH$_2$—, and —O—CH$_2$—CH$_2$—CH$_2$— groups. It is desirable to select the tether such that the ligand has the proper placement and orientation to maximize the interaction between the ligand and the AT pair (especially thymine) residing on complementary positions in the triplex structures. Preferably, the tether is linear and contains from 3 to 6 atoms in the linear chain, more preferably 4 or 5 atoms, with 4 being especially preferred.

In some preferred embodiments, at least one PNA monomer having a chiral center in the ethyl portion thereof is incorporated into the PNA oligomer at the site where a mismatch (i.e. variability of the target molecule) is expected or known to occur.

The PNA oligomers of the invention can have a variety of substituents attached thereto. For example, in some preferred embodiments the oligomers of the invention have a conjugate group attached, to afford easier detection or transport of the PNA. The conjugate group can be a reporter enzyme, a reporter molecule, a steroid, a carbohydrate, a terpene, a peptide, a protein, an aromatic lipophilic molecule, a non aromatic lipophilic molecule, a phospholipid, an intercalator, a cell receptor binding molecule, a crosslinking agent, a water soluble vitamin, a lipid soluble vitamin, an RNA cleaving complex, a metal chelator, a porphyrin, an alkylator, and polymeric compounds such as polymeric amines, polymeric glycols and polyethers. PNAs of the present invention can include one or more conjugates attached directly or through an optional linking moiety. When so derivatized, the PNA is useful, for example, as a diagnostic or therapeutic agent, to render other properties to a complementary nucleic acid or triplex in a test structure or to transfer a therapeutic or diagnostic agent across cellular membranes.

The conjugate group can be attached to the PNA oligomers of the invention anywhere on the PNA backbone, either on the monomeric unit of Formula II, or elsewhere on the PNA. The conjugate group can be attached to a monomer, and incorporated into the PNA oligomer. Alternatively, the conjugate group can be attached to the PNA oligomer after assembly from constituent monomers. Methods for the attachment of conjugate groups can be found in copending U.S. application ser. No. 08/319,411, filed Oct. 6, 1994, the contents of which are incorporated by reference in their entirety.

In some particularly preferred embodiments, the oligomeric compounds of the invention bear a reporter molecule such as a chromaphore or a fluorophore, for example fluorescein or rhodamine. For example, PNA oligomers of the invention, including those having at least one chiral monomer, are easily derivatized to include a fluorescein or rhodamine using an aminohexanoic linker group. These derivatized PNA oligomers are well suited for use as probes for a section of DNA of interest. Those skilled in the art will appreciate that the present invention is amenable to a variety of other types of labeling reagents and linkers.

The adenosine-thymidine nucleobase pair recognition moieties of the compounds of the present invention, represented by substituent L in Formulas I–IV, are surrogates for nucleobases that are ordinarily found in triple helix strands at positions complementary to thymidine (i.e., complementary to adenosine-thymidine base pairs). The adenosine-thymidine nucleobase pair recognition moieties of the invention can also be used as surrogates for thymine in antisense applications, by both duplex and triplex motifs.

Triplex structures which incorporate oligomers of the invention, which have a monomeric unit containing an adenosine-thymidine nucleobase pair recognition moiety at a position complementary to a Watson-Crick adenosine-thymidine base pair (that is, which have a monomeric unit of Formula I or II at a position complementary to the Watson-Crick adenosine-thymidine base pair), display increased binding (i.e., have a higher melting temperature) relative to otherwise identical triplex structures having a natural nucleobase at the site complementary to the Watson-Crick adenosine-thymidine base pair. Accordingly, the compounds of the invention are able to "recognize" thymine residues in triple helix structures by this increased binding. Thus, the term "adenosine-thymidine nucleobase pair recognition moiety" as defined herein is a non-natural heterocyclic moiety that, when substituted for a natural nucleobase able to bind to Watson-Crick base pairs in triple helix structures, forms a triplex structure having increased binding relative to identical triplexes not having the adenosine-thymidine nucleobase pair recognition moiety.

In some preferred embodiments of the invention the adenosine-thymidine nucleobase pair recognition moiety is a C-pyrimidine (e.g. a pyrimidine in which the linkage connecting the pyrimidine to the backbone either with or without a tether is made through a carbon and not a nitrogen atom) or an iso-pyrimidine.

The adenosine-thymidine nucleobase pair recognition moieties and tethers of the compounds of the invention, represented by —T—L in Formulas I–IV, are selected to afford the maximum affinity for complementary thymine residues in the DNA portion of triplex structures, for example PNA:DNA-PNA triplex structures. Although not wishing to be bound by a specific theory, it is believed that in order to recognize thymine of a T-A base-pair in the major groove of a Watson and Crick double helix structure, it is preferred that the ligand be connected to the PNA backbone with a tether that allows sufficient freedom to circumvent the 5-methyl group of thymine. In addition, the selected ligand preferably has a hydrogen donor that can bind to the 4-oxo group of thymine. A further useful feature is the presence of a second functionality, located on or attached to the ligand, that can act as a hydrogen acceptor to form a hydrogen bond to the N-6 hydrogen atoms of adenine. It is believed that the compounds of the present invention that recognize thymine in a Watson and Crick double helix structure posses these attributes.

Adenosine-thymidine nucleobase pair recognition moieties can be selected by methods known to those of skill in the art. For example, adenosine-thymidine nucleobase pair recognition moieties can be selected by appropriate computer modeling programs, such as the Insight II and Discover programs, available from Biosym, San Diego, Calif.

In some preferred embodiments adenosine-thymidine nucleobase pair recognition moieties have the formula:

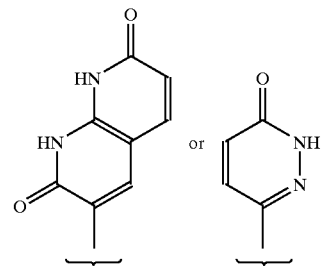

In other preferred embodiments adenosine-thymidine nucleobase pair recognition moieties have the formula:

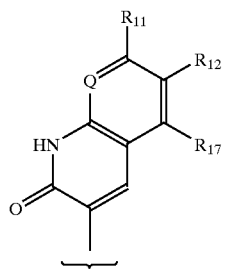

wherein

Q is CH or N;

R$_{17}$ is H or C$_1$–C$_8$ alkyl;

each R$_{11}$ and R$_{12}$ is, independently, H, C$_1$–C$_8$ alkyl, or halogen;

or R$_{11}$ and R$_{12}$ together with the carbon atoms to which they are attached form a phenyl group.

In another preferred embodiment, the tether connecting the adenosine-thymidine nucleobase pair recognition moiety, A in Formula I or T in Formula II, is —CH$_2$—CH$_2$—NH—, —CH$_2$—, —CH$_2$—CH$_2$—, —O—CH$_2$—CH$_2$—, or —O—CH$_2$—CH$_2$—CH$_2$—.

In particularly preferred embodiments, monomers of the present invention have the formula:

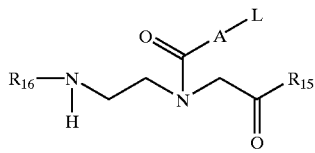

L has the formula:

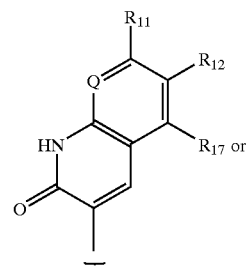

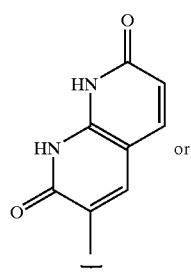

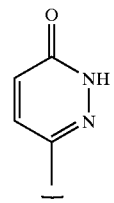

Q is CH or N;

R$_{17}$ is H or C$_1$–C$_8$ alkyl;

each R$_{11}$ and R$_{12}$ is, independently, H, C$_1$–C$_8$ alkyl, or halogen;

or R$_{11}$ and R$_{12}$ together with the carbon atoms to which they are attached form a phenyl group;

A is a single bond, a methylene group or a group of formula:

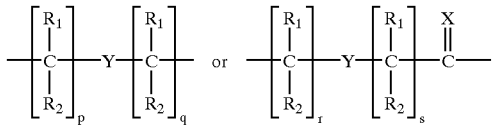

where:

X is O, S, Se, NR$_3$, CH$_2$ or C(CH$_3$)$_2$;

Y is a single bond, O, S or NR$_4$;

each p, q, r and s is, independently, zero or an integer from 1 to 5;

each R$_1$ and R$_2$ is, independently, selected from the group consisting of hydrogen, (C$_1$–C$_4$)alkyl which may be hydroxy- or alkoxy- or alkylthio-substituted, hydroxy, alkoxy, alkylthio, amino and halogen;

each R$_3$ and R$_4$ is, independently, selected from the group consisting of hydrogen, (C$_1$–C$_4$)alkyl, hydroxy- or alkoxy- or alkylthio-substituted (C$_1$–C$_4$) alkyl, hydroxy, alkoxy, alkylthio and amino;

R$_{15}$ is OH, a protected hydroxyl group, or a protecting group; and

R$_{16}$ is H or a protecting group.

The PNA oligomers and linked PNA oligomers of the present invention are useful for forming PNA$_2$/DNA triple helix structures. Preferred embodiments of the compounds of the invention include triple helix (i.e., triplex) PNA.DNA-PNA structures in which at least one of the PNA strands contains at least one monomer moiety in accordance with Formula I, preferably Formula II. In more preferred embodiments the two PNA oligomers in the PNA.DNA-PNA are constituent members of a bis-PNA; i.e., the two PNA oligomers are linked together by one or more linking moieties ("linking groups").

Linking moieties that link PNA oligomers in compounds of the invention are selected such that the PNA oligomers have sufficient freedom to permit formation of the triplex structure. A variety of groups can be used as linking moieties, for example "egl groups" (ethylene glycol) and "Aha groups" (6-amino hexanoic acid) linked together by amino acid groups. A further linking segment includes the above Aha groups interspaced with α-amino acids particularly glycine or lysine. One especially preferred linking moiety is one or more 8-amino-3,6-dioxaoctanoic acid residues which, effectively gives upon coupling, "multiple ethylene glycol units" ("egl").

A wide range of other compounds are also useful for the linking segment and thus are included within the scope of the present invention. Generally the linking segment is a compound having a primary amino group and a carboxy group separated with a space spanning group, wherein the space spanning group consists of one or more functional groups. Some representative space spanning groups are $C_1$ to $C_{20}$ alkyl, $C_2$ to $C_{20}$ alkenyl, $C_2$ to $C_{20}$ alkynyl, $C_1$ to $C_{20}$ alkanoyl having at least one O or S atom, $C_7$ to $C_{34}$ aralkyl, $C_6$–$C_{14}$ aryl and amino acids. Preferred alkanoyl groups can have from 1 to 10 hetero atoms such as O or S. Preferred alkanoyl groups include methyl, ethyl and propyl alkanoxy particularly polyethoxy, i.e., ethylene glycol. Amino acids including D, L, and DL isomers of α-amino acids as well as longer chain amino acids may also be linked together to form a linking segment. A particularly preferred amino acid is 6-amino hexanoic acid. Aralkyl groups used as space spanning groups may have the amino or the carboxy group located on the aromatic ring or spaced with one or more $CH_2$ groups wherein the total number of $CH_2$ groups is less than or equal to twenty. The position of substitution in an aralkyl linked PNA may be varied; however, ortho and meta are presently preferred because substitution at these positions, especially ortho, induce the bis PNA to be bent, thus facilitating location of the two joined peptide nucleic acid strands in spacial locations parallel to one another. Another group of bis PNAs that include induced bends are those that incorporate cis-alkenyl linkers or a proline linker.

In selecting a linking segment, one consideration is compatibility with PNA chemistry, and the ability to link a functional group on one end of a PNA to a functional group on one end of a second PNA. Also, the linking segment can be selected so as to be flexible, such that the two linked PNAs are able to interact with ssDNA, ssRNA or dsDNA in similar fashion to the way that two independent PNA single strands would so interact. Some preferred linking segments that have been shown to be effective have lengths of 23 and 24 atoms.

The term "complementary" as used herein has its accustomed meaning as the ability to form either Watson-Crick or Hoogsteen bonds within a nucleic acid (RNA or DNA) duplex, a PNA-nucleic acid duplex, a triplex structure including nucleic acid, PNA, or mixtures thereof.

In the $PNA_2$/DNA compounds of the invention, PNA oligomers are typically prepared as Watson-Crick antiparallel strands, and additional PNA oligomers are prepared as parallel (e.g. Hoogsteen) strands. In one preferred embodiment, the PNA monomers of the invention are used in the Hoogsteen strand in positions that are complementary to thymine or uracil in the target nucleic acid to increase the binding of the Hoogsteen strand, and hence increase the melting temperature (Tm) of the resulting triple helix that is formed.

As used herein, the term "binding affinity" refers to the ability of a duplex to bind to a target molecule via hydrogen bonds, van der Waals interactions, hydrophobic interactions, or otherwise. Target molecules include single stranded DNA or RNA, as well as duplexes between DNA, RNA, and their analogs such as PNA.

As used herein, the term "nucleobase" has its accustomed meaning as a heterocyclic base that is capable of participating in Watson-Crick or Hoogsteen bonds in nucleic acid duplex or triplex structures. These include the natural nucleobases adenine, guanine, cytosine, thymine and uracil, as well as unnatural nucleobases (i.e., nucleobase analogs) that are known to mimic the function of the natural nucleobases in DNA or RNA analogs. Representative nucleobase analogs can be found in, for example, *Antisense Research and Application*, Ed. S. T. Crooke and B. Lebleu, Chapter 15, CRC Press, 1993, and U.S. Pat. No. 3,687,808 to Merigan, et al., the contents of which are hereby incorporated by reference in their entirety.

In some preferred embodiments, the PNA oligomers of the present invention form triple helix structures with nucleic acid targets wherein the PNA oligomer has an increased binding affinity relative to previously reported PNA oligomers. The PNA oligomers and linked PNA oligomers having PNA monomer moieties of Formula I–IV in positions complementary to thymine or uracil in a nucleic acid target show increased binding specificity relative to the same triplex structure formed with linked PNA oligomers having adenine in positions that are complementary to thymine or uracil (see Example 5, infra).

Thus, the PNA oligomers and linked PNA oligomers of the invention find use in applications where it is desired to detect or identify oligonucleotide sequences containing thymidine residues. Accordingly, the PNA oligomers of the present invention are useful as research reagents and as diagnostic tools. In one preferred embodiment, the oligomers and linked oligomers of the invention are useful for the detection of nucleic acid sequences suspected of being implicated in a disease state, which contain one or more thymine residues. Accordingly, the present invention includes triplex structures containing nucleic acid sequences suspected of being implicated in a disease state, and at least one PNA oligomer of the invention.

In some preferred embodiments, compositions of the invention including single stranded DNA coding for a sequence suspected of being implicated in a disease state and containing one or more thymine residues; a first peptide nucleic acid that comprises a region that is complementary to a region of the single stranded nucleic acid; and a second peptide nucleic acid comprising a sequence that is complementary to a region of the single stranded nucleic acid, the peptide nucleic acid oligomer having at one or more positions complementary to the thymine residues of the single stranded nucleic acid a residue of Formula I, preferably Formula II.

The present invention also provides methods for forming a triple helix compound comprising (a) selecting a single stranded nucleic acid containing one or more thymine residues; (b) providing a first oligomer that comprises a region that is complementary to a region of the single stranded nucleic acid; (c) contacting the single stranded nucleic acid and the first oligomer with a second oligomer, wherein the second oligomer comprises a sequence that is complementary to a region of the single stranded nucleic acid, and has at one or more positions complementary to the thymine residues of the single stranded nucleic acid a residue of Formula I or II for a time and under conditions effective to form the triple helix compound.

In some preferred embodiments, the single stranded nucleic acid will be selected for its biological activity, such as its pathogenic properties. The first oligomer will be then be synthesized to include a region that is complementary to a region of the single stranded nucleic acid, preferably a region with more than one thymine residue. The contacting of the single stranded nucleic acid and the first oligomer with the second oligomer may be accomplished by a variety of means, known in the art, that promotes triplex formation. See for example, U.S. patent application Ser. No. 08/088, 661, for in vitro determination of a nucleic acid in a sample which may be made by pipetting one or more solutions containing said first and second oligomer as well as optionally all reagents necessary for effective triplex formation to the sample.

In preferred embodiments, methods are provided for the detection of a chemical or microbiological entity which contains a known nucleobase sequence comprising a) selecting a nucleobase sequence from the chemical or microbiological entity which contains one or more thymine residues; b) providing a PNA oligomer that contains a region that is complementary to the selected nucleobase sequence; c) contacting the selected nucleobase sequence of the chemical or microbiological entity and the complementary PNA oligomer with a further PNA oligomer which contains a sequence that is complementary to the selected nucleobase sequence, wherein the further PNA oligomer has at one or more positions complementary to the thymine residues of the selected nucleobase sequence a residue of Formula I or II to form a triple helix compound; and d) detecting the triple helix compound.

Detection of the triple helix compound can be accomplished by detection of a reporter molecule, such as a chromophore or fluorophore, that is bound covalently or non-covalently to the compound of the invention as described above. Useful conjugates are described in WO 95/14708, WO 95/16202 and WO 92/20703. Alternatively, detection may be by any of several means, including Tm studies, mass measurements and crosslinking studies.

The further PNA oligomer can alternatively have attached a moiety enabling immobilization on a solid support, such as polystyrene. One example of such a moiety is biotin which can be bound to polystyrene via a coating of streptavidine. Formation of the triple helical structure can then be accomplished by labels attached to either the other PNA oligomer or to the nucleobase sequence a chemical entity.

Chemical entities are understood to include chemically synthesized oligomers and chemically or enzymatically (for example via PCR) amplified nucleobase sequences containing compounds. Microbiological entities in connection with this invention are understood to include cells, for example from animals, vertebrates, bacterial or plants, or viruses, like HIV or HBV, plasmids or genomes.

In these analytical methods, the formation of the triplex structure having the further PNA oligomer incorporated is taken as an indication of the presence of the entity in the sample analyzed, for example the sample containing the chemical or microbiological entity.

The present invention also provides methods for sequence-specific recognition of a double-stranded polynucleotide, comprising contacting said polynucleotide with a compound of Formula I or II.

The present invention further provides methods for sequence-specific recognition of a double-stranded polynucleotide, comprising contacting the polynucleotide with an oligomeric compound that binds to the polynucleotide to form a triplex structure, the oligomeric compound comprising a monomeric unit having the Formula I or II.

Additional advantages and novel features of this invention will become apparent to those skilled in the art upon examination of the examples thereof provided below, which should not be construed as limiting the appended claims.

EXAMPLES

The synthesis of Compounds II through V are summarized in Scheme 1 below:

Scheme I

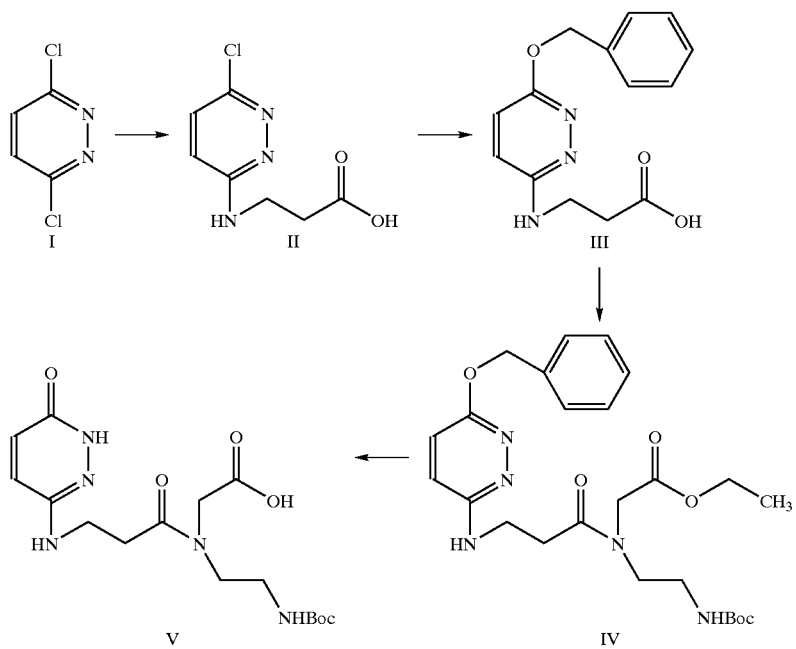

Example 1

N-(3-Chloropyridazin-6-yl)-3-aminopropionic Acid (Compound II)

To a solution of 3,6-dichloropyridazine (50.0 mmol, 7.45 g) and 3-aminopropionic acid (60.0 mmol, 5.34 g) in absolute ethanol (20 mL) was added potassium carbonate (30.0 mmol, 4.15 g), and the suspension was heated to reflux for 3 hours. The mixture was allowed to cool to room temperature, and the light brown solid residue was partitioned between ethyl acetate (300 mL) and water (300 mL). The pH of the aqueous phase was adjusted to 3.5 with 2M aqueous hydrochloric acid, and the yellow solid was filtered and washed with absolute ethanol (10 mL) and diethyl ether (2×20 mL) to give 5.04 g (50%). The product was pure according to TLC Rf 0.31 (dichloromethane/methanol/acetic acid, 85:10:5).

Mp 217–218° C. (decomposed); $^1$H NMR (DMSO-d$_6$): δ 12.24 (bs, 1H, COOH), 7.34 (d, J=9.0 Hz, 1H, aromatic), 7.22 (m, 1H, NH), 6.92 (d, J=9.0 Hz, 1H, aromatic), 3.51 (q, J=6.6 Hz, 2H, (CH$_2$)N), 2.63 (t, J=6.6 Hz, 2H, (CH$_2$)C(O)). $^{13}$C NMR (DMSO-d$_6$): δ 173.08, 158.18, 145.31, 128.59, 118.58, 36.99, 33.34.

Example 2

N-(3-Benzyloxypyridazin-6-yl)-3-aminopropionic Acid (Compound III)

Sodium hydride (22.0 mmol, 0.88 g) was dissolved in benzyl alcohol (10 mL). To the resulting solution was added N-(3-chloropyridazin-6-yl)-3-aminopropionic acid (10.0 mmol, 2.01 g), and the mixture was heated to about 165° C. (oil bath 180° C.) for 3 hours. After cooling to room temperature, water (120 mL) was added, and the aqueous phase was extracted with dichloromethane (3×50 mL). The pH was adjusted to 4.0 with 2M aqueous hydrochloric acid. The light brown precipitate was filtered, washed with water (2×1 mL) and dried over phosphorus pentoxide. The resulting solid was dried to give 1.36 g (47%) of the title compound. The product was pure according to TLC Rf 0.16 (dichloromethane/methanol/acetic acid, 85:10:5).

Mp 258–259° C.; $^1$HNMR (DMSO-d$_6$): δ 12.21 (bs, 1H, COOH), 7.5–7.3 (m, 5H, aromatic), 6.93 (d, J=9.3 Hz, 1H, aromatic), 6.89 (d, J=9.3 Hz, 1H, aromatic), 6.54 (m, 1H, NH), 5.32 (s, 2H, CH$_2$-Ph), 3.47 (t, J=6.6 Hz, 2H, (CH$_2$)N), 2.63 (t, J=6.6 Hz, 2H, (CH$_2$)C(O)); $^{13}$C NMR (DMSO-d$_6$): δ 173.39, 158.60, 156.07, 137.41, 128.39, 128.04, 127.80, 120.71, 119,34, 67.40, 37.25, 33.64; FAB+: 274.1 (M+1).

Example 3

Ethyl N-(2-Boc-aminoethyl)-N-[N'-{(3-benzyloxy)pyridazine-6-yl}-3-aminopropionyl]glycinate (Compound IV)

Ethyl N-(2-Boc-aminoethyl)glycinate (1.80 mmol, 444 mg) was dissolved in dimethyl formamide (12 mL), N-(3-benzyloxypyridazin-6-yl)-3-aminopropionic acid (1.98 mmol, 542 mg) and 3-hydroxy-1,2,3-benzotriazine-4(3H)-one (2.0 mmol, 326 mg) were added. The mixture was cooled in an ice bath, and N,N'-dicyclohexyl-carbodiimide (2.2 mmol, 454 mg) was added. After 1 hour, the ice bath was removed, and the mixture was stirred overnight at room temperature. The mixture was evaporated under vacuum, redissolved in dichloromethane (40 mL) and washed with 5-percent aqueous sodium bicarbonate (2×20 mL). Acetonitrile (10 mL) was added, and the organic phase was evaporated under vacuum. The crude product was purified on a silica column eluted with dichloromethane/methanol (97:3). Fractions containing the product were pooled and evaporated under vacuum to give 0.704 g (78%) of the title compound. The product was pure according to TLC Rf 0.41 (dichloromethane/methanol, 90:10).

$^1$H NMR (CDCl$_3$): δ 7.5–7.3 (m, 5H, aromatic), 6.79 (d, J=9.3 Hz, 1H, aromatic), 6.71 (d, J=9.3 Hz, 1H, aromatic), 5.72 (m, 1H, NH), 5.40 (s, 2H, CH$_2$-Ph), 5.31 (m, 1H, NH), 4.19 (q, J=7.1 Hz, 2H, CH$_2$), 4.01 & 4.06 (s, 2H, O(CH$_2$)-Ph), 3.78 (m, 2H, CH$_2$), 3.50 (m, 2H, CH$_2$), 3.26 (m, 2H, CH$_2$), 2.76 & 2.60 (m, 2H, CH$_2$), 1.41 & 1.39 (s, 9H, Boc); $^{13}$C NMR (CDCl$_3$): δ 173.30 (mi.) & 173.07 (ma.), 170.01, 169.50, 159.34, 155.99 (mi) & 155.70 (ma.), 137.05, 128.40, 128.18, 127.89, 120.70, 119.94, 79.42, 68.37 (ma.) & 68.27 (mi.), 61.76 (mi.) & 61.36 (ma.), 50.49 (mi.) & 49.24 (ma.), 48.75 (ma.) & 47.60 (mi.), 38.96 (ma.) & 38.77 (mi.), 37.80 (mi.) & 37.50 (ma.), 32.05 (mi.) & 31.93 (ma.), 28.36, 14.11; FAB+: 502.3 (M+1).

Example 4

N-(2-Boc-aminoethyl)-N-[N'-(3-oxo-2,3-dihydropyridazin-6-yl)-3-aminopropionyl]glycine (Compound V)

Ethyl N-(2-Boc-aminoethyl)-N-[N'-((3-benzyloxy)pyridazine-6-yl)-3-aminopropionyl]glycinate (0.88 mmol, 440 mg) was suspended in tetrahydrofuran (4.25 mL). The suspension was cooled, and 1M aqueous lithium hydroxide (2.5 mL) was added. After 30 minutes, dichloromethane (6 mL) was added, and the organic phase was extracted with water (6 mL). The pH of the aqueous phase was adjusted to 4.0 by the dropwise addition 2M aqueous hydrochloric acid, and the aqueous phase was extracted with dichloroethane (6 mL). The organic phase was evaporated under vacuum, and redissolved in absolute ethanol (30 mL), and a palladium/carbon catalyst (240 mg) was added. The mixture was hydrogenated for 2 hours and the catalyst was filtered off. The resulting solution was concentrated under reduced pressure then dried under high vacuum to give 333 mg (80%) of the title compound. The product was pure according to TLC Rf 0.07 (dichloromethane/methanol, 80:20).

$^1$H NMR (acetone-d$_6$): δ 7.09 (d, J=9.9 Hz, 1H, aromatic), 6.75 (d, J=9.9 Hz, 1H, aromatic), 6.22 & 6.06 (m, 1H, NH), 5.75 (m, 1H, NH), 4.23 & 4.10 (m, 2H, CH$_2$), 3.46 (m, 2H, CH$_2$), 3.28 & 3.23 (m, 2H, CH$_2$), 2.78 & 2.58 (m, 2H, H$_2$), 1.39 & 1.38 (s, 9H, Boc); FAB+: 384.1 (M+1).

Example 5

Evaluation of Specificity of 3-oxo-2,3-Dihydropyridazine for Thymidine (T-A Base Pair) in a Nucleic Acid Target The synthesis of PNA oligomers including bis-PNA were carried out as illustrated in Egholm, et al., *J. Am. Chem. Soc.*, 1992, 114, 1895–1897 & 9677–9678 also see published PCT Application WO 96/02558 entitled Linked Peptide Nucleic Acids.

To determine the specificity for thymidine in an oligodeoxynucleotide by a PNA oligomer having a 3-oxo-2,3-dihydropyridazine group, a 16-mer oligodeoxynucleotide containing a 10-mer target sequence was prepared and treated with three bis-PNA's having varying groups at two positions of the Hoogsteen strand. The bis-PNA's were prepared having two 10-mer PNA's joined via three consecutive 8-amino-3,6-dioxaoctanoic acid groups. The two 10-mers were joined anti-parallel as shown below. Positions that would normally have a protonated cytosine (as determined by the target sequence) in the Hoogsteen strand are occupied by pseudoisocytosine (J).

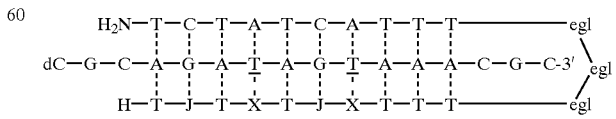

The three bis-PNA's differed only with respect to the groups designated by the variable X in the figure above. The binding of each bis-PNA was measured on a solution ca. 3 µM in PNA and DNA at pH 7.0 in 100 mM NaCl, 10 mM sodium phosphate, 0.1 mM EDTA. Absorption at 260 nm were recorded with 0.5° C. intervals from 5–90° C.

| SEQ ID No. | Oligonucleotide target sequence |
|---|---|
| 1 | 5'-dCGC AGA TAG TAA ACG C-3' |

| SEQ ID No. | Bis-PNA (Tm in ° C.) |
|---|---|
| 2 | X = 3-oxo-2,3-dihydropyridazine (57.0) |
| 3 | X = N-acetyl-N-(2-aminoethyl)glycine (47.5) |
| 7 | X = Guanine (46.0) |

The N-acetyl-N-(2-aminoethyl)glycine group is a null position having no base attached to the backbone. The N-acetyl-N-(2-aminoethyl)glycine group cannot stack or form hydrogen bonds to thymine. Guanine was used as a comparison as it has been reported that guanine interacts with thymine (T) to form fairly stable G:T-A triplets in DNA triple helices (see Best, et al., *J. Am. Chem. Soc.*, 1995, 117, 1187–1193.

The increased Tm is believed to be due to the increased specificity for the thymidine by the 3-oxo-2,3-dihydropyridazine. The increase is considerably higher than that of guanine.

Example 6

Evaluation of Specificity of 3-oxo-2,3-Dihydropyridazine for Cytidine (C-G Base Pair) in a Nucleic Acid Target The synthesis of PNA oligomers including bis-PNA were carried out as illustrated in Egholm, et al., *J. Am. Chem. Soc.*, 1992, 114, 1895–1897 & 9677–9678 also see published PCT Application WO 96/02558 entitled Linked Peptide Nucleic Acids.

To determine the specificity for cytidine in an oligodeoxynucleotide by a PNA oligomer having a 3-oxo-2,3-dihydropyridazine group, a 16-mer oligodeoxynucleotide containing a 10-mer target sequence was prepared and treated with three bis-PNA's having varying groups at two positions of the Hoogsteen strand. The bis-PNA's were prepared having two 10-mer PNA's joined via three consecutive 8-amino-3,6-dioxaoctanoic acid (egl) groups. The two 10-mers were joined in anti-parallel orientation as shown below.

Positions that would normally have a protonated cytosine (as determined by the target sequence) in the Hoogsteen strand are occupied by pseudoisocytosine (represented as "J").

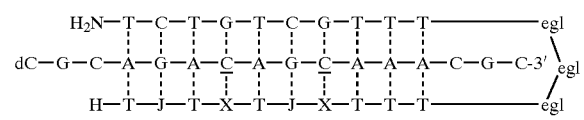

The three bis-PNA's differed only with respect to the groups designated by the variable X in the structure shown above. The binding of each bis-PNA was measured on a solution ca. 3 µM in PNA and DNA at pH 7.0 in 100 mM NaCl, 10 mM sodium phosphate, 0.1 mM EDTA. Absorption at 260 nm were recorded with 0.5° C. intervals from 5–90° C.

| SEQ ID No. | Oligonucleotide target sequence |
|---|---|
| 5 | 5'-dCGC AGA CAG CAA ACG C-3' |

| SEQ ID No. | Bis-PNA (Tm in ° C.) |
|---|---|
| 6 | X = 3-oxo-2,3-dihydropyridazine (42.0; 48.0) |
| 7 | X = N-acetyl-N-(2-aminoethyl)glycine (62.0) |
| 8 | X = Cytidine (61.5) |

The N-acetyl-N-(2-aminoethyl)glycine group is a null position having no base attached to the backbone. The N-acetyl-N-(2-aminoethyl)glycine group cannot stack or form hydrogen bonds to cytidine.

The 3-oxo-2,3-dihydropyridazine was incorporated next to the C-G base pair and compared to a null group and to a cytidine group to see if the increased specificity seen with thymidine (57° C. vs. 47° C. for the null base, Example 5) is seen for cytidine. The effect with cytidine as seen by the large drop in the Tm was destabilizing for the triplex structure. The null base (X=N-acetyl-N-(2-aminoethyl) glycine) and the guanidine group show about the same effect; neither appear to be significantly stabilizing or destabilizing relative to the other.

Example 7

Evaluation of Binding of SEQ ID No. 2 to Nucleic Acid Targets

The binding of a bis PNA (SEQ ID No. 2, Example 5) to 8 different oligodeoxynucleotide target sequences was measured following the procedures illustrated in Example 5. The positions on the oligodeoxynucleotide target sequences that are complementary the two 3-oxo-2,3-dihydropyridazine (hereinafter "ODHP") groups are varied in order to see the effect of a mismatch on the specificity. The target sequences and the resulting Tm's of the triple helix structures formed are shown below.

| SEQ ID No. | Oligodeoxynucleotide target | Tm (° C.) |
|---|---|---|
| 9 | 5'-dCGC AGA TAG TAA ACG C-3' | 57.0 |
| 10 | 5'-dCGC AGA AAG TAA ACG C-3' | 45.0 |
| 11 | 5'-dCGC AGA GAG TAA ACG C-3' | 40.0 |
| 12 | 5'-dCGC AGA CAG TAA ACG C-3' | 40.0 |
| 13 | 5'-dCGC AGA UAG UAA ACG C-3' | 63.5 |
| 14 | 5'-dCGC AGA AAG UAA ACG C-3' | 49.5 |
| 15 | 5'-dCGC AGA GAG UAA ACG C-3' | 44.5 |
| 16 | 5'-dCGC AGA CAG UAA ACG C-3' | 44.5 |

The formation of the ODHP.T-A triplet proved to be highly specific, as indicated by the dramatic decrease in thermal stability when ODHP was positioned opposite to either adenine, guanine or cytosine. The differences in melt temperatures per mismatch (δ Tm per mismatch) relative to thymine (T) control were 12° C. for A; 16.5° C. for G; and 12.0° C. for C. The increased Tm with SEQ ID #13 (which has uracil at both variable positions) is believed to reflect interference from the methyl group present in thymine.

Example 8

Evaluation of Binding of SEQ ID No. 6 to Nucleic Acid Targets

The binding of SEQ ID No. 6 to four different oligodeoxynucleotide target sequences was measured according to the procedures described in Example 5. The positions on the oligodeoxynucleotide target sequences that are complementary to the two 3-oxo-2,3-dihydropyridazine groups were varied in order to see the effect of a mismatch on the specificity. The target sequences and the resulting Tm's of the triple helix structures formed are shown below.

| SEQ ID No. | Oligodeoxynucleotide target | Tm (° C.) |
|---|---|---|
| 17 | 5'-dCGC AGA CAG CAA ACG C-3' | 42.0; 48.0 |
| 18 | 5'-dCGC AGA AAG CAA ACG C-3' | 50.0 |
| 19 | 5'-dCGC AGA GAG CAA ACG C-3' | 50.0 |
| 20 | 5'-dCGC AGA TAG CAA ACG C-3' | 51.0 |

When the 3-oxo-2,3-dihydropyridazine groups are interacting with C-G base pairs there is a strong destabilizing effect as seen by the Tm. This effect is not seen with either the null base, or with the cytidine group in the position complementary to the C-G base pair.

The synthesis of monomer synthons having the formulas VI–VII (Examples 9–15) is shown below:

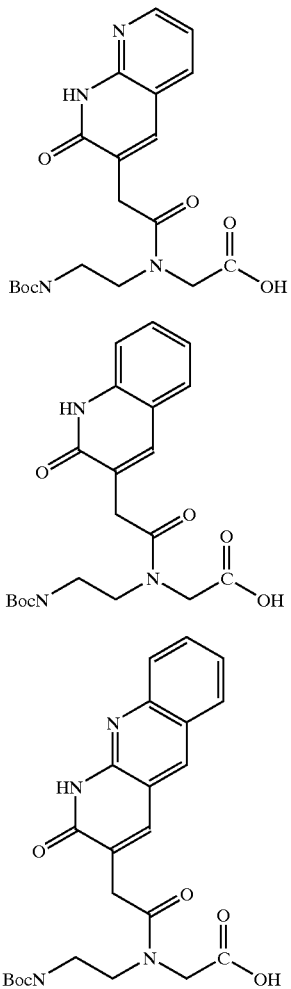

VI

VII

VIII

Example 9

[1,8]Napthyridin-2(1H)-one 3-Acetic Acid

To a solution of THF (30 mL) and LDA (24.4 mmol), cooled to −78° C., was slowly added a solution of di-t-butyl succinate (5.60 g) in THF (4.0 mL). After 15 minutes 3-carbaldehyde-2-pivaloylaminopyridine (2.37 g) dissolved in THF (7 mL) was added. The clear yellow solution was stirred at −78° C. for 15 minutes and then allowed to warm to room temperature. The solution was then poured into saturated aqueous ammonium chloride (200 mL) and extracted with dichloromethane (2×100 mL). The organic phase was dried ($Na_2SO_4$) and evaporated in vacuo. A solution of the diastereomeric alcohols in a 3:1 mixture of 3M aqueous HCl:THF was heated to reflux for 24 hours. After cooling to room temperature the pH was adjusted to 4 and the resulting solid filtered and dried under vacuum to give 1.52 g (65%) of the title compound as a tan colored material.

$^1$H NMR (DMSO-$d_6$): δ 12.19 (bs, 1H, NH), 8.48 (dd, j=4.8, 1.8, 1H), 8.09 (dd, j=7.7, 1.8, 1H), 7.86 (s, 1H), 7.24 (dd, 7.7, 4.7, 1H), 3.48 (s, 2H).

Example 10

Methyl N-(2-Boc-aminoethyl)-N-([1,8]napthyridin-2 (1H)-on-3-yl)acetyl)glycinate

Methyl N-(2-Boc-aminoethyl)glycinate (4.50 mmol) was dissolved in DMF (20 mL) and [1,8]napthyridin-2(1H)-one 3-acetic acid (1.02 g, 5.00 mmol), HOAt (0.68 mL, 5.00 mmol) and DIEA (0.871 mL, 5.0 mmol) were added. After cooling to 0° C. DCC (1.13 g, 5.5 mmol) was added. After 1 hour the ice bath was removed and the mixture was stirred overnight at room temperature. The mixture was evaporated in vacuo, redissolved in ethyl acetate (150 mL) and washed with saturated aqueous $NaHCO_3$ (2×50 mL) followed by water (50 mL). The organic phase was dried ($MgSO_4$) and evaporated in vacuo. The crude product was purified on a silica column eluted with dichloromethane/methanol (9:1, v/v). Fractions containing product were pooled and evaporated in vacuo to give 1.09 g (58%) of the title compound as a tan solid.

$^1$H NMR (DMSO-$d_6$): δ 12.18 (bs, 1H, NH), 8.49–8.47 (m, 1H, aromatic), 7.79–7.76 (s, 1H, aromatic), 7.25–7.22 (m, 1H, aromatic), 6.91–6.75 (t, 1H, NH), 4.37–4.06 (s, 2H, $CH_2$), 3.67–3.48 (s, 2H, $CH_2$), 3.64 (s, 3H, $CH_3O$), 3.49–3.46 (m, 2H, $CH_2$), 3.20–3.15 (M, 2H, $CH_2$), 1.36–1.35 (s, 9H, $CH_3$,(Boc)). $^{13}$C NMR (DMSO-$D_6$): δ 170.32 (170.54), 170.10, 162.61, 155.83, 149.86, 149.31, 136.52 (136.83), 135.87 (135.99), 129.94 (129.64), 118.46, 114.44, 78.05 (77.81), 51.83 (52.21), 48.19, 47.64 (46.69), 38.46 (38.00), 33.49 (33.82), 28.28. FAB$^+$ MS: 419.22 (M+H$^+$, calc. For $C_{20}H_{26}N_4O_6$+H$^+$ 419.19).

Example 11

N-(2-Boc-aminoethyl)-N-([1,8]napthyridin-2(1H)-on-3-yl)acetyl)glycine (Compound VI)

To a solution of methyl N-(2-Boc-aminoethyl)-N-([1,8] napthyridin-2(1H)-on-3-yl)acetyl)glycinate was added 2M aqueous LiOH (6.0 mL, 12.0 mmol). After 20 minutes at room temperature additional water (15 mL) was added and the THF was removed in vacuo. The pH of the aqueous phase was adjusted to 3.0 by addition of 2M HCl. The precipitate was filtered off, washed with water (2×10 mL) and dried in vacuo to give 852 mg (88%) of the title compound as a colorless powder.

$^1$H NMR (DMSO-$d_6$): δ 12.67 (bs, 1H, COOH), 12.20 (BS, 1H, NH), 8.49–8.46 (m, 1H, aromatic), 7.82–7.76 (s, 1H, aromatic), 7.26–7.22 (m, 1H, aromatic), 6.91–6.74 (t, 1H, NH), 4.25–3.98 (s, 2H, $CH_2$), 3.61–3.47 (s, 2H, $CH_2$), 3.47–3.40 (m, 2H, CH$_2$), 3.22–3.02 (m, 2H, CH$_2$), 1.36–1.35 (s, 9H, CH$_3$,(Boc)). $^{13}$C NMR (DMSO-D$_6$): δ 172.58 (172.38), 170.50 (170.14), 162.70, 156.71, 155.75, 155.02, 153.29, 149.89, 136.08, 128.54,128.20, 128.00, 9391, 77.95, 66.49, 52.18 (51.70), 49.65 (49.32), 47.59 (47.37), 33.42, 31.80 (31.42), 28.24 (28.06), 25.40 (24.53), 21.66. FAB$^+$ MS: 405.18 (M+H$^+$, calc. For C$_{19}$H$_{24}$N$_4$O$_6$+H$^+$ 405.18).

Example 12

3-Formyl-2-pivaloylaminoquinoline

To a solution of 2-pivaloylaminoquinoline (5.00 g, 21.92 mmol) in THF (75 mL) at −78° C. was added dropwise BuLi (5.48 mL, 10 M in hexane, 54.80 mmol). After 2 hours at −78° C. the dianion was quenched by the addition of N-formylmorpholine (3.79 g, 37.88 mmol). The reaction mixture was allowed to warm to room temperature and poured into 2M aqueous HCl (20 mL). The pH of the aqueous phase was adjusted to 7.0 by addition of 2M HCl and the aqueous phase was diluted with water (100 mL) and extracted with diethyl ether (2×100 mL). The organic phase was dried (MgSO$_4$) and evaporated to dryness in vacuo. The crude product was recrystallized from petrol ether/ethyl acetate to give 2.92 g (52%) of the title compound.
$^1$H NMR (DMSO-d$_6$): δ 10.70 (bs, 1H, NH), 9.82 (s, 1H, CHO), 8.85 (s, 1H, aromatic), 8.19–8.17 (m, 1H, aromatic), 7.97–7.95 (m, 1H, aromatic), 7.91–7.87 (m, 1H, aromatic), 7.76–7.62 (m, 1H, aromatic), 1.30 (s, 9H, CH$_3$). $^{13}$C NMR (DMSO-D$_6$): δ 189.62, 189.55, 178.37, 149.66, 148.15, 140.33, 132.77, 129.82, 127.51, 126.59, 125.48, 123.64, 26.97. FAB$^+$ MS: 257.05 (M+1, calc. For C$_{15}$H$_{16}$N$_2$O$_2$+H$^+$ 257.13) and 279.04 (M+Na$^+$, calc. for C$_{15}$H$_{16}$N$_2$O$_2$+Na$^+$ 279.11).

Example 13

Benzo[b][1,8]napthyridin-2(1H)-one 3 Acetic Acid

To a solution of THF (15 mL) and LDA (2M in THF, 15.9 mmol, 7.95 mL), cooled to −78° C., was slowly added a solution of di-t-butyl succinate (15.9 mmol, 3.28 g) in THF (3.0 mL). After 15 minutes at −78° C. 3-Formyl-2-pivaloylaminoquinoline (1.92 g, 7.50 mmol) dissolved in THF (10 mL) was added. The clear yellow solution was stirred at −78° C. for 15 minutes and then allowed to warm to room temperature. The solution was poured into saturated aqueous ammonium chloride (200 mL) and extracted with dichloromethane (2×100 mL). The organic phase was dried (MgSO$_4$) and evaporated in vacuo. The crude product of diastereomeric alcohols was heated to reflux for 24 hours in a mixture of THF (5 mL) and HCl (3M, aqueous) and then poured into water (100 mL) and neutralized with K$_2$CO$_3$. The tan precipitate was washed with water (2×25 mL) and dried in vacuo overnight. The crude product (1.60 g) was heated in acetonitrile (50 mL) and filtered while hot. The product was washed with ether (2×25 mL) and dried in vacuo to give 1.50 g (79%) of a material judged to be 61% pure according to HPLC (260 nm).

Example 14

Methyl N-(Benzo[b][1,8]napthyridin-2(1H)-one 3-yl)-N-(2-boc-aminoethyl)glycinate Methyl N-(2-Boc-aminoethyl)glycinate (0.812 g, 3.5 mmol) was dissolved in DMF (10 mL) and benzo[b][1,8]napthyridin-2(1H)-one 3 acetic acid (883 mg, 3.5 mmol) was added. The mixture was cooled in an ice bath and HBTU (1.52 g, 4.0 mmol) was added. After 1 hour the ice bath was removed and the mixture was stirred overnight at room temperature. The mixture was evaporated in vacuo, redissolved in dichloromethane (100 mL) and washed with saturated aqueous NaHCO$_3$ (2×50 mL). The organic phase was dried (MgSO$_4$) and evaporated in vacuo. The crude product was purified on a silica column eluted with dichloromethane/methanol (97:3, v/v). Fractions containing the product were pooled and evaporated in vacuo to give 345 mg (21%) of the title compound as a tan solid.
$^1$H NMR (DMSO-d$_6$): δ 12.13 (bs, 1H, NH), 8.70–8.65 (m, 1H, aromatic), 7.91 (s, 1H, aromatic), 7.88 (s, 1H, aromatic), 7.79–7.75 (m, 1H, aromatic), 7.55–7.49 (m, 1H, aromatic), 6.90–6.72 (bs, 1H, NH), 4.36–4.05 (s, 2H, CH$_2$), 4.11 (q, J=, 2H, CH$_2$), 3.67–3.33 (s, 2H, CH$_2$), 3.48–3.53 (m, 2H, CH$_2$), 3.27–3.04 (m, 2H, CH$_2$), 1.35 (s, 9H, CH$_3$ (Boc)). $^{13}$C NMR (DMSO-D$_6$): δ 170.17 (170.32), 170.01 (170.39), 163.08 (163.17), 155.75 (155.63), 148.67, 147.02, 136.20 (136.46), 136.07 (136.13), 131.17, 130.16 (129.88), 128.67, 126.90, 124.85 (124.67), 115.67 (115.63), 78.00 (77.76), 51.81 (52.20), 48.18 (48.38), 47.63, 38.43 (38.29), 33.56 (33.87), 28.26. FAB$^+$ MS: 469.10 (M+H$^+$, calc. For C$_{24}$H$_{28}$N$_4$O$_6$+H$^+$ 469.21).

Example 15

N-(Benzo[b][1,8]napthyridin-2(1H)-on-3-yl)acetyl)-N-(2-boc-aminoethyl)glycine (Compound VIII)

To a solution of Methyl N-(benzo[b][1,8]napthyridin-2 (1H)-one 3-yl)-N-(2-Boc-aminoethyl)glycinate (0.426 mmol, 200 mg) in THF (4.0 mL) was added 2M aqueous (1.07 mL, 2.14 mmol). After 15 minutes at room temperature additional water (7.0 mL) was added and the THF was removed in vacuo. The aqueous phase was extracted with dichloromethane (2×2 mL) and the pH was adjusted to 3.0 by the addition of 2M aqueous HCl. The precipitate formed was filtered off, washed with water (2×5 mL) and dried in vacuo to give 176 mg (91%) of the title compound as a tan powder.
FAB$^-$ MS: 453.42 (M−H$^+$, calc. For C$_{34}$H$_{26}$N$_4$O$_6$−H$^+$ 453.18).

Example 16

Methyl N-(2-Boc-aminoethyl)-N-(quinolin-2(1H)-on-3-yl)acetyl)glycinate

Ethyl N-(2-Boc-aminoethyl)glycinate (443 mg, 1.8 mmol) was dissolved in DMF (10 mL) and quinolin-2(1H)-one-3-acetic acid (prepared as per the procedure of Shanmugam, P., *Naturforsch*, 1973, 196, 551–553) (406 mg, 2.0 mmol) and HOAt (272 mg, 2.0 mmol) was added. The mixture was cooled on ice and DCC (413 g, 2.0 mmol) was added. After 1 hour the ice bath was removed and the mixture was stirred overnight at room temperature. The mixture was evaporated in vacuo, redissolved in ethyl acetate (100 mL) and washed with saturated aqueous NaHCO$_3$ (2×30 mL) followed by water (30 mL). The organic phase was dried (MgSO$_4$) and evaporated in vacuo. The crude product was purified on a silica column eluted with dichloromethane/methanol (9:1, v/v). Fractions containing the product were pooled and evaporated in vacuo to give 476 mg (60%) of the title compound as a tan solid.

Example 17

N-(2-Boc-aminoethyl)-N-(quinolin-2(1H)-on-3-yl) acetyl)glycine (Compound VII)

To a solution of methyl N-(2-Boc-aminoethyl)-N-(quinolin-2(1H)-on-3-yl)acetyl)glycinate (427 mg, 0.99 mmol) in THF (10 mL) was added 2M aqueous LiOH (2.5 mL, 5 mmol). After 20 minutes at room temperature additional water (10 mL) was added. The THF was evaporated in vacuo and 2M aqueous HCl (2.5 mL) was added with vigorous stirring. The precipitate was filtered off, washed with water (2×10 mL) and dried in vacuo to give 280 mg (74%) of the title compound as a colorless powder.

$^1$H NMR (DMSO-d$_6$): δ 11.77 (bs, 1H, NH), 781 (7.74) (s, 1H, aromatic), 7.64–7.13 (m, 4H, aromatic), 6.95–6.65 (m, 1H, NH), 3.98 (4.25) (s, 2H, CH$_2$) 3.59 (3.45) 3.30–3.00 (m, 4H, 2×CH$_2$), 1.37 (1.35) (s, 9H, CH$_3$ (Boc)).

Example 18

Ethyl N-[(2-Hydroxy-10-H-pyrimido[5,4-b][1,4] benzothiazin-1-yl)acetyl]-N-(2-boc-aminoethyl) glycinate

2-Hydroxy-10-H-pyrimido[5,4-b][1,4]benzothiazin (653 mg, 3.0 mmol) was suspended in DMF (30 mL) and NaH (60% in mineral oil, 132 mg, 3.3 mmol) was added in one portion. After 15 minutes ethyl N-bromoacetyl-N-(2-Boc-aminoethyl)-glycinate (1.10 g, 3.3 mmol) was added. The mixture was stirred at room temperature for 2 hours, evaporated in vacuo, redissolved in dichloromethane (200 mL) and washed once with saturated aqueous NaHCO$_3$ (100 mL) and once with saturated aqueous NaCl. The mixture was dried (MgSO$_4$) and evaporated to dryness in vacuo. The crude material was purified on a silica gel column using methanol/dichloromethane (1:9, v/v) as the eluent to give 853 mg (57%) of the title compound.

$^1$H NMR (DMSO-d$_6$): δ 10.37 (bs, 1H, NH), 7.51 (s, 1H, H-6), 7.09–7.05 (m, 2H, aromatic), 6.94–6.75 (m, 3H, aromatic+NH), 4.66–4.48 (s, 2H, CH$_2$), 4.30–4.04 (s, 2H, CH$_2$), 4.18–4.08 (q, 2H, CH$_2$), 3.41 (m, 2H, CH$_2$), 3.20–3.03 (m, 2H, CH$_2$), 1.38–1.37 (s, 9H, CH$_3$ (Boc)), 1.24–1.18 (t, 3H, CH$_3$). $^{13}$-NMR (DMSO-D$_6$): δ 169.44+169.09, 167.87+167.58, 160.15, 155.82, 154.58, 141.23, 136.50, 127.49, 126.09, 124.01, 116.97, 115.83+115.76, 93.39, 78.13+77.85, 61.22+60.61, 49.26+49.02, 48.01, 47.09, 38.33, 28.25, 14.109. FAB$^+$ MS: 503.18 (M+H$^+$, calc. For C$_{23}$H$_{29}$N$_5$O$_6$S+H$^+$ 504.19).

Example 19

N-[(2-Hydroxy-10-H-pyrimido[5,4-b][1,4] benzothiazin-1-yl)acetyl]-N-(2-boc-aminoethyl) glycine

Ethyl N-[(2-hydroxy-10-H-pyrimido[5,4-b][1,4]-benzothiazin-1-yl)acetyl]-N-(2-Boc-aminoethyl)glycinate (201 mg, 0.4 mmol) was dissolved in THF (10 mL) and LiOH (2M, aqueous, 1.0 mL) was added. After 15 minutes at room temperature water (10 mL) was added, the THF was evaporated in vacuo and HCl (2M, aqueous, 1.0 mL) was added with vigorous stirring. The solid yellow material was filtered off and dried in vacuo to give 173 mg (91%) of the title compound.

$^1$H NMR (DMSO-d$_6$): δ 10.37 (bs, 1H, NH), 7.51 (s, 1H, H-6), 7.09–7.05 (m, 2H, aromatic), 6.94–6.75 (m, 3H, aromatic+NH), 4.66–4.48 (s, 2H, CH$_2$), 4.30–4.04 (s, 2H, CH$_2$), 3.41 (m, 2H, CH$_2$), 3.20–3.03 (m, 2H, CH$_2$), 1.38–1.37 (s, 9H, CH$_3$ (Boc)). FAB$^+$ MS: 476.23 (M+H$^+$, calc. For C$_{21}$H$_{25}$N$_5$O$_6$S+H$^+$ 476.16).

Example 20

Hybridization of PNA 10 Mers Having N-(Benzo[b][1,8]napthyridin-2(1H)-on-3-yl)acetyl)-N-(2-boc-aminoethyl)glycine Monomers at Selected Positions to PNA and DNA Target Sequences

The hybridization of PNA 10 mers having 0, 1, or 3 tricyclic N-(benzo[b][1,8]napthyridin-2(1H)-on-3-yl) acetyl)-N-(2-Boc-aminoethyl)glycine monomers (Example 15) incorporated at selected positions was measured against both PNA (SEQ ID No. 21) and DNA (SEQ ID No. 22) target sequences. The PNA sequences were prepared as illustrated in Egholm, supra.

The three PNA's differed only with respect to the groups designated by the variable bT in Table below. The binding of each PNA was measured in a solution ca. 3 μM in PNA and DNA or PNA and PNA at pH 7.0 in 100 mM NaCl, 10 mM sodium phosphate, 0.1 mM EDTA. Absorption at 260 nm were recorded at 0.5° C. intervals from 5–90° C.

| SEQ ID No. | Target sequence | |
|---|---|---|
| 21 | H-AGTGATCTAC-Lys-NH$_2$ | (PNA) |
| 22 | 5'-dAGTGATCTAC-3' | (DNA) |

| SEQ ID No. | PNA SEQUENCE | Tm (° C.) DNA/PNA | Tm (° C.) DNA/PNA |
|---|---|---|---|
| 23 | H-GTAGATCACT-Lys-NH$_2$ | 51.0/68.5 | — |
| 24 | H-GTAGA(E1)CACT-Lys-NH$_2$ | 51.0/68.0 | 0.0/0.5 |
| 25 | H-G(E1)AGA(E1)CAC(E1)-Lys-NH$_2$ | 59.0/68.0 | 8.0/0.5 |

Each variable (E1) is an incorporated N-[b][1,8] napthyridin-2(1H)-on-3-yl)acetyl)-N-(2-Boc-aminoethyl) glycine monomer. The effect of N-(benzo[b][1,8] napthyridin-2(1H)-on-3-yl)acetyl)-N-(2-Boc-aminoethyl) glycine monomers in a PNA-PNA duplex is null, e.g. not destabilizing. The effect of the three tricyclic monomers in the PNA oligomer has a significant effect on the interaction with the DNA target resulting in an 8° C. increase in Tm.

Examples 21–39

3-Formyl-6-methyl-2-(pivaloylamino)pyridine and 3-Formyl-5-methyl-2-(pivaloylamino)pyridine were prepared according to Turner, J. A. *J. Org. Chem.* 1990, 55, 4744–4750. Methyl-N-(2-Boc-aminoethyl)glycinate was prepared according to Dueholm et al., *Org. Prep. and Proc. Int.*, 1993, 25, 457–461. The following chemicals were used as received: butyllthium (2.5 M in hexanes, Aldrich 23,071-5), dicyclohexylcarbodiimide (DCC) (Aldrich D,000-2), diisopropylamine (Aldrich 11,001-9) and 3-hydroxy-1,2,3-benzotriazin-4(3H)-one (DhbtOH) (Aldrich 32,796-4).

Di-tert-butyl succinate was prepared by adding succinic acid chloride (61 g, 0.40 mol) dropwise to a refluxing mixture of dimethylaniline (0,84 mol, 101 g), tert-butylalcohol (57 g, 0.75 mol) and diethyl ether (200 mL). The resulting solution was stirred under reflux for 2 h and quenched by addition of water (200 mL). The organic phase was separated, extracted twice with 10% H$_2$SO$_4$ (25 mL) and NaHCO$_3$ (100 mL), dried (MgSO$_4$) and evaporated to an oil in vacuo. Kugelrohr destillation (116° C., 16 mmHg) afforded the desired product (11 g, 22%) as a white low melting solid. $^1$H NMR (CDCl$_3$): 2.48 (s, 4H, CH$_2$), 1.45 (s, 18H, CH$_3$). $^{13}$C NMR (CDCl$_3$): 171.59, 80.50, 30.61, 28.08.

Phosphoramidites for nucleic acid synthesis were obtained from CruaChem. TLC was performed on silica 60 (Merck 5554 aluminium sheet), column chromatograpy on silica 60 (230–400 mesh ASTM) (Merck 9385). $^1$H and $^{13}$C nmr spectra were obtained at either 250 MHz (Bruker AMX 250) or at 400 MHz (Varian Unity 400) in 5 mm tubes; chemical shifts are positive in the low-field direction. FAB mass spectra were recorded on a Jeol Hx110/110 mass spectrometer. All PNA oligomers were characterised MALDI-TOF mass spectroscopy recorded on a Kratos Compact MALDI II instrument operating in the positive ion mode, using 3,5-dimethoxy-4-hydroxycinnamic acid as the matrix. $T_m$ values were obtained on a Gilford Response spectrophotometer and measured on solutions ca. 3 μM in PNA and DNA at pH 7.0 in 100 mM NaCl, 10 mM $Na_2HPO_4$, 0.1 mM EDTA; absorptions at 260 nm were recorded with 0.5° C. intervals from 5–90° C. PNA oligomerization was performed as previously described in Dueholm supra. DNA oligomerization was performed according to standard protocols on a MilliGen/Biosearch 8700 DNA synthesizer. PNA sequences were prepared as illustrated in Egholm, supra.

The preparation of the monomer synthon having the formula IX is shown below (Examples 21–39):

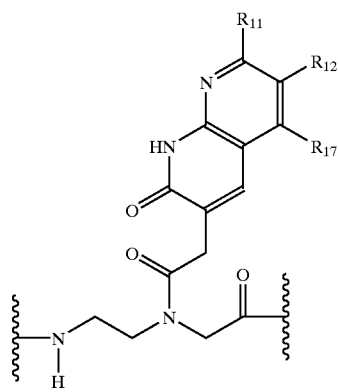

IX wherein:

| Monomer | R11 | R12 | R17 |
|---|---|---|---|
| E1 (bT) | H | H | H |
| E2 (7-Cl-bT) | Cl | H | H |
| E3 (6-Cl-bT) | H | Cl | H |
| E4 (7-CH₃-bT) | CH₃ | H | H |
| E5 (6-CH₃-bT) | H | CH₃ | H |
| E6 (5-CH₃-bT) | H | H | CH₃ |

Inhibition of gene expression by antisense and antigene approaches relies on efficient specific targeting of single and double stranded nucleic acids under physiological conditions. Efficient triplex targeting of dsDNA by oligonucleotides is dependent on protonation of the cytosine N3, and consequently a large number of nucleobases have been synthesized and evluated in order to eliminate this pH dependence. The most successful members of this class of nucleobases are the 5-methylcylosine, [1]pseudoisocytosine[2] and 8-oxoadenine. While 5-methylcytosine represents a class of mimics of cytosine where the basicity of the N3 is increased as a result of the C-5 substituent, pseudoisocytosine and 8-oxoadenine are "permanently protonised" analogues of cytosine and therefore able to form triplex structures, virtually independent of pH.

In some preferred embodiments, the present invention provides PNA containing a 1,8-naphthridin-2,7-(I,8H)-dione nucleobase, which has an extended aromatic surface area, as well as the ability to mimic the function of protonated cytosine.

In the following examples, duplex recognition properties of the 1,8-naphthyridine-2(1H)-one heterocyclic systems was assessed by incorporation of the monomers E1–E6 into 10-mer oligomers of PNA in isolated as well as adjacent sites. Duplexes of these PNA's with DNA, PNA and RNA targets were designed as to have adenine facing the 1,8-naphthyridine-2(1H)-one units in otherwise Watson-Crick complementary PNA-DNA, PNA-PNA, or PNA-RNA oligomeric recognition systems. The thermal stability of complexes containing differently substituted 1,8-naphthyridine-2(1H)-one units was compared to that of the corresponding unsubstituted 1,8-naphthyridine-2(1H)-one and to a thymine containing control.

The preparation of Compounds E1–6 are shown generally in Scheme 2 below:

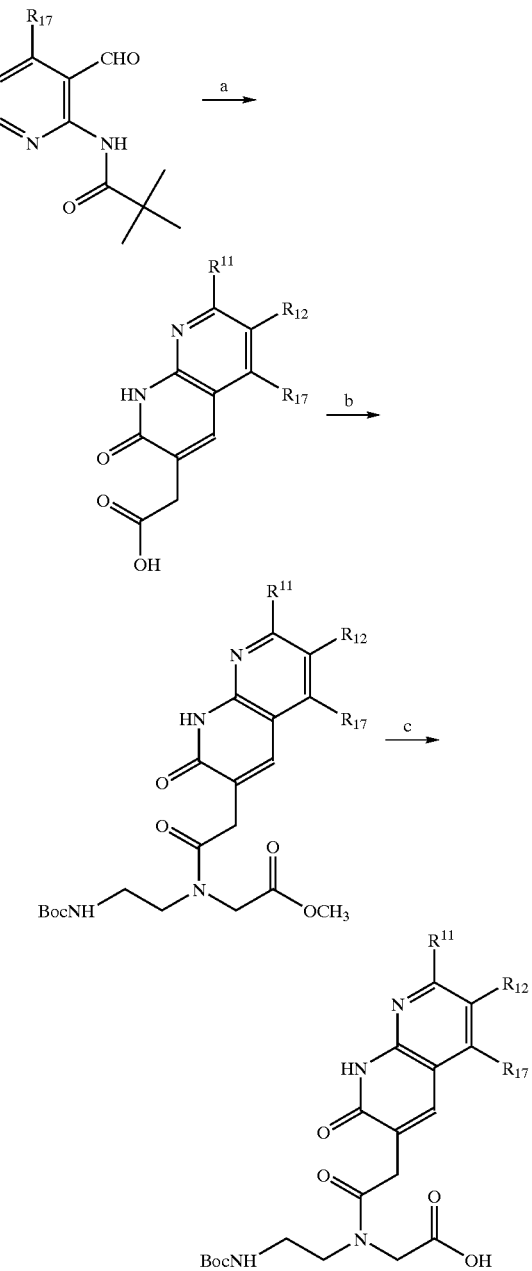

(a) Preformed enolate of di-tert-butylsuccinated using LDA and di-tert-butylsuccinate in diethyl ether at −78° C., was added to a precooled solution (−78° C.) of the starting compound in THF, initially stirred at −78° C. and then at room temperature; the crude product from this reaction was treated with 3M aqueous HCl at reflux; (b)Methyl N-(2Boc-aminoethyl)glycinate, DhbtOH and DCC; or HBTU in DMF at room temperature overnight; (c) 2M LiOH in THF at room temperature.

Example 21

6-Amino-2-(pivaloylamino)pyridine

To a solution of 2,6-diaminopyridine (50.0 g, 0.46 mol) in dioxane (250 mL) was added slowly (1 h) pivaloylchloride (27.9 g, 0.23 mol), dissolved in dioxane (50 mL). The resulting mixture was stirred for 2 h and the white precipitate (2,6-diaminopyridine hydrochloride) filtered off. The organic phase was evaporated to dryness in vacuo, and the crude product recrystalized from n-hexane/ethyl acetate to give the desired product (32.83 g, 74%) as colorless crystals (mp 140–141° C.). $^1$H NMR (DMSO-d$_6$): δ 8.93 (s, 1H), 7.34 (t, 7.9 Hz, 1H), 7.19 (d, 7.6 Hz, 1H), 6.18 (d, 7.6 Hz, 1H), 5.75 (br. s, 2H), 1.19 (s, 9H). $^{13}$C NMR (DMSO-d$_6$): δ 176.5, 158.5, 150.4, 138.4, 103.6, 101.5, 39.4, 27.1. FAB$^+$ MS (m/z): 193.88 M+H$^+$, calc. for C$_{10}$H$_{15}$N$_3$O+H$^+$ 194.1293.

Example 22

6-Chloro-2-(pivaloylamino)pyridine

To a precooled (−10° C.) suspension of 6-amino-2-(pivaloylamino)pyridine (28.00 g, 0.145 mol) in conc. aqueous HCl (150 mL) was added potassium nitrite (14.81 g, 0.174 mol) dissolved in water (8 mL) over a 1.5 h period. The resulting reaction mixture was stirred for 5 h at −10° C. under nirogen, before ajustment of the pH to 9 by addition of conc. aqueous NaOH. The aqueous solution was extracted with ethyl acetate (3×100 mL) and the organic fractions washed with 2M NaOH (3×40 mL). The organic phase was dried (MgSO$_4$), evaporated in vacuo and recrystallised from n-hexane/ethyl acetae to give the desired product (17,70 g (58%) as a white powder (m.p. 86–87° C.). $^1$H NMR (DMSO-d$_6$): δ 10.08 (s br, 1H), 8.04 (d, 8.1 Hz, 1H), 7.81 (t, 8.1 Hz, 1H), 7.17 (d, 8.1 Hz, 1H), 1.22 (s, 9H). $^{13}$C NMR (DMSO-d$_6$): δ 177.4, 152.5, 147.8, 141.4, 119.0, 112.8, 39.4, 26.8. FAB$^+$ MS (m/z): 213.06 M+H$^+$, calc. for C$_{10}$H$_{13}$ClN$_2$O+H$^+$ 213.0795.

Example 23

(7-Chloro-1,8-naphtpyridin-2(1H)-oxo-3-yl)acetic Acid

To a precooled (−78° C.) solution of diisopropylamine (22.03 g, 100 mmol) in diethylether (150 mL) was added BuLi (2.5 M in hexanes) (40 mL, 100 mmol), the solution was stirred at this temperature for 15 min before slow addition of di-tert-butyl succinate (10.83 g, 50.0 mmol) dissolved in diethylether (20 mL). After 20 min at −78° C., 6-chloro-3-formyl-2-(pivaloylamino)pyridine (Turner, J. A., J. Org. Chem., 1990, 55, 4744–4750) (11.32 g, 50.0 mmol) dissolved in dry THF (20 mL, LAB-SCAN C2520, dried over molecular seives) was added slowly. The yellow solution was stirred at −78° C. for 30 min and then allowed to warm to rt. The solution was then poured into NH$_4$Cl (sat., aqueous) (200 mL) and the aqueous layer was separated and extracted twice with diethylether (2×100 mL). The combined organic layers were washed once with water (100 mL) and once with brine (100 mL), dried over MgSO$_4$ and evaporated in vacuo. The crude products of diastereomeric alcohols were dissolved in dioxane (150 mL) and HCl (3M, aqueous) (150 mL) and refluxed for 6 h. The resulting yellow precipitate was filtered off, washed once with water and once with diethylether and dried in vacuo to give the desired product as a yellow solid (10.91 g, 89%). $^1$H NMR (DMSO-d$_6$): δ 12.43 (s, 1H, COOH), 8.12 (d, 8.1 Hz, 1H, arom.), 7.87 (s, 1H, arom.), 7.29 (d, 8.1 Hz, 1H, arom.), 3.55 (s, 2H, CH$_2$). $^{13}$C NMR (DMSO-d$_6$): δ 171.7, 162.6, 149.9, 149.1, 139.3, 136.4, 129.6, 118.4, 113.5, 35.6. FAB$^+$ MS (m/z): 239.04, M+H$^+$, calc. for C$_{10}$H$_7$ClN$_2$O$_3$+H$^+$ 239.0223. Anal. calc. for C$_{10}$H$_7$ClN$_2$O$_3$: C, 50.33, H, 2.96, N, 11.74. Found: C, 50.49, H, 2.98, N, 11.96.

Example 24

Methyl N-(2-(tert-Butyloxycarbonyl)-aminoethyl)-N-(7-chloro-1,8-naphthyridine-2(1H)-oxo-3-yl) acetylglycinate (7-chloro-1,8-naphtphyridin-2(1H)-oxo-3-yl)acetic acid (0.50 g, 2.10 mmol) and DhbtOH (0.34 g, 2.10 mmol) was dissolved in dry DMF (15 mL). The mixture was cooled on ice and DCC (0.43 g, 2.10 mmol) was added and stirred for 40 min. Methyl N-(2-tert-butyloxycarbonyl)aminoethyl) glycinate (0.46 g, 2.10 mmol) dissolved in DMF (5 mL) was added. After 1 h the ice bath was removed and the mixture was stirred overnight at rt. The mixture was evaporated in vacuo, redissolved in EtOAc (25 mL), filtered and washed with NaHCO$_3$ (5%, aqueous) (3×25 mL) and with brine (2×25 mL) The organic phase was dried (MgSO$_4$), filtered and evaporated in vacuo. The crude product was purified on a silica column eluted with dichloromethane/methanol (9:1 v/v). Fractions containing the product were evaporated in vacuo to yield the desired product (0.61 g, 64%) as a slightly yellow solid (mp 68–69° C.). $^1$H NMR (DMSO-d$_6$; this compound exist as two rotamers; chemical shifts for the minor rotamer is given in brackets): δ 12.45 (br. s, 1H, NH), 8.11 (8.16) (d, 8.1 Hz, 1H, arom.), 7.79 (7.81) (s, 1H, arom.), 7.32 (d, 8.1 Hz, 1H, arom.), 6.91 (6.81) (m, 1H, NH), 4.05 (4.36) (s, 2H, CH$_2$), 3.68 (3.67) (s, 2H, CH$_2$), 3.64 (s, 3H, CH$_3$O), 3.49–3.42 (m, 2H, CH$_2$), 3.20–3.15 (3.05–3.00) (m, 2H, CH$_2$), 1.36 (1.35) (s, 9H, CH$_3$ (Boc)). $^{13}$C NMR (DMSO-d$_6$): δ 170.33, 170.08, 162.39 (162.48), 155.77, 149.72, 149.04, 139.06, 135.89 (136.16), 130.29 (130.00), 118.32, 113.45, 78.01, 51.79 (52.20), 47.61 (48.15), 38.43, 33.45 (33.78), 28.25. FAB$^+$ MS (m/z): 453.1553 (M+H$^+$, calc. for C$_{20}$H$_{25}$N$_4$O$_6$Cl+H$^+$ 453.1540).

Example 25

N-2-((tert-Butyloxycarbonyl)-aminoethyl)-N-(7-chloro-1,8-naphthyridine-2(1H)-oxo-3-yl) acetylglycine Methyl N-(2-(tert-butyloxycarbonyl)-aminoethyl)-N-(7-choro-1,8-naphthyridine-2(1H)-oxo-3-yl)acetylglycine (0.607 g, 1.34 mmol) was dissolved in THF (10 mL, LAB-SCAN C2520, dried over molecular seives) and LiOH (0.428 M, aqueous) (6.90 mL, 2.95 mmol) was added. After 30 min at rt. additional water (10 mL) was added and the THF was removed in vacuo. The pH of the aqueous solution was adjusted to 3.0 by addition of HCl (2M, aqueous). The white precipitate was filtered off, washed with water (2×10 mL) and dried in vacuo to give the product (355 mg, 60%) as a slightly yellow powder (mp 176–78° C.). $^1$H NMR (DMSO-d$_6$; this compound exist as two rotamers; chemical shifts for the minor rotamer is given in brackets): δ 12.42 (br. s, 1H, COOH), 8.07 (8.14) (d, 8.1 Hz, 1H, arom.), 7.84 (7.78) (s, 1H, arom.), 7.30 (d, 8.1 Hz, 1H, arom.), 6.88 (6,71) (m, 1H, NH), 3.97 (4.23) (s, 2H, CH$_2$), 3.61 (s, 2H, CH$_2$), 3.47–3.43 (3.33–3.30) (m, 2H, CH$_2$), 3.19–3.16 (3.05–3.03) (m, 2H, CH$_2$), 1.36 (1.34) (s, 9H, CH$_3$ (Boc)). $^{13}$C NMR (DMSO-d$_6$): δ 170.92 (171.21), 169.88 (170.22), 162.37 (162.46), 155.74, 149.67, 149.00, 138.95 (139.13), 135.82 (136.06), 130.35 (130.00), 118.28, 113.45 (113.51), 77.99 (77.75), 48.10 (50.29), 47.57 (46.75), 38.41 (37.97), (33.75) 33.51, 28.27. FAB$^+$ MS (m/z): 439.1371 (M+H+, calc. for C$_{19}$H$_{23}$N$_4$O$_6$Cl+H$^+$ 439.1384).

Example 26

(7-Methyl-1,8-naphthyridin-2-on-3-yl)acetic Acid

To a precooled (−78° C.) solution of N,N-diisopropylamine (4.84 g, 48.0 mmol) in diethyl ether (125 mL, dried over molecular seives) was added BuLi (2.5 M in hexanes) (19.0 mL, 48.0 mmol), the solution was stirred at this temperature for 15 min before slow addition of di-tert-butyl succinate (5.75 g, 0.0250 mol) dissolved in diethylether (10 mL). After 20 min at −78° C., 3-formyl-6-chloro-2-(pivaloylamino)pyridine (5.00 g, 23.0 mmol) dissolved in dry THF (10 mL, LAB-SCAN C2520, dried over molecular seives) was slowly added. The resulting yellow solution was stirred at −78° C. for 30 min and then allowed to warm to rt. The solution was then poured into NH$_4$Cl (sat., aqueous) (100 mL). The aqueous layer was separated and extracted with diethyl ether (3×50 mL, dried over molecular seives). The combined organic layers were washed once with water (50 mL) and once with brine (50 mL), dried over MgSO$_4$, and evaporated in vacuo. The crude products of diastereomeric alcohols were dissolved in HCl (3M, aqueous) (80 mL) and refluxed for 3.5 h. The aqueous phase was washed with diethyl ether (3×75 mL, dried over molecular seives), with chloroform (3×50 mL) and then adjusted to pH 7 by addition of K$_2$CO$_3$. The resulting yellow precipitate was filtered off, washed once with water and once with diethylether and dried in vacuo to give the desired product (1.25 g, 27%) as a yellow solid. mp. >250° C. $^1$H NMR (D$_2$O/NaOH; this compound exist as two rotamers; chemical shifts for the minor rotamer is given in brackets): δ 7.53 (d, 8.1 Hz, 1H), 7.31 (s, 1H), 6.69 (d, 8.1 Hz, 1H), 3.20 (s, 2H), 2.25 (s, 3H). $^{13}$C NMR (D$_2$O/NaOH): δ 180.4, 172.1, 159.0, 155.7, 136.5, 135.9, 126.6, 116.6, 114.8, 39.6, 23.3. FAB$^+$ MS (m/z): 218.0768 (M+H$^+$, calc. for C$_{11}$H$_{10}$N$_2$O$_3$+H$^+$ 219.0770).

Example 27

Methyl N-((7-Methyl-1,8-naphthyridin-2(1H)-on-3-yl)acetyl)-N-(2-(tert-butyloxycarbonyl)aminoethyl) glycinate To a precooled (0° C.) solution of (7-methyl-1,8-naphthyridin-2(1H)-on-3-yl)acetic acid (0.995 g, 4.60 mmol) and DhbtOH (0.744 g, 4.60 mmol) in DMF (25 mL)was added DCC (1.04 g, 5.00 mmol) and the mixture was stirred for 40 min at 0° before addition of ethyl N-(2-(tert-butyloxycarbonyl)aminoethyl)glycinate (1.10 g, 5.0 mmol). This mixture was stirred at rt overnight, evaporated in vacuo, redissolved in ethyl acetate (75 mL) and washed with 5% aqueous NaHCO$_3$ (3×25 mL) and with brine (2×25 mL). The organic phase was dried over MgSO$_4$, filtered and evaporated in vacuo. The crude product purified on silica using dichloromethane/methanol (90:10 v/v) as the eluent. Fractions containing the product were pooled and evaporated in vacuo to yield the desired product (790 mg, 41%) (mp 98–100° C.). $^1$H NMR (DMSO-d$_6$; this compound exist as two rotamers; chemical shifts for the minor rotamer is given in brackets): δ 12.05 (s br, 1H), 7.91 (7.96) (d, 8.0 Hz, 1H), 7.74 (7.71) (s, 1H), 7.10 (d, 8.0 Hz, 1H), 6.90 (6.99) (m, 1H), 4.05 (4.36) (s, 2H), 4.09 (q, J=5.2 Hz, 3H), 3.63 (s, 3H), 3.47 (m, 2H), 3.17 (s, 2H), 3.16 (s, 3H), 1.36 (1.35) (s, 9H). $^{13}$C NMR (DMSO-d$_6$): δ 170.44 (170.66), 170.11, 162.65 (162.73), 159.22, 155.83 (155.71), 148.99, 136.43 (136.77), 136.04 (136.17), 128.61 (128.29), 118.21, 112.00 (112.07), 78.04, 51.81 (52.20), 47.63 (48.20), 38.59 (38.45), 33.42 (33.75), 28.27, 24.22. FAB$^+$ HRMS: 433.2086, calc. C$_{21}$H$_{29}$N$_4$O$_6$ 433.2087.

Example 28

N-((7-Methyl-1,8-naphthyridin-2(1H)-on-3-yl) acetyl)-N-(2-(tert-butyloxycarbonyl)aminoethyl) glycine To a solution of methyl N-((7-methyl-1,8-naphthyridin-2 (1H)-on-3-yl)acetyl)-N-(2-tert-butyloxycarbonylaminoethyl)glycinate (0.775 g, 1.79 mmol) in THF (10 mL, LAB-SCAN C2520, dried over molecular seives) was added LiOH (2M, aqueous) (2.0 mL). The resulting solution was stirred at rt for 30 min, additional water was added, and the THF removed in vacuo. The pH of the aqueous solution was adjusted to pH 3.0 and the precipitate collected, and washed (2×10 mL) by filtration, to yield the desired product (424 mg, 56%) as a colorless precipitate (mp 94–95° C.). $^1$H NMR (DMSO-d$_6$; this compound exist as two rotamers; chemical shifts for the minor rotamer is given in brackets): δ 12.05 (s br, 1H), 7.90 (7.96) (d, 7.9 Hz, 1H), 7.78 (7.71) (s, 1H), 7.11 (d, 7.9 Hz, 1H), 6.90 (6,73) (m, 1H), 3.97 (4.23) (s, 2H), 3.59 (s, 2H), 3.44 (s, 3H), 3.04 (3.15) (m, 2H), 1.37 (1.36) (s, 9H). $^{13}$C NMR (DMSO-d$_6$): δ 170.94 (171.22), 170.00 (170.16), 162.6, 159.1, 155.7, 148.8, 136.30 (136.57), 135.90 (136.09), 128.28 (128.62), 118.12, 111.96 (112.00), 77.9, 48.08 (48.29), 47.5, 38.39 (38.05), 33.44 (33.66), 28.3, 24.2. FAB$^+$ HRMS (m/z): 417.1794, calc. C$_{20}$H$_{25}$N$_4$O$_6$ 417.1774.

Example 29

6-Methyl-1,8-naphthyridine-2(1H)-oxo-3-acetic Acid

To a precooled (−78° C.) solution of diisopropylamine (35.7 mmol, 3.61 g) in diethyl ether (75 mL, dried over molecular seives) was added BuLi (2.5 M in hexanes) (31.5 mmol, 12.6 mL) and the resulting solution was stirred at rt. for 15 minutes whereafter di-tert-butylsuccinate (18.7 mmol, 3.85 g) dissolved in diethyl ether (50 mL, dried over molecular seives) was slowly added. After 30 min at −78° C., 2,2-dimethyl-N-(3-formyl-5-methyl-2-pyridinyl) propanamide (17 mmol, 3.74 g) dissolved in THF (30 mL, LAB-SCAN C2520, dried over molecular seives) was slowly added and stirring of the resulting yellow mixture was continued at −78° C. for additionally 30 min and the solution then allowed to warm to rt. and poored into NH$_4$Cl (sat., aqueous) (100 mL). The aqueous phase was extracted three times with diethyl ether (50 mL, dried over molecular seives) and the organic extracts washed with brine (50 mL), dried over MgSO$_4$ and evaporated in vacuo. The crude product was recrystallised from ethyl acetate/hexane to yield the diastereomeric mixture (3.36 g, 44%) which was used as such after drying in vacuo. To a solution of the above diastereomeric mixture (7.0 mmol, 3.15 g) in dioxane (25 mL) was added HCl (3M, aqueous) (25 mL) and the resulting solution was stirred under reflux for 10 h. The dioxane was evaporated in vacuo, additional water (25 mL) was added and the pH was adjusted to 8.0 before extraction with dichloromethane (50 mL). The aqueous phase was stirred vigorously for 15 min to remove remaining dichloromethane and pH of the aqueous phase was adjusted to 4.0 by addition of HCl (2M, aqueous). The precitate was filtered of and washed with water (2×5 mL) and dried in vacuo to yield the desired product as a colorless powder (878 mg, 57%). $^1$H NMR (DMSO-d$_6$): δ 12.10 (s br, 1H, NH), 10.46 (s, 1H, COOH), 8.33 (s, 1H, arom), 7.89 (7.97) (s, 1H, arom), 7.79 (7.55) (s, 1H, arom), 3.34 (s, 2H, CH$_2$). FAB$^+$ HRMS: 219.0773 (M+H$^+$, calc. for C$_{11}$H$_{10}$N$_2$O$_3$+H$^+$ 219.0770).

Example 30

Methyl N-(2-(tert-Butyloxycarbonyl)aminoethyl)-N-(6-methyl-1,8-naphthyridin-2(1H)-oxo-3-yl)acetylglycinate To a solution of 6-methyl-1,8-naphthyridine-2(1H)-oxo-3-acetic acid (3.30 mmol, 719 mg) in DMF (20 mL) was added DIEA (3.30 mmol, 427 mg) and HBTU (3.30 mmol, 1.25 g) followed by methyl N-(2-(tert-butyloxycarbonyl)aminoethyl)glycinate (3.00 mmol, 696 mg) and this mixture was stirred for 2 h at rt. The mixture was evaporated in vacuo, redissolved in dichloromethane (100 mL) and washed with 5% aqueous NaHCO$_3$ (2×50 mL). The organic phase was dried over MgSO$_4$, filtered and evaporated in vacuo, and the crude product purified on silica using dichloromethane/methanol (95:5 v/v) as the eluent. Fractions containing the product were evaporated in vacuo to yield the desired product (551 mg, 41%) as a colorless foam. $^1$H NMR (DMSO-d$_6$; this compound exist as two rotamers; chemical shifts for the minor rotamer is given in brackets): δ 12.08 (s br, 1H, NH), 8.34 (s, 1H, arom.), 7.84 (7.91) (s, 1H, arom.), 7.73 (7.70) (s, 1H, arom.), 6.91 (6.75) (m, 1H, NH), 4.05 (4.36) (s, 2H, CH$_2$), 3.45–3.66 (two overlapping s and rotamers hereoff, 4H, 2 CH$_2$), 3.64 (s, 3H, CH$_3$O), 3.20–2.99 (m, 2H, CH$_2$), 2.34 (s, 3H, CH$_3$), 1.36 (1.37) (s, 9H, CH$_3$ (Boc)). $^{13}$C NMR (DMSO-d$_6$): δ 170.31 (170.54), 170.06, 162.45 (162.53), 155.77 (155.67), 150.29, 147.45, 136.17 (136.47), 135.42 (135.57), 129.87 (129.55), 127.35 (127.30), 113.96 (114.02), 78.01 (77.66), 51.80 (52.18), 48.20 (46.63), 47.58 (50.12), 40.60, 33.53 (33.84), 28.60, 17.38. FAB$^+$ MS: 433.2093 (M+H$^+$, calc. for C$_{21}$H$_{28}$N$_4$O$_6$+H$^+$ 433.2087).

Example 31

N-(2-(tert-Butyloxycarbonyl)aminoethyl)-N-(6-Methyl-1,8-naphthyridin-2(1H)-on-3-yl)acetylglycine To a solution of methyl N-(2-(tert-butyloxycarbonyl)aminoethyl)-N-(6-methyl-1,8-naphthyridin-2(1H)-oxo-3-yl)acetylglycinate (1.0 mmol, 405 mg) dissolved in THF (8 mL, LAB-SCAN C2520, dried over molecular seives) was added LiOH (2M, aqueous) and the resulting solution was strirred at rt for 15 min. additional water (8 mL) was added, the THF was evaporated in vacuo and pH of the aqueous phase was adjusted to 3.0 by addition of HCl (2M, aqueous). The colorless powder was filtered of and washed with water (2×5 mL) to give the desired product (228 mg, 84%) as a colorless powder, pure according to HPLC (260 nm). $^1$H NMR (DMSO-d$_6$; this compound exist as two rotamers; chemical shifts for the minor rotamer is given in brackets): δ 12.08 (s br, 1H, NH), 8.33 (s, 1H, arom.), 7.81 (7.90) (s, 1H, arom.), 7.76 (7.70) (s, 1H, arom.), 6.89 (6.73) (m, 1H, NH), 3.97 (4.23) (s, 2H, CH$_2$), 3.59 (s, 2H, CH$_2$), 3.30–3.50 (m,partly covered by water signal, 2H, CH$_2$), 3.18–3.00 (m, 2H, CH$_2$), 2.34 (s, 3H, CH$_3$), 1.36 (1.34) (s, 9H, CH$_3$ (Boc)). $^{13}$C NMR (DMSO-d$_6$): δ 170.96 (171.22), 170.14 (170.47), 162.44 (162.51), 155.74, 150.22, 147.41 (147.38), 136.13 (136.35), 135.36 (135.55), 129.90 (129.55), 127.31 (127.27), 113.97 (114.03), 78.00 (77.77), 48.19 (46.71), 47.51 (50.29), 38.98 (38.40), 33.60 (33.81), 28.26, 17.40.

Example 32

6-Chloro-1,8-naphthyridine-2(1H)-oxo-3-acetic Acid

To a precooled (−78° C.) solution of diisopropylamine (46.2 mmol, 4.67 g) in diethyl ether (100 mL, dried over molecular seives) was added BuLi (2.5 M in hexanes) (46.2 mmol, 18.5 mL) and the resulting solution was stirred at rt. for 15 min whereafter di-tert-butylsuccinate (24.2 mmol, 4.99 g) dissolved in diethyl ether (20 mL, dried over molecular seives) was slowly added. After 20 min at −78° C., 2,2-dimethyl-N-(5-chloro-3-formyl-2-pyridinyl)propanamide (22.0 mmol, 5.03 g) dissolved in THF (50 mL, LAB-SCAN C2520, dried over molecular seives) was slowly added and stirring of the resulting yellow mixture was continued at −78° C. for 60 min before the solution was allowed to warm to rt. and poored into NH$_4$Cl (sat., aqueous) (100 mL). The aqueous phase was extracted three times with diethyl ether (50 mL, dried over molecular seives) and the organic extracts washed with brine (50 mL), dried over MgSO$_4$ and evaporated in vacuo. The crude product was recrystallised from ethyl acetate/hexane to yield the diastereomeric mixture which was used as such after drying in vacuo: The crude diastereomeric mixture was dissolved in dioxane (75 mL) and HCl (3M, aqueous) (75 mL) was added. The resulting solution was stirred under reflux for 6 h, cooled to rt and filtered. The dioxane was evaporated in vacuo and pH of the aqueous phase was adjusted to 8.0 by addition of K$_2$CO$_3$, and the aqueous phase extracted with diethyl ether (25 mL, dried over molecular seives). The pH of the aqueous phase was then adjusted to pH 3.0 by addition of HCl (4M, aqueous) and the slightly tan precipitate was filtered off and washed with water (2×20 mL). The solid was dried in vacuo to yield the desired product (3.21 g, 58.2%) as a white solid. $^1$H NMR (DMSO-d$_6$): δ 12.42 (s br, 1H, NH), 10.79 (s, 1H, COOH), 8.52 (d, J=2.6 Hz, 1H, arom.), 8.28 (8.19) (d, J=2.4 Hz, 1H, arom.), 7.84 (7.74) (s, 1H, arom.), 3.50 (s, 2H, CH$_2$). FAB$^+$ MS: 239.00 (M+H$^+$, calc. for C$_{10}$H$_7$N$_2$O$_3$Cl+H$^+$ 239.0223).

Example 33

Methyl N-(2-(tert-Butyloxycarbonyl)aminoethyl)-N-(6-chloro-1,8-naphthyridin-2(1H)-oxo-3-yl)acetylglycinate To a solution of 6-Chloro-1,8-naphthyridine-2(1H)-oxo-3-acetic acid (313 mg, 1.25 mmol), triethylamine (304 mg, 3.0 mmol), DhbtOH (204 mg, 1.25 mmol) and ethyl N-(2-(tert-butyloxycarbonyl)aminoethyl)glycinate hydrochloride (283 mg, 1.0 mmol) in DMF was added DCC (258 mg, 1.25 mmol). The resulting solution was stirred overnight at rt. and evaporated in vacuo. The mixture was redissolved in dichloromethane (150 mL), filtered, and washed with 5% aqueous NaHCO$_3$ (2×50 mL), and then with brine (50 mL). The organic phase was dried over MgSO$_4$, filtered and evaporated in vacuo. The crude product was purified on silica using ethyl acetate (95:5 v/v) as the eluent. Fractions containing the product were evaporated in vacuo. to yield the desired product (294 mg, 63.0%) as a colorless powder.

$^1$H NMR (DMSO-d$_6$;this compound exist as two rotamers; chemical shifts for the minor rotamer is given in brackets): δ 12.40 (s br, 1H, NH), 8.51 (d, J=2.5 Hz, 1H, arom.), 8.23 (8.29) (d, J=2.4 Hz, 1H, arom.), 7.77 (7.74) (s, 1H, arom.), 6.90 (6.73) (t br, 1H, NH), 4.07 (4.33) (s, 2H, CH$_2$), 4.09 (4.13) (q, J=7.1 Hz, 2H, CH$_2$), 3.64 (3.50) (s, 2H, CH$_2$), 3.48 (3.29) (t, J=6.9 Hz, 2H, CH$_2$), 3.18 (3.05), (m, 2H, CH$_2$), 1.37 (1.35), (s, 9H, CH$_3$ (Boc)), 1.18 (t, J=7.1 Hz, 3H, CH$_3$). $^{13}$C NMR (DMSO-d$_6$): δ 169.99 (170.25), 169.47 (169.80), 162.40, 155.77, 147.96 (147.82), 135.61, 134.64 (134.79), 131.41 (131.06), 124.07, 115.32, 78.01 (77.78), 60.51 (61.05), 48.16 (50.26), 47.81 (46.66), 38.46 (37.99), 33.48 (33.89), 28.25, 14.11. FAB$^+$ MS: 467.1712 (M+H$^+$, calc. for C$_{21}$H$_{27}$N$_4$O$_6$Cl+H$^+$ 467.1697).

Example 34

N-(2-(tert-Butyloxycarbonyl)aminoethyl)-N-(6-methyl-1,8-naphthyridin-2(1H)-on-3-yl) acetylglycinate To a solution of methyl N-(2-(tert-butyloxycarbonyl) aminoethyl)-N-(6-chloro-1,8-naphthyridin-2(1H)-oxo-3-yl) acetylglycinate (374 mg, 0.8 mmol) was added LiOH (2M, aqueous). The resulting mixture was stirred at rt for 15 minutes. Then additional water (8 mL) was added and the THF was evaporated in vacuo, the pH of the aqueous phase was adjusted to 3.0 by addition of HCl (4M, aqueous), and the precipitate was filtered of and washed with water (2×5 mL). the resulting solution was strirred at rt for 15 minutes, additional water (8 mL) was added, the THF was evaporated in vacuo and pH of the aqueous phase was adjusted to 3.0 by addition of HCl (2M, aqueous). The white precipiate was filtered off, washed with water (2×5 mL), and dried in vacuo to give the desired product (281 mg, 80.2%) as a colorless powder, pure according to HPLC (260 nm). $^1$H NMR (DMSO-d$_6$; this compound exist as two rotamers; chemical shifts for the minor rotamer is given in brackets): δ 12.70 (s vbr, 1H, COOH), 12.39 (s br, 1H, NH), 8.51 (m, 1H, arom.), 8.20 (8.28) (d, J=2.2 Hz, 1H, arom.), 7.80 (7.74) (s, 1H, arom.), 6.88 (6.74) (m, 1H, NH), 4.21 (3.97) (s, 2H, CH$_2$), 3.63 (3.48) (s, 2H, CH$_2$), 3.45 (t, J=6.6 Hz, 2H, CH$_2$), 3.16 (3.04), (m, 2H, CH$_2$), 1.37 (1.35), (s, 9H, CH$_3$ (Boc)). $^{13}$C NMR (DMSO-d$_6$): δ 170.96 (171.26), 169.88 (170.22), 162.42 (162.48), 155.78 (155.67), 147.94 (147.82), 135.52, 134.61 (134.79), 131.47, 131.17, 115.33, 78.00 (77.78), 47.45 (50.27), 48.07 (46.71), 38.40 (37.97), 33.42 (33.56), 28.26. FAB$^+$ MS: 439.1380 (M+H$^+$, calc. for C$_{19}$H$_{23}$N$_4$O$_6$Cl+H$^+$ 439.1384) and 445.1 (M+Li$^+$, calc. for C$_{19}$H$_{23}$N$_4$O$_6$Cl+Li$^+$ 445.1466).

Example 35

3-Formyl-4-methyl-2-(pivaloylamino)pyridine

To a precooled (−78° C.) solution of 4-methyl-2-(pivaloylamino)pyridine (6.87 g, 36.0 mmol) in diethyl ether (100 mL, dried over molecular seives) was slowly added tert-BuLi (50.0 mL, 75.0 mmol). The resulting solution was stirred at −78° C. for 3.5 h prior to the addition of DMF (5.19 g, 71.0 mmol) and was stirred for additionally 30 min at −78° C. and then allowed to warm to rt, and poored into 2 M HCl (aqueous, 100 mL). After stirring this mixture for 15 min. the pH was adjusted to 7.0 by addition of K$_2$CO$_3$. The aqueous phase washed with diethyl ether (3×75 mL, dried over molecular seives), and the combined organic fractions was washed with brine (100 mL), dried (MgSO$_4$) and evaporated in vacuo. The crude product was recrystallised from ethyl acetate/hexane to give the desired product (4.66 g, 59%) as a slightly tan crystals (mp 117–20° C.). $^1$H NMR(DMSO-d$_6$): δ 11.19 (s br, 1H), 10.41 (s, 1H), 8.49 (d, 5.0 Hz, 1H), 6.92 (d, 5.0 Hz), 2.69 (s, 3H), 1.37 (s, 9H). $^{13}$C NMR (DMSO-d$_6$): δ 192.02, 176.97, 154.15, 152.82, 152.69, 121.70, 116.09, 40.69, 27.46, 18.77. FAB$^+$ MS (m/z): 221.1300 (M+H$^+$, calc. for C$_{12}$H$_{16}$N$_2$O$_2$+H$^+$ 221.1290).

Example 36

(5-Methyl-1,8-naphthyridin-2(1H)-on-3-yl)acetic Acid

To a precooled solution of N,N-diisopropylamine (6.2 mL, 0.044 mol) in diethyl ether (125 mL, dried over molecular seives) was added BuLi (2.5 M in hexanes) (17.8 mL, 0,044 mol) and the resulting solution was stirred at rt. for 15 minutes whereafter di-tert-butylsuccinate (5.35 g, 23 mmol) dissolved in diethyl ether (10 mL, dried over molecular seives) was slowly added. After 30 min at −78° C., 3-formyl-4-methyl-2-(pivaloylamino)-pyridine (4.65 g, 21.0 mmol) dissolved in THF (10 mL, LAB-SCAN C2520, dried over molecular seives) was slowly added, and stirring at this temperature was continued for 30 min. The solution was allowed to warm to rt. and poored into a solution of NH$_4$Cl (sat., aqueous, 100 mL). The aqueous phase was extracted three times with diethylether (3×50 mL) and the organic extracts washed with water (50 mL) and brine (50 mL), dried over MgSO$_4$ and evaporated in vacuo. The crude product was recrystallized from ethyl acetate/hexane to yield the diastereomeric mixture which was used as such after drying in vacuo. The diastereomeric mixture was dissolved in HCl (3M, aqueous, 50 mL) the solution was stirred under reflux for 3.5 h, cooled to rt. and washed with diethyl ether (2×50 mL), neutralised with K$_2$CO$_3$ and again washed with chloroform (3×50 mL). After precipitation upon cooling 1.39 g (37%) of the title compound was obtained (mp >250° C.). $^1$H NMR (D$_2$O/NaOD): δ 8.25 (d, 4.9 Hz, 1H), 7.71 (s, 1H), 6.84 (d, 4.9 Hz, 1H), 2.36 (s, 2H), 1.05 (s, 3H). $^{13}$C NMR (D$_2$O/NaOD): δ 180.30, 171.68, 155.44, 148.84, 146.04, 132.61, 127.08, 117.60, 116.21, 27.22, 16.98. FAB$^+$ MS (m/z): 219.10 (M+H$^+$, calc. for C$_{11}$H$_{10}$N$_2$O$_3$+H$^+$ 219.0770).

Example 37

Methyl N-((5-Methyl-1,8-naphthyridin-2(1H)-on-3-yl)acetyl)-N-(2-(tert-butyloxycarbonyl)aminoethyl) glycinate To a precooled (0° C.) solution of (5-methyl-1,8-naphthyridin-2(1H)-on-3-yl)acetic acid (1.20 g, 5.50 mmol) and DhbtOH (0.987 g, 6.10 mmol) in DMF (25 mL) was added DCC (1.25 g, 6.10 mmol) and the resulting mixture was stirred for 40 min. prior to the addition of methyl N-(2-(tert-butyloxycarbonyl)aminoethyl)glycinate (1.32 g, 6.10 mmol). The mixture was stirred at rt. overnight, evaporated in vacuo, redissolved in ethyl acetate (75 mL) and the DCU filtered off. The organic phase was washed with NaHCO$_3$ (3×25 mL) and with brine (2×25 mL), dried (MgSO$_4$) and evaporated in vacuo. The crude product was purified on silica using MeOH/dichloromethane (95:5 to 90:10 v/v) as the eluent. Fractions containing the product were pooled and evaporated in vacuo. to yield the desired product (752 mg, 33%) (mp 175–77° C.). $^1$H NMR (DMSO-d$_6$; this compound exists as two rotamers; chemical shifts for the minor rotamer is given in brackets): δ 12.10 (12.08), (s br, 1H), 8.33 (8.33) (d, J=4.8 Hz, 1H), 7.96 (7.90) (s, 1H), 7.09 (d, J=4.8 Hz, 1H), 6.92 (6.70) (m, 1H), 4.07 (4.37) (s, 2H), 3.67 (s, 2H), 3.64 (s, 3H), 3.46 (m, 2H), 3.17 (m, 2H), 2.54 (2.53) (s, 3H), 1.37 (1.35) (s, 9H). $^{13}$C NMR (DMSO- $d_6$): δ 170.30 (170.50), 170.04, 162.30, 155.73, 149.47, 149.25, 145.16, 132.92 (133.56), 129.12 (129.28), 119.87, 113.35, 77.97, 52.13, 51.76 (50.12), 47.47 (48.16), 38.98 (38.39), 33.81 (33.99), 28.24, 17.66. FAB+MS (m/z): 433.2087 (M+H$^+$, calc. for $C_{21}H_{28}N_4O_6$+H$^+$ 433.2086).

Example 38

N-((5-Methyl-1,8-naphthyridin-2(1H)-on-3-yl) acetyl)-N-(2-(tert-butyloxycarbonyl)aminoethyl) glycine To a solution of methyl N-((5-methyl-1,8-naphthyridin-2 (1H)-on-3-yl)acetyl)-N-(2-(tert-butyloxycarbonyl) aminoethyl)glycinate (0.72 g, 1.70 mmol) in THF (10 mL) was added LiOH (aqueous, 2M) (2.0 mL). The resulting solution was stirred at rt. for 45 min. then additional water was added, the THF was evaporated in vacuo and the pH of the aqueous solution was adjusted to 3.0. The resulting precipitate was washed with water (2×10 mL), collected by centrifugation and dried in vacuo to yield the desired product (366 mg, 53%) as a white powder (mp 133–36° C.). $^1$H NMR (DMSO-$d_6$; this compound exist as two rotamers; chemical shifts for the minor rotamer is given in brackets): δ 12.12 (s br, 1H), 8.33 (d, J=4.9 Hz, 1H), 8.00 (s, 1H), 7.09 (d, J=4.9 Hz, 1H), 6.92 (6.70) (m, 1H), 3.99 (4.26) (s, 2H), 3.62 (s, 2H), 3.45 (m, 2H+H2O), 3.17 (m, 2H), 2.53 (2.52) (s, 3H), 1.36 (1.34) (s, 9H) $^{13}$C NMR (DMSO-$d_6$): δ 171.07 (171.31), 170.23 (170.54), 162.36, 155.80, 149.53, 149.27, 145.30, 132.67 (133.55), 129.35 (129.20), 119.92, 113.44, 78.01, 48.13, 47.33, 38.60 (38.36), 34.07, 28.27, 17.76. FAB$^-$ HRMS (m/z): 417.1798, calc. $C_{20}H_{26}N_4O_6$–H 417.1774.

Example 39

Hybridization Studies Using Modified PNA's

The binding of each PNA was measured in a solution ca. 3 µM in PNA and DNA or PNA and PNA at pH 7.0 in 100 mM NaCl, 10 mM sodium phosphate, 0.1 mM EDTA. Absorption at 260 nm were recorded at 0.5° C. intervals from 5–90° C.

Substitutions are abreviated as shown below:

(E1) N-(benzo[b][1,8]napthyridin-2(1H)-on-3-yl)acetyl)-N-(2-Boc-aminoethyl)glycine;

(E2) 7-chloro-1,8-naphthyridin-2(1H)-one;

(E3) 6-chloro-1,8-naphthyridin-2(1H)-one;

(E4) 7-methyl-1,8-naphthyridin-2(1H)-one;

(E5) 6-methyl-1,8-naphthyridin-2(1H)-one; and (E6) 5-methyl-1,8-naphthyridin-2(1H)-one.

$\Delta T_m$'s are indicated per modification, relative to the thermal stability of thymine containing controls.

A. Hybridization of PNA 10-mers Having One Modified Position Against Complementary PNA and DNA Target Sequences The hybridization of PNA 10 mers having 0 or 1 modifications incorporated at selected positions was measured against both PNA (SEQ ID No. 21) and DNA (SEQ ID No. 22) (see Example 20) target sequences. The PNA sequences were prepared as illustrated in Egholm, supra.

The PNA 10-mers differ only with respect to a single position within the 10-mer that is occupied by a modified PNA monomer (see table below).

| SEQ ID No. | PNA SEQUENCE | Tm (° C.) DNA/PNA | Tm (° C.) DNA/PNA |
|---|---|---|---|
| 23 | H-GTAGATCACT-Lys-NH$_2$ | 51.0/68.5 | — |
| 24 | H-GTAGA(E1)CACT-Lys-NH$_2$ | 51.0/68.5 | 0.0/0.0 |
| 26 | H-GTAGA(E2)CACT-Lys-NH$_2$ | 53.0/72.5 | 2.0/4.0 |
| 27 | H-GTAGA(E3)CACT-Lys-NH$_2$ | 53.0/69.0 | 2.0/0.5 |
| 28 | H-GTAGA(E4)CACT-Lys-NH$_2$ | 54.0/71.0 | 3.0/2.5 |
| 29 | H-GTAGA(E5)CACT-Lys-NH$_2$ | 51.0/68.0 | 0.0/0.5 |
| 30 | H-GTAGA(E6)CACT-Lys-NH$_2$ | 53.0/70.0 | 2.0/0.5 |

B. Hybridization of PNA 10-mers Having Three Modified Positions Against Complementary PNA and DNA Target Sequences The hybridization of PNA 10 mers having 0 or 3 modifications incorporated at selected positions was measured against both PNA (SEQ ID No. 21) and DNA (SEQ ID No. 22) (see Example 20) target sequences. The PNA sequences were prepared as illustrated in Egholm, supra.

The PNA 10-mers differ only with respect to three positions within the 10-mer that are occupied by modified PNA monomers (see table below).

| SEQ ID No. | Target sequence | |
|---|---|---|
| 31 | H-CATCATCTAC-Lys-NH$_2$ | (PNA) |
| 32 | 5'-dCATCATCTAC-3' | (DNA) |

| SEQ ID No. | PNA SEQUENCE | Tm (° C.) DNA/PNA | Tm (° C.) DNA/PNA |
|---|---|---|---|
| 33 | H-GTAGATGATG-Lys-NH$_2$ | 58.5/67.5 | — |
| 34 | H-G(E1)AGA(E1)GA(E1)G-Lys-NH$_2$ | 55.0/63.0 | −1.7/−1.5 |
| 35 | H-G(E2)AGA(E2)GA(E2)G-Lys-NH$_2$ | 67.5/79.5 | 3.0/4.0 |
| 36 | H-G(E3)AGA(E3)GA(E3)G-Lys-NH$_2$ | 52.5/64.0 | /−1.2 |
| 37 | H-G(E4)AGA(E4)GA(E4)G-Lys-NH$_2$ | 58.0/65.0 | −0.2/−0.8 |
| 38 | H-G(E5)AGA(E5)GA(E5)G-Lys-NH$_2$ | nd/nd | nd/nd |
| 39 | H-G(E6)AGA(E6)GA(E6)G-Lys-NH$_2$ | 53.0/63.5 | −1.8/−1.3 |

C. Hybridization of PNA 10-mers Having Three Modified Positions Against Complementary PNA and DNA Target Sequences The hybridization of PNA 10 mers having 0 or 3 modifications incorporated at selected positions was measured against both PNA (SEQ ID No. 40) and DNA (SEQ ID No. 41) target sequences. The PNA sequences were prepared as illustrated in Egholm, supra.

The PNA 10-mers differ only with respect to three positions within the 10-mer that are occupied by modified PNA monomers (see table below).

| SEQ ID No. | Target sequence | |
|---|---|---|
| 40 | H-CTCAAACTCT-Lys-NH$_2$ | (PNA) |
| 41 | 5'-dCTCAAACTCT-3' | (DNA) |

| SEQ ID No. | PNA SEQUENCE | Tm (° C.) DNA/PNA | Tm (° C.) DNA/PNA |
|---|---|---|---|
| 42 | H-AGAGTTTGAG-LysNH$_2$ | 59.5/66.5 | — |
| 43 | H-AGAG(E1)(E1)(E1)GAG-LysNH$_2$ | 58.0/64.5 | −0.5/−0.7 |
| 44 | H-AGAG(E2)(E2)(E2)GAG-LysNH$_2$ | 75.0/78.0 | 5.2/3.8 |
| 45 | H-AGAG(E3)(E3)(E3)GAG-LysNH$_2$ | 64.0/67.0 | 1.5/0.2 |
| 46 | H-AGAG(E4)(E4)(E4)GAG-LysNH$_2$ | 63.5/68.0 | 1.3/1.5 |

| 47 | H-AGAG(E5)(E5)(E5)GAG-LysNH$_2$ | nd/nd | nd/nd |
|----|-------------------------------|-------|-------|
| 48 | H-AGAG(E6)(E6)(E6)GAG-LysNH$_2$ | 60.5/66.0 | 0.3/−0.2 |

D. Hybridization of PNA 10-mers Having Three Modified Positions Against Complementary PNA and DNA target Sequences The hybridization of PNA 10 mers having 0 or 1 modification incorporated at a selected position was measured against PNA and DNA strands that are either complementary or have a single mismatch at the position that is modified in the modified PNA's. An unmodified PNA is also hybridized with the 8 targets as a standard. DNA (5'-dAGT GXT CTA C-3') or PNA (H-AGT GXT CTA C—NH$_2$) were prepared with the X position representing one of A, G, C, or T, thereby giving 8 individual target sequences (see table below).

| SEQ ID No. | Target sequence | |
|---|---|---|
| 49 | H-AGT GAT CTA C-NH$_2$ | (PNA) |
| 50 | H-AGT GGT CTA C-NH$_2$ | (PNA) |
| 51 | H-AGT GCT CTA C-NH$_2$ | (PNA) |
| 52 | H-AGT GTT CTA C-NH$_2$ | (PNA) |
| 53 | 5'-dAGT GAT CTA C-3' | (DNA) |
| 54 | 5'-dAGT GGT CTA C-3' | (DNA) |
| 55 | 5'-dAGT GCT CTA C-3' | (DNA) |
| 56 | 5'-dAGT GTT CTA C-3' | (DNA) |

| SEQ. ID No. | PNA SEQUENCE | X = A Tm (° C.) DNA PNA | X = G Tm (° C.) DNA PNA | X = C Tm (° C.) DNA PNA | X = T Tm (° C.) DNA PNA |
|---|---|---|---|---|---|
| 57 | H-GTAGATCACT-LysNH$_2$ | 51.0 / 68.5 | 37.0 / 60.0 | 45.0 / 52.5 | 41.0 / 50.5 |
| 58 | H-GTAGA(E1)CACT-LysNH$_2$ | 51.0 / 68.5 | 46.5 / 62.0 | C.36 / 50.5 | 43.0 / c.48 |
| 59 | H-GTAGA(E2)CACT-LysNH$_2$ | 53.0 / 72.5 | 46.0 / 60.0 | 48.0 / 50.5 | 47.0 / 49.5 |

E. Hybridization of bis-PNA's (Each Being an Anti-parallel 7-mer Coupled Via Three Linked 8-Amino-3,6-dioxaoctanoic Acid (egl) Groups) Containing 3 Isolated Modifications in the Hoogsteen Strand to a 13-mer DNA Having a 7-mer Target Region The hybridization of PNA 10 mers having 0 or 3 modifications incorporated at selected positions in the Hoogsteen strand was measured against a 13-mer DNA containing the 7-mer target sequence. Adenines were positioned within the 13-mer DNA target matching positions that were modified in the hoogsteen strand. The synthesis of the bis-PNAs was carried out as illustrated in Egholm, supra. (see table below). The bis-PNA's were prepared having two 10-mer PNA's joined in an anti-parallel orientation via three consecutive 8-amino-3,6-dioxaoctanoic acid (egl) groups. Positions in the Hoogsteen strand that would normally have a protonated cytosine (as determined by the target sequence) are occupied by pseudoisocytosine (represented as "J"). The δTm is indicated per modification, relative to the thermal stability of the thymine containing control.

| SEQ | PNA SEQUENCE | Tm/ΔTm (° C.) |
|---|---|---|
| 60 | H-TTJTTTJ-(egl)$_3$-CTTTCTT-NH$_2$ | 59.5/— |
| 61 | H-T(E1)J(E1)T(E1)J-(egl)$_3$-CTTTCTT-NH$_2$ | 63.0 1.2 |
| 62 | H-T(E2)J(E2)T(E2)J-(egl)$_3$-CTTTCTT-NH$_2$ | 65.5/2.0 |
| 63 | H-T(E3)J(E3)T(E3)J-(egl)$_3$-CTTTCTT-NH$_2$ | 67.5/2.7 |
| 64 | H-T(E4)J(E4)T(E4)J-(egl)$_3$-CTTTCTT-NH$_2$ | nd/nd |
| 65 | H-T(E5)J(E5)T(E5)J-(egl)$_3$-CTTTCTT-NH$_2$ | 63.0/1.2 |
| 66 | H-T(E6)J(E6)T(E6)J-(egl)$_3$-CTTTCTT-NH$_2$ | 64.5/1.7 |

F. Hybridization of bis-PNA's (Each Being an Anti-parallel 7-mer Coupled Via Three Linked 8-Amino-3,6-dioxaoctanoic Acid (egl) Groups) Containing 3 Adjacent Modifications in the Hoogsteen Strand to a 13-mer DNA Having a 7-mer Target Region The hybridization of PNA 10 mers having 0 or 3 modifications incorporated at selected positions in the Hoogsteen strand was measured against a 13-mer DNA containing the 7-mer target sequence. Adenines were positioned within the 13-mer DNA target matching positions that were modified in the hoogsteen strand. The synthesis of the bis-PNAs was carried out as illustrated in Egholm, ibid. (see table below). The bis-PNA's were prepared having two 10-mer PNA's joined in an anti-parallel orientation via three consecutive 8-amino-3,6-dioxaoctanoic acid (egl) groups. Positions in the Hoogsteen strand that would normally have a protonated cytosine (as determined by the target sequence) are occupied by pseudoisocytosine (represented as "J"). The ΔT$_m$ is indicated per modification, relative to the thermal stability of the thymine containing control.

| SEQ | PNA SEQUENCE | Tm/ΔTm (° C.) |
|---|---|---|
| 67 | H-TJTTTTJ-(egl)$_3$-CTTTTCT-NH$_2$ | 61.0/— |
| 68 | H-TJ(E1)(E1)(E1)TJ-(egl)$_3$-CTTTTCT-NH$_2$ | 65.5/1.5 |
| 69 | H-TJ(E2)(E2)(E2)TJ-(egl)$_3$-CTTTTCT-NH$_2$ | 71.5/3.5 |
| 70 | H-TJ(E3)(E3)(E3)TJ-(egl)$_3$-CTTTTCT-NH$_2$ | 70.5/3.2 |
| 71 | H-TJ(E4)(E4)(E4)TJ-(egl)$_3$-CTTTTCT-NH$_2$ | 63.5/0.8 |
| 72 | H-TJ(E5)(E5)(E5)TJ-(egl)$_3$-CTTTTCT-NH$_2$ | 67.5/2.2 |
| 73 | H-TJ(E6)(E6)(E6)TJ-(egl)$_3$-CTTTTCT-NH$_2$ | 66.5/1.8 |

Examples 40–42

The preparation of the monomer synthon having the formula X is shown below (Examples 40–42):

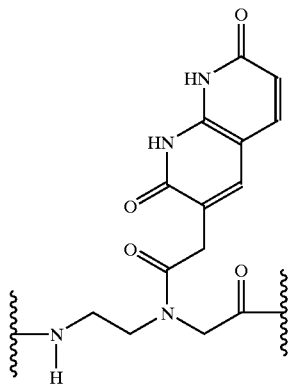

The novel 1,8-naphthyridin-2(1H)-on-3-yl nucleobase is a surrogate for the J base, which in preferred embodiments is capable of recognizing G-containing base pairs in triplex formation motifs.

Example 40

(1,8-Naphthyridine-2,7(1,8H)-dion-3-yl)acetic Acid

A suspension of (7-chloro-1,8-naphthyridin-2(1H)-on-3-yl)acetic acid (4.00 g, 17.0 mmol) in NaOH (6 M, aqueous) (50 mL) was heated to reflux for 19 hours and then allowed to cool to rt. The pH of the aqueous solution was adjusted to 7.0 by addition of HCl (conc, aqueous) and the resulting precipitate was collected by filtration and washed repeatedly with water to give the desired product (3.47 g, 94%) as a colorless powder (mp>250° C.). $^1$H NMR (DMSO-d$_6$): δ 11.83 (br, 2H), 7.81 (d, J=8.8 Hz, 1H), 7.69 (s, 1H), 6.37 (d, J=8.8, 1H), 3.40 (s, 2H, hidden by watersignal). $^{13}$C NMR (D$_2$O/NaOD): δ 184.03, 174.45, 173.44, 141.12, 139.79, 122.42, 113.63, 110.97, 41.92. FAB$^+$ MS (m/z): 175.92 (M–COOH+H$^+$, calc for C$_9$H$_7$N$_2$O$_2$ 176.0586).

Example 41

Methyl N-((1,8-Naphthyridine-2,7(1,8H)-dion-3-yl) acetyl)-N-(2-tert-butyloxycarbonyl)aminoethyl) glycinate (3)

To a precooled solution of (1,8-naphtyridin-2,7(1,8H)-dion-3-yl)acetic acid (1.80 g, 8.38 mmol) and HOAt (1.34 g, 10.1 mmol) in DMF was added DCC (2.08 g, 10.1 mmol) and the mixture was stirred for 40 minutes at 0° C. prior to addition of methyl N-(N-tert-butyloxycarbonyl)aminoethyl) glycinate (2.22 g, 9.00 mmol). The mixture was stirred overnight at rt, evaporated in vacua, redissolved in dichlorormethane (100 mL) and DCU filtered off. The organic phase was washed with NaHCO$_3$ (sat., aqueous) (3×75 mL), brine (2×100 mL), dried over MgSO$_4$ and evaporated in vacuo. The crude product was purified on silica with AcOH/MeOH/CH$_2$Cl$_2$ (2/9/89 v/v/v) as the eluent. The product containing fractions were pooled and evaporated in vacuo to yield the desired product (1.70 g, 46%) (mp 197–198° C.). $^1$H NMR (DMSO-d$_6$): δ 7.50 (7.55) (d, J=8.8 Hz, 1H), 7.45 (7.40) (s, 1H), 6.93 (6.71) (m, 1H), 5.99 (m, 1H), 4.04 (4.39) (s, 2H), 3.63 (s, 3H), 3.47 (3.50) (m, 2H), 3.32 (3.31) (m, 2H), 3.16 (3.03) (q, J=6.0 Hz, 2H), 1.35 (1.34) (s, 9H). $^{13}$C NMR (DMSO-d$_6$): δ 171.54 (171.77), 170.17 (170.53), 165.89, 155.78, 148.79, 138.64, 136.48 (136.93), 118.01 (117.56), 111.67, 101.80, 77.90 (77.72), 51.75 (52.07), 48.21 (50.15), 47.59 (46.51), 38.10, 33.30 (33.88), 28.26. FAB$^+$ MS (m/z): 435.1871 (M+H$^+$, calc. for C$_{20}$H$_{27}$N$_4$O$_7$ 435.1880).

Example 42

N-((1,8-Naphthyridine-2,7(1,8H)-dion-3-yl)acetyl)-N-(2-(tert-butyloxycarbonyl)aminoethyl)glycine (4)

To a precooled (0° C.) solution of methyl N-((1,8-naphthyridin-2,7(1,8H)-dion-3-yl)acetyl)-N-(2-(tert-butyloxycarbonyl)aminoethyl)glycinate (1.70 g, 3.79 mmol) in THF (20 mL) was added NaOH (2M, aqueous) (20 mL). This solution was stirred at rt. for 15 min, additional water was added and the THF evaporated in vacuo. The pH of the aqueous solution was adjusted to 3.0 by addition of HCl (2M, aqueous) and the resulting precipitate washed with water (2×5 mL), collected by centrifugation and dried to yield the desired product (1.31 g, 82%) as a colorless powder (mp 195–97° C.). $^1$H NMR (DMSO-d$_6$): δ 11.90 (s br, 2H), 7.76 (7.83) (d, J=8.8 Hz, 1H), 7.68 (7.61) (s, 1H), 6.89 (6.72) (m, 1H), 6.39 (6.38) (d, J=8.8 Hz, 1H), 3.96 (4.21) (s, 2H), 3.53 (3.43) (s, 2H), 3.34 (m, 2H hidden by water signal), 3.16 (3.03) (m, 2H), 1.36 (1.35) (s, 9H). $^{13}$C NMR (DMSO-d$_6$): δ 171.13 (171.48), 170.82 (170.46), 163.37, 162.51, 147.30, 139.14 (139.33), 137.25 (137.52), 122.17, 109.00, 105.90, 78.01, 48.08 (50.38), 47.60 (46.76), 38.41 (38.02), 33.43 (33.14), 28.27. FAB+MS (m/z): 421.1723 (M+H$^+$, calc. for C$_{19}$H$_{25}$N$_4$O$_7$ 421.1723), 443.1543 (M+Na$^+$, calc. for C$_{19}$H$_{24}$N$_4$O$_7$Na$^+$ 443.1543).

Example 43

Hybridization/pH Dependence (pH 9.0, 7.0 and 5.0) of Modified bis-PNA's (Each Being an Antiparallel 7-mer Coupled Via Three Linked 8-Amino-3,6-dioxaoctanoic Acid (egl) Groups) Containing Modifications in the Hoogsteen Strand (E7)=1,8-naphthyridin-2,7(1,8H)-dione
(E8)=phenothiazine A. Hybridization of bis-PNA's Having Cytosines, Pseudoiscytosines or 1,8-Naphthyridin-2,7(1,8H)-dione in the Hoogsteen Strand The hybridization of the diketo tautomer of the 1,8-naphthyridin-2,7(1,8H)-dione (E7) is compared to cytosine and pseudoisocytosine in a bis-PNA 7-mer targeted to a complementary target region in a synthetic DNA 5'-dCGCAGAGAAACGC-3' (SEQ ID NO 74).

| SEQ | PNA SEQUENCE | Tm (° C.) pH 9.0/7.0/5.0 |
| --- | --- | --- |
| 75 | H-TCTCTTT-(egl)$_3$-TTTCTCT-NH$_2$ | 38.5/49.0/69.0 |
| 76 | H-TJTJTTT-(egl)$_3$-TTTCTCT-NH$_2$ | 60.5/64.0/67.0 |
| 77 | H-T(E7)T(E7)TTT-(egl)$_3$-TTTCTCT-NH$_2$ | 59.5/66.0/73.0 |

B. Hybridization of bis-PNA's Having Cytosines, Pseudoiscytosines, Phenothiazines or 1,8-Naphthyridin-2,7 (1,8H)-dione in Isolated Positions in the Hoogsteen Strand The hybridization of the diketo tautomer of the 1,8-naphthyridin-2,7(1,8H)-dione (E7) is compared to cytosine, seudoisocytosine, and phenothiazine in a bis-PNA 7-mer targeted to a complementary target region in a synthetic DNA 5'-dCGCAGAGAGACGC-3' (SEQ ID NO 78).

| SEQ | PNA SEQUENCE | Tm (° C.) pH 9.0/7.0/5.0 |
|---|---|---|
| 79 | H-TCTCTCT-(egl)₃-TCTCTCT-NH₂ | 42.0/50.5/78.0 |
| 80 | H-TJTJTJT-(egl)₃-TCTCTCT-NH₂ | nd/66.0/nd |
| 81 | H-T(E8)T(E8)T(E8)T-(egl)₃-TCTCTCT-NH₂ | 70.0/42.0/41.0 |
| 82 | H-T(E7)T(E7)T(E7)T-(egl)₃-TCTCTCT-NH₂ | nd/70.5/nd |

C. Hybridization of bis-PNA's Having Cytosines, Pseudoiscytosines, Phenothiazines or 1,8-Naphthyridin-2,7 (1,8H)-dione in Adjacent Positions the Hoogsteen Strand The hybridization of the diketo tautomer of the 1,8-naphthyridin-2,7(1,8H)-dione (E7) is compared to cytosine, seudoisocytosine, and phenothiazine in a bis-PNA 7-mer targeted to a complementary target region in a synthetic DNA 5'-dCGCAAGGGAACGC-3' (SEQ ID NO 83).

| SEQ | PNA SEQUENCE | Tm (° C.) pH 9.0/7.0/5.0 |
|---|---|---|
| 84 | H-TTCCCTT-(egl)₃-TTCCCTT-NH₂ | 36.5/47.5/77.5 |
| 85 | H-TTJJJTT-(egl)₃-TTCCCTT-NH₂ | nd/62.5/nd |
| 86 | H-TT(E8)(E8)(E8)TT-(egl)₃-TTCCCTT-NH₂ | 34.5/44.5/74.5 |
| 87 | H-TT(E7)(E7)(E7)TT-(egl)₃-TTCCCTT-NH₂ | nd/75.5/nd |

Examples 44–56

The preparation of the monomer synthons having the formula XI–XIII is shown below (Examples 44–55):

XI

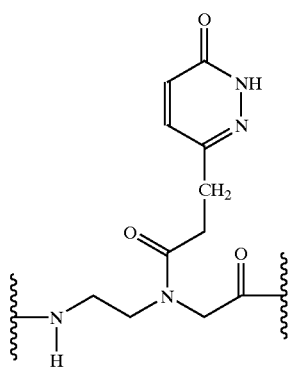

XII

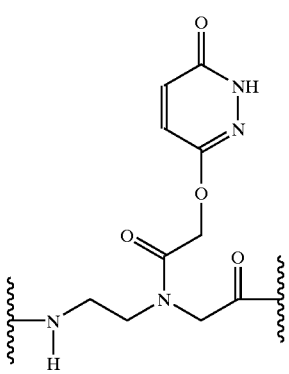

XIII

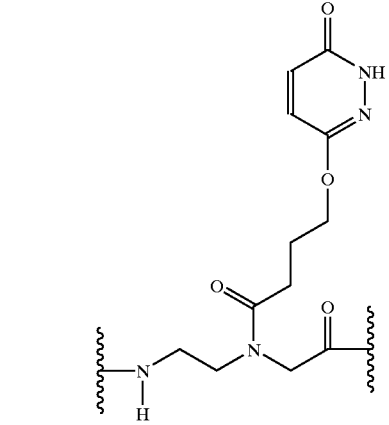

These nucleobase monomers are advantageously employed in antisense applications, as recognizers of T residues in both duplex and triplex formation.

Example 44

Ethyl (3-oxo-2,3,4,5-Tetrahydropyridazin-6-yl) propionate

To a solution of hydrazine monohydrate (95 mmol, 4.76 g) in abs. ethanol (50 mL) was added diethyl 4-oxopimelate (100 mmol, 23.03 g). The mixture was stirred at rt. for 1 h and evaporated to dryness in vacuo to give the desired product (18.96 g, quantitative) as a pure (HPCL 260 nm) white solid. The material was analyzed by HPLC (260 nm) and found to be pure. UV λmax 242 nm. ¹H NMR (CDCl₃): δ 8.61 (s br, 1H, NH), 4.11 (q, J=7.1 Hz, 2H, CH₂), 2.60–2.55 (m, 4H, 2CH₂), 2.50.2.40 (m, 4H, 2CH₂), 1.22 (t, J=7.1 Hz, 3H, CH₃). ¹³C NMR (CDCl₃): δ 172.41, 167.16, 153.35, 60.36, 30.85 29.76, 25.17, 14.00. FAB⁺ MS: 199.1085 (M+H⁺, calc. for C₉H₁₄N₂O₃+H⁺ 199.1083).

Example 45

Ethyl (3-oxo-2,3,-Dihydropyridazin-6-yl)-propionate

To a solution of ethyl (3-oxo-2,3,4,5-tetrahydropyridazin-6-yl)-propionate (50.0 mmol, 9.90 g) in ethanol (50 mL) was added bromine (75.0 mmol, 11.99 g). The mixture was stirred at rt for 14 h and the mixture was poored into NaHCO₃ (sat. aqueous) (500 mL). The resulting mixture was extracted exhaustively with diethylether (5×500 mL). The combined organic fractions were dried over MgSO₄ and evaporated in vacuo. The crude product was recrystallized from toluene to give the title compound (3.35 g, 34.1%) as colorless needles of high purity (HPLC at 260 nm). UV λmax 228 nm and 285 nm. ¹H NMR (CDCl₃): δ 11.62 (s br, 1H, NH), 7.18 (d, J=9.7 Hz, 1H, arom.), 7.88 (d, J=9.7 Hz, 1H, arom.), 4.11 (q, J=7.1 Hz, 2H, CH₂), 2.90 (t, J=7.0 Hz, 2H, CH₂), 2.64 (t, J=7.0 Hz, 2H, CH₂), 1.25 (t, J=7.1 Hz, 3H, CH₃). ¹³C NMR (CDCl₃): δ 172.20, 161.50, 146.73, 134.06, 129.74, 60.45, 31.47, 25.89, 13.97. FAB⁺ MS: 197.10 (M+H⁺, calc. for C₉H₁₂N₂O₃+H⁺ 197.0926).

Example 46

3-oxo-2,3,-Dihydropyridazin-6-yl-propionic Acid

To a solution of Ethyl (3-oxo-2,3,-dihydropyridazin-6-yl)-propionate (3.00 mmol, 589 mg) in THF was added LiOH (2M, aqueous) (7.50 mL). The solution was stirred at rt. for 15 minutes, additional water (25 mL) was added and the THF removed in vacuo. The pH of the aqueous phase was adjusted to 3.0 by addition of HCl (2M, aqueous) and the solid material filtered off and washed with water (2×3 mL). The solid was dried in vacuo to yield the desired product (461 mg, 91.4%) as a colorless powder. $^1$H NMR (CDCl$_3$): δ 11.62 (s br, 1H, NH), 7.18 (d, J=9.7 Hz, 1H, arom.), 7.88 (d, J=9.7 Hz, 1H, arom.), 4.11 (q, J=7.1 Hz, 2H, CH$_2$), 2.90 (t, J=7.0 Hz, 2H, CH$_2$), 2.64 (t, J=7.0 Hz, 2H, CH$_2$), 1.25 (t, J=7.1 Hz, 3H, CH$_3$). FAB$^+$ MS: 169.0611 (M+H$^+$, calc. for C$_9$H$_{12}$N$_2$O$_3$+H$^+$ 169.0613).

Example 47

Methyl N-(2-Bocaminoethyl)-N-[3-oxo-2,3,-dihydropyridazin-6-yl-propionyl]glycineate To a solution of 3-oxo-2,3,-dihydropyridazin-6-yl-propionic acid (2.00 mmol, 336 mg) in DMF was added triethylamine (2.00 mmol, 202 mg), DhbtOH (2.20 mmol, 359 mg), and methyl N-(2-Boc-aminoethyl)glycinate (2.20 mmol, 464 mg) followed by DCC (2.20 mmol, 454 mg). The solution was stirred overnight at rt and evaporated in vacuo. The resulting oil was taken up in dichloromethane (100 mL), washed twice with NaHCO$_3$ (sat, aqueous, 50 mL), washed with brine (50 mL), dried over MgSO$_4$ and evaporated to dryness in vacuo. The crude product was purified on silica using ethyl acetate/methanol (95:5) as the eluent. Fractions containing the product were pooled and evaporated in vacuo to yield the title compound (405 mg, 53%), as a colorless foam. $^1$H NMR (DMSO-d$_6$): δ 12.74 (s br, 1H, NH), 7.37 (7.35) (d, J=9.7 Hz, 1H, arom.), 6.79 (d, J=9.7 Hz, 1H, arom.), 6.85 (6.69) (t, 1H, NH), 4.00 (4.24) (s, 2H, CH$_2$), 3.61 (s, 3H, CH$_3$), 3.39 (3.30) (t, 2H, CH$_2$), 3.08 (2.99) (q, 2H, CH$_2$), 2.80–2.50 (m, 4H, 2×CH$_2$), 1.33 (1.36) (s, 9H, Boc). $^{13}$C NMR (DMSO-d$_6$): δ 170.391 (170.66), 168.78 (169.12), 159.08, 154.45, 145.49 (145.58), 133.09 (133.15), 128.25, 76.73 (76.51), 50.50 (50.98), 46 24 (48.48), 46.44 (45.26), 37.09 (36.72), 28.71 (29.12), 28.02 (27.87), 26.99 (27.05).

Example 48

N-(2-Bocaminoethyl)-N-[3-oxo-2,3,-dihydropyridazin-6-yl-propionyl]glycine (Formula XI)

To a solution of methyl N-(2-Bocaminoethyl)-N-[3-oxo-2,3,-dihydropyridazin-6-yl-propionyl]glycinate (1.00 mmol, 382 mg) in THF (12.5 mL) was added LiOH (2M, aqueous, 2.0 mL). The solution was stirred at rt. for 15 minutes, additional water (10 mL) was added and the THF was removed in vacuo. The pH of the aqueous phase was adjusted to 3.0 by addition of HCl (2M, aqueous). The product was isolated by continuous extraction with dichloromethane (DCM) followed by evaporation in vacuo to give the desired product (215 mg, 80%) as a colorless powder (UV$_{max}$ 287 nm). $^1$H NMR (DMSO-d$_6$): δ 12.73 (s br and s vbr, 2H, NH and COOH), 7.38 (7.35) (d, J=9.7 Hz, 1H, arom.), 6.78 (d, J=9.7 Hz, 1H, arom.), 6.83 (6.70) (t, 1H, NH), 3.92 (4.11) (s, 2H, CH$_2$), 3.39–3.27 (m, 2H, CH$_2$), 3.08 (3.00) (q, 2H, CH$_2$), 2.73–2.66 (m, 2H, CH$_2$), 2.69–2.52 (m, 2H, CH$_2$), 1.33 (1.36) (s, 9H, Boc). $^{13}$C NMR (DMSO-d$_6$): δ 171.50 (171.93), 171.04 (171.38), 160.39, 155.73, 146.88 (146.92), 134.41, 129.53, 77.99 (77.76), 47.44 (49.98), 47.61 (46.64), 38.31 (37.97), 30.05 (30.40), 29.31 (29.12), 28.24. FAB$^+$ MS: 369.14 (M+H$^+$, calc. for C$_{16}$H$_{24}$N$_4$O$_6$+H$^+$ 369.1774).

Example 49

O-(3-oxo-2,3-Dihydropyridazin-6-yl)-2-oxy-acetic Acid 3,6-dihydroxypyridazine (5.00 g, 44.6 mmol) was suspended in abs. ethanol/water (3:1) (40 mL) and KOH (2.10 g, 37.6 mmol) was added. After 30 min ethyl bromoacetate (9.20 g, 54.9 mmol) was slowly added. The suspension was heated to reflux and left overnight. The mixture was evaporated in vacuo and additional water (30 mL) was added. The aqueous phase was extracted with ethyl acetate (4×50 mL) and the organic fractions evaporated in vacuo. The crude product was purified on a silica gel column using methanol/chloroform (1:4 v/v) containing 1% acetic acid as the eluent. Fractions containing the product were pooled and evaporated in vacuo to give the desired product (1.56 g, 21%) (pure according to TLC, Rf 0.32 using methanol/chloroform (1:4 v/v) containing 1% actic acid). $^1$H NMR (DMSO-d$_6$): δ 12.10 (s br, 1H, NH), 7.15 (d, J=9.9 Hz, 1H, arom), 6.83 (d, J=9.9 Hz, 1H, arom), 4.29 (s, 2H, CH$_2$). $^{13}$C-NMR (DMSO-d$_6$): δ 170.77, 159.77, 152.77, 132.53, 128.23, 65.65. FAB$^+$ MS: No signal corresponding to the molecular mass was observed.

Example 50

Ethyl N-(2-Bocaminoethyl)-N-[O-(3-oxo-2,3-dihydropyridazin-6-yl)-2-oxy-acetyl]glycinate Ethyl N-(2-Bocaminoethyl)glycinate (395 mg, 1.60 mmol) was dissolved in DMF (10 mL) and O-(3-oxo-2,3-dihydropyridazin-6-yl)-2-oxy-acetic acid (300 mg, 1.76 mmol) followed by 3-hydroxy-1,2,3-benzotriazine-4(3H)-one (291 mg, 1.78 mmol) were added. The mixture was cooled on ice and N,N'-dicyclohexylcarbodiimide (404 mg, 1.96 mmol) was added. After 1 h the ice bath was removed and the mixture stirred overnight at rt. The mixture was evaporated in vacuo and the crude product was purified on silica using dichloromethane/methanol (93:7 v/v) as the eluent. Fractions containing the product were pooled and evaporated in vacuo to give the title compound (436 mg, 62%), pure according to TLC, Rf 0.30 (dichloromethane/methanol 90:10 v/v). $^1$H NMR (DMSO-d$_6$; this compound exist as two rotamers; chemical shifts for the minor rotamer is given in brackets): δ 12.14 (s br, 1H, NH), 7.23 (7.19) (d, J=9.9 Hz, 1H, arom), 6.88 (d, J=9.9 Hz, 1H, arom), 6.71 (m, 1H, NH), 4.94 (4.78) (s, 2H, CH$_2$), 4.08 (q, J=7.1 Hz, 2H, CH$_2$), 4.01 (s, 2H, CH$_2$), 3.12 (m, 2H, CH$_2$), 3.02 (m, 2H, CH$_2$), 1.36 (s, 9H, CH$_3$ (Boc)), 1.17 (t, J=7.1 Hz, 3H, CH$_3$). $^{13}$C-NMR (DMSO-d$_6$): δ 169.15 (169.54), 167.15 (167.43), 159.72, 155.79, 151.85, 133.23, 127.57, 78.15 (77.87), 63.04 (63.55), 60.62 (61.20), 47.59 (48.92), 46.82, 38.31 (37.78), 28.25, 14.11. FAB$^+$ MS: 398.94 (M+H$^+$, calc. for C$_{17}$H$_{26}$N$_4$O$_7$+H$^+$ 399.19).

Example 51

N-(2-Bocaminoethyl)-N-[O-(3-oxo-2,3-dihydropyridazin-6-yl)-2-oxyacetyl]glycine (Formula XII)

Ethyl N-(2-Bocaminoethyl)-N-[O-(3-oxo-2,3-dihydropyridazin-6-yl)-2-oxyacetyl]glycinate (402 mg, 1.01 mmol) was suspended in THF (10 mL) and LiOH (2M, aqueous) (2.50 mL) was added. After 90 min, additional water (10 mL) was added and the THF was removed in vacuo. The pH of the aqueous phase was adjusted to 4.0 by addition of HCl (4M, aqueous). The mixture was left in the cold overnight and the resulting precipitate was filtered off, washed with ice cold water (3×10 mL), and dried in vacuo to yield the title compound (124 mg, 34%) as a white powder. The product was pure according to TLC, Rf 0.33 (butanol/acetic acid/water 4:1:1 v/v/v). $^1$H NMR (DMSO-$d_6$; this compound exist as two rotamers; chemical shifts for the minor rotamer is given in brackets): δ 12.14 (s br, 1H, NH), 7.23 (7.17) (d, J=9.9 Hz, 1H, arom), 6.88 (d, J=9.9 Hz, 1H, arom), 6.72 (m, 1H, NH), 4.92 (4.77) (s, 2H, CH$_2$), 3.94 (4.13) (s, 2H, CH$_2$), 3.13 (m, 2H, CH$_2$), 3.02 (m, 2H, CH$_2$), 1.36 (s, 9H, CH$_3$ (Boc)). $^{13}$C NMR (DMSO-$d_6$): δ 170.65 (171.04), 167.02 (167.41), 159.76, 155.84 (155.72), 151.94, 133.24, 127.64, 78.19 (77.91), 63.14 (63.53), 47.39 (48.93), 46.75, 38.28 (37.77), 28.28. FAB$^-$ MS: 369.15 (M+H$^+$, calc. for $C_{15}H_{22}N_4O_7$–H$^+$ 369.14).

Example 52

Ethyl O-[3-oxo-2,3,-Dihydropyridazin-6-yl]4-hydroxybutyrate

To a solution of 3,6-dihydroxypyridazine (20.0 mmol, 2.24 g) in DMF (40 mL) was added NaH (60% dispersion im mineral oil) in one portion. The heterogeneous mixture was stirred at rt for 30 min whereafter ethyl 4-bromobutyrate (25.0 mmol, 4.88 g) was added and the heterogeneous mixture stirred at 100° C. for 2 h. The resulting yellow solution was evaporated in vacuo and taken up into ethylacetate (500 mL) and washed with 5% aqueous NaHCO$_3$ (2×200 mL) and then with brine (200 mL). The organic phase was dried over MgSO$_4$, filtered and evaporated in vacuo. The resulting crude material was recrystallized from ethylacetate/petroleum ether to yield the desired product as a colorless shiny powder (2.35 g, 52%). $^1$H NMR (DMSO-$d_6$): δ 12.14 (s br, 1H, NH), 7.12 (d, J=9.9 Hz, 1H, arom.), 6.86 (d, J=9.9 Hz, 1H, arom), 4.09–4.03 (m, 4H, overlapping CH$_2$), 2.41 (t, J=7.32 Hz, 2H, CH$_2$), 1.94 (m, 2H, CH$_2$), 1.17 (t, J=7.0 Hz, 3H, CH$_3$). $^{13}$C NMR (DMSO-$d_6$): δ 172.55, 159.66, 152.66, 133.16, 127.72, 65.59, 59.97, 30.22, 23.82, 14.18. FAB$^+$ MS: 227.1041 (M+H$^+$, calc. for $C_{15}H_{14}O_4N_2$+H$^+$ 227.1041).

Example 53

O-[3-oxo-2,3,-Dihydropyridazin-6-yl]4-hydroxybutyric Acid

To a solution of Ethyl O-[3-oxo-2,3,-dihydropyridazin-6-yl]4-hydroxybutyrate (5.00 mmol, 1.13 g) in THF (40 mL) was added LiOH (2M, aqueous) (10.0 mL). The solution was stirred at rt. for 15 minutes, additional water (20 mL) was added and the THF was removed in vacuo. The pH of the aqueous phase was adjusted to 3.0 by addition of HCl (2M, aqueous) and the solid material was filtered of and washed with water (2×5 mL). After drying in vacuo the title compound was obtained (909 mg, 91.8%) as a colorless powder.

$^1$H NMR (DMSO-$d_6$): δ 12.14 (s br, 1H, NH), 7.13 (d, J=9.9 Hz, 1H, arom.), 6.86 (d, J=9.9 Hz, 1H, arom), 4.06 (t, J=6.5 Hz, 2H, CH$_2$), 2.34 (t, J=7.4 Hz, 2H, CH$_2$), 1.90 (m, 2H, CH$_2$). $^{13}$C NMR (DMSO-$d_6$): δ 174.15, 159.71, 133.16, 127.78, 65.72, 30.24, 23.87. FAB$^+$ MS: 199.0713 (M+H$^+$, calc. for $C_{15}H_{14}O_4N_2$+H$^+$ 199.0719).

Example 54

Methyl N-(2-Bocaminoethyl)-N-[O-(3-oxo-2,3,-dihydropyridazin-6-yl)4-hydroxybutyryl]glycinate To a solution of O-[3-oxo-2,3,-dihydropyridazin-6-yl]4-hydroxybutyric acid (3.30 mmol, 653 mg) in DMF was added diisopropylethylamine (3.3 mmol, 427 mg) and HBTU (3.30 mmol, 1.25 g) followed by methyl N-(2-Boc-aminoethyl)glycinate (3.0 mmol, 696 mg). The solution was stirred overnight at rt and evaporated in vacuo. The resulting oil was taken up in dichloromethane (200 mL) and washed twice with NaHCO$_3$ (sat, aqueous) (70 mL), then with brine (70 mL) and dried over MgSO$_4$. The solution was filtered and concentrated to dryness in vacuo. The crude product was purified on silica using dichloromethane/methanol (95:5) as the eluent. Fractions containing the product were pooled and evaporated in vacuo to yield the desired product (0.93 g, 75%), as a colorless foam. $^1$H NMR (DMSO-$d_6$; this compound exist as two rotamers; chemical shifts for the minor rotamer is given in brackets): δ 12.12 (s br, 1H, NH), 7.14 (7.11) (d, J=9.9 Hz, 1H, arom.), 6.86 (d, J=9.9 Hz, 1H, arom), 4.05 (t, J=6.4 Hz, 2H, CH$_2$), 3.99 (4.21) (s, 2H, CH$_2$), 3.61 (3.67) (s, 2H, CH$_2$), 3.06 (m, 2H, CH$_2$), 1.91 (m, 2H, CH$_2$), 1.35 (s, 9H, Boc). $^{13}$C NMR (DMSO-$d_6$): δ 172.33 (172.16), 170.43 (170.11), 15963, 155.74, 152.72, 133.07, 127.75, 77.97 (77.73), 65.88, 51.74 (52.20), 47.71, 47.43, 38.34 (37.96), 28.24, 24.12. FAB$^+$ MS: 413.2042 (M+H$^+$, calc. for $C_{18}H_{28}N_4O_7$+H$^+$ 413.2036).

Example 55

N-(2-Bocaminoethyl)-N-[O-(3-oxo-2,3,-dihydropyridazin-6-yl)4-hydroxybutyryl]-glycine (Formula XIII)

The title compound is prepared as per the procedures illustrated in Example 51 using the title compound prepared in Example 54.

It is intended that each of the patents, applications, and printed publications mentioned or referred to in this specification be herein incorporated by reference in their entirety.

As those skilled in the art will appreciate, numerous changes and modifications may be made to the preferred embodiments of the invention without departing from the spirit of the invention. It is intended that all such variations fall within the scope of the invention.

What is claimed is:

1. A compound for binding Watson-Crick base pairs in a double helix having the formula:

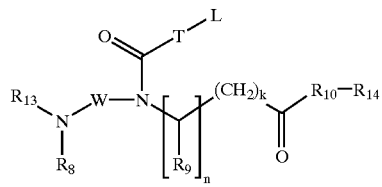

wherein:

$R_8$ is H, $COCH_3$ or an amino protecting group;

$R_9$ is hydrogen or a side chain of a naturally occurring amino acid;

$R_{10}$ is O, NH, O-alkylene or a lysine residue;

W is $-(CH_2)_m-$ where m is from 0 to 6, or

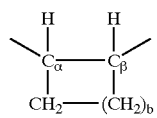

where b is an integer from 0 to 4;
k is from 0 to 5;
n is 0 or 1;
L has the formula

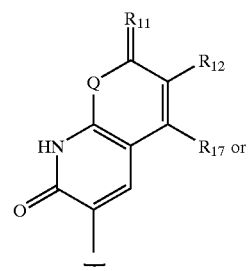

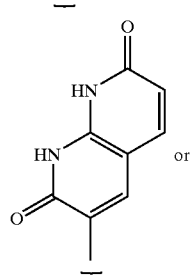

-continued

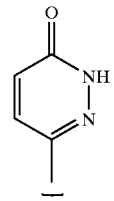

Q is CH or N;

$R_{17}$ is H or $C_1-C_8$ alkyl;

each $R_{11}$ and $R_{12}$ is, independently, H, $C_1-C_8$ alkyl, or halogen;

or $R_{11}$ and $R_{12}$ together with the carbon atoms to which they are attached form a phenyl group;

T has the formula:

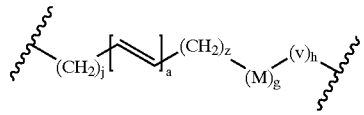

j and z are each, independently, from 0 to 5 with the sum of j and z being from 1 to 7;

M is C(=O), $S(O)_2$, phenyl or $P(O)_2$;

V is NH, S, or $CH_2$;

a, h and g are each, independently, 0 or 1; and $R_{13}$ and $R_{14}$ are each independently H or a nitrogen or oxygen protecting group.

2. The compound of claim 1 wherein L has the formula:

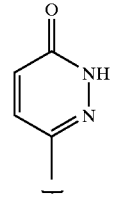

3. The compound of claim 1 wherein L has the formula:

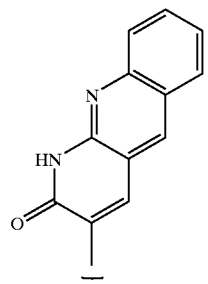

4. The compound of claim 1 wherein L has the formula:

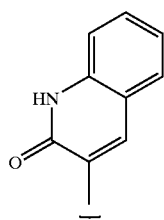

5. The compound of claim 1 wherein L has the formula:

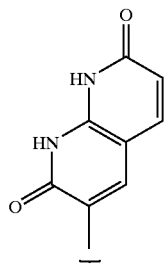

6. The compound of claim 1 wherein L has the formula:

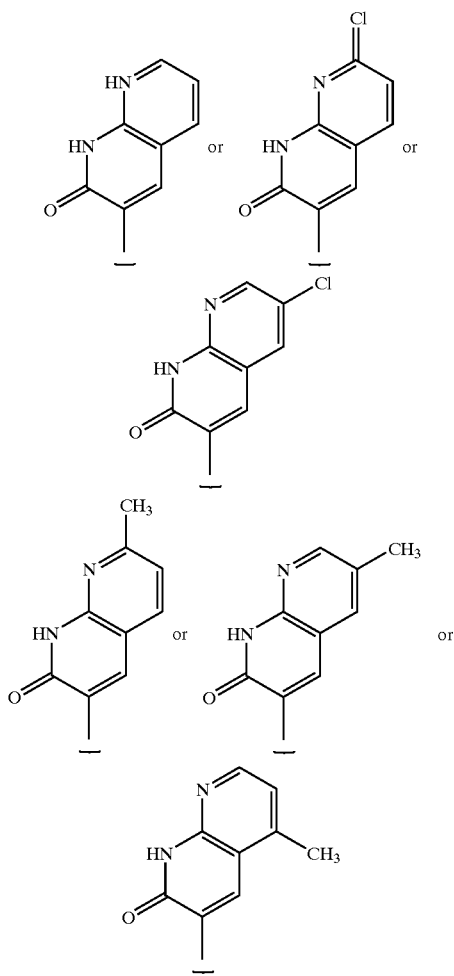

7. The compound of claim 1 wherein g and h are each 0.
8. The compound of claim 7 wherein a is 0.

9. The compound of claim 1 wherein a is 0, g is 0, X is NH and h is 1.
10. The compound of claim 1 wherein b is 2 or 3.
11. The compound of claim 10 wherein at least one of $C\alpha$ or $C\beta$ is in the S configuration.
12. The compound of claim 1 wherein T has the formula —$CH_2$—$CH_2$—NH—.
13. The compound of claim 1 wherein T has the formula —$CH_2$—.
14. The compound of claim 1 wherein T has the formula —$CH_2$—$CH_2$—.
15. The compound of claim 1 wherein T has the formula —O—$CH_2$—$CH_2$—.
16. The compound of claim 1 wherein T has the formula —O—$CH_2$—$CH_2$—$CH_2$—.
17. A compound consisting of a plurality of peptide nucleic acid oligomers linked by linking groups, wherein at least one of said peptide nucleic acid oligomers comprises a moiety having the formula:

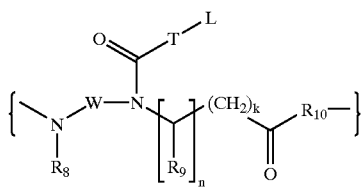

wherein:

$R_8$ is H, $COCH_3$ or an amino protecting group;

$R_9$ is hydrogen or a side chain of a naturally occurring amino acid;

$R_{10}$ is O, NH, O-alkylene or a lysine residue;

W is —$(CH_2)_m$— where m is from 0 to 6, or

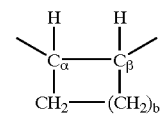

where b is an integer from 0 to 4;

k is from 0 to 5;

n is 0 or 1;

L has the formula

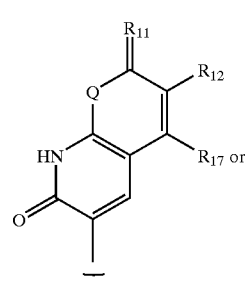

-continued

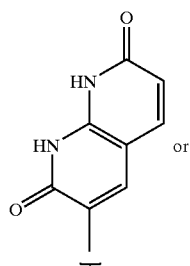
or

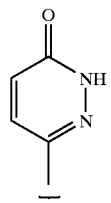

Q is CH or N;

$R_{17}$ is H or $C_1$–$C_8$ alkyl;

each $R_{11}$ and $R_{12}$ is, independently, H, $C_1$–$C_8$ alkyl, or halogen;

or $R_{11}$ and $R_{12}$ together with the carbon atoms to which they are attached form a phenyl group;

T has the formula:

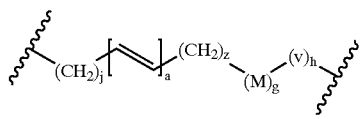

j and z are each, independently, from 0 to 5 with the sum of j and z being from 1 to 7;

M is C(=O), S(O)$_2$, phenyl or P(O)$_2$;

V is NH, S, or CH$_2$; and a, h and g are each, independently, 0 or 1.

18. The compound of claim 17 wherein two peptide nucleic acid oligomers are linked by a linking group.

19. The compound of claim 17 wherein said linking group comprises one or more 8-amino-3,6-dioxaoctanoic acid groups.

20. A compound for binding Watson-Crick base-pairs in a double helix wherein said compound has the formula:

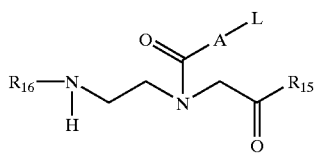

wherein:

L has the formula:

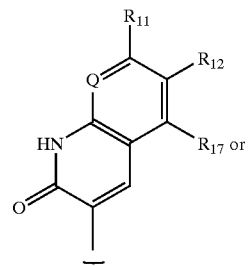

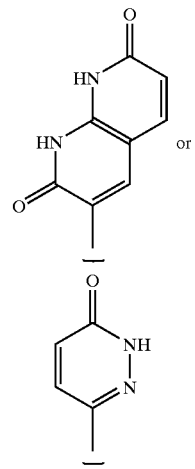

Q is CH or N;

$R_{17}$ is H or $C_1$–$C_8$ alkyl;

each $R_{11}$ and $R_{12}$ is, independently, H, $C_1$–$C_8$ alkyl, or halogen;

or $R_{11}$ and $R_{12}$ together with the carbon atoms to which they are attached form a phenyl group;

A is a single bond, a methylene group or a group of formula:

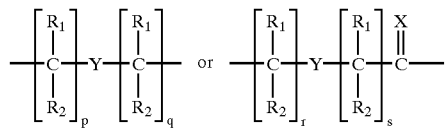

where:

X is O, S, Se, NR$_3$, CH$_2$ or C(CH$_3$)$_2$;

Y is a single bond, O, S or NR$_4$;

each p, q, r and s is, independently, zero or an integer from 1 to 5;

each $R_1$ and $R_2$ is, independently, hydrogen, ($C_1$–$C_4$) alkyl, hydroxy, alkoxy, alkylthio, amino or halogen, wherein said ($C_1$–$C_4$)alkyl is optionally substituted with hydroxy, alkoxy, or alkylthio;

each $R_3$ and $R_4$ is, independently, selected from the group consisting of hydrogen, ($C_1$–$C_4$)alkyl, hydroxy- or alkoxy- or alkylthio-substituted ($C_1$–$C_4$) alkyl, hydroxy, alkoxy, alkylthio and amino;

$R_{15}$ is OH, a protected hydroxyl group, or a protecting group; and $R_{16}$ is H or an amino protecting group.

21. An oligomeric compound for binding Watson-Crick base pairs in a double helix wherein said compound comprises at least one monomeric unit having the formula:

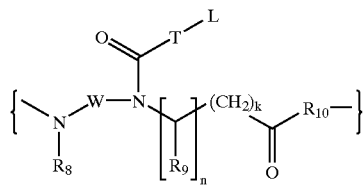

wherein:
  $R_8$ is H, $COCH_3$ or an amino protecting group;
  $R_9$ is hydrogen or a side chain of a naturally occurring amino acid;
  $R_{10}$ is O, NH, O-alkylene or a lysine residue;
  W is $—(CH_2)_m—$ where m is from 0 to 6, or

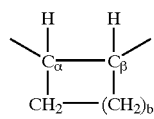

where
  b is an integer from 0 to 4;
  k is from 0 to 5;
  n is 0 or 1;
  L has the formula:

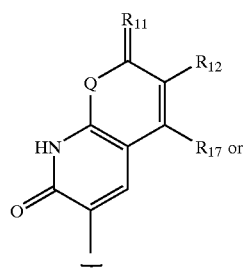

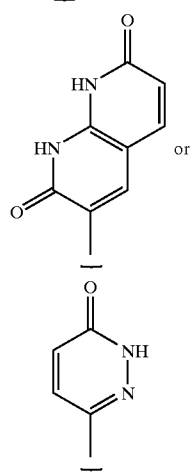

Q is CH or N;
  $R_{17}$ is H or $C_1$–$C_8$ alkyl;
  each $R_{11}$ and $R_{12}$ is, independently, H, $C_1$–$C_8$ alkyl, or halogen;
  or $R_{11}$ and $R_{12}$ together with the carbon atoms to which they are attached form a phenyl group;

T has the formula:

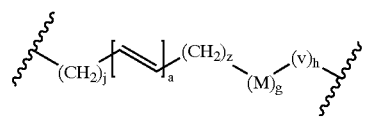

j and z are each, independently, from 0 to 5 with the sum of j and z being from 1 to 7;
  M is C(=O), $S(O)_2$, phenyl or $P(O)_2$;
  V is NH, S, or $CH_2$; and
  a, h and g are each, independently, 0 or 1.

22. The compound of claim 21 wherein L has the formula:

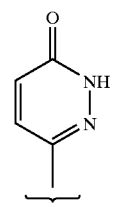

23. The compound of claim 21 wherein L has the formula:

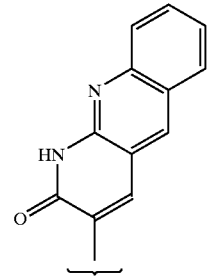

24. The compound of claim 21 wherein L has the formula:

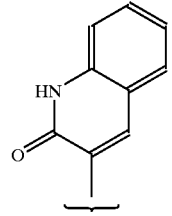

25. The compound of claim 21 wherein L has the formula:

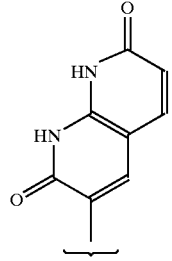

26. The compound of claim 21 wherein L has the formula:

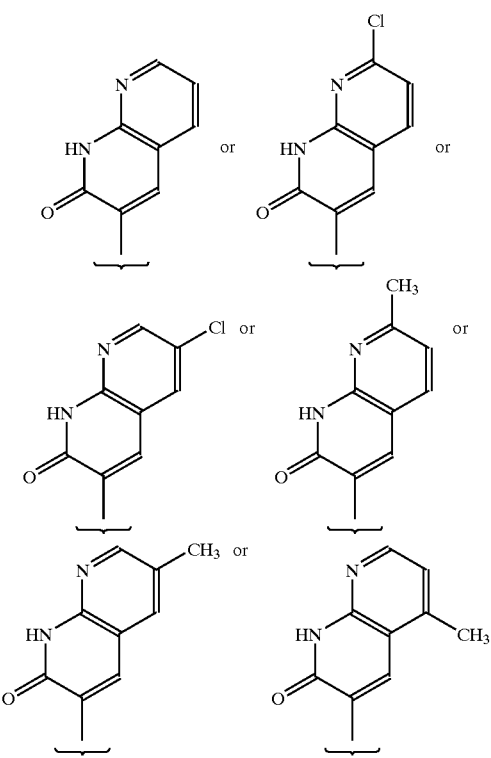

27. The compound of claim 21 wherein g and h are each 0.

28. The compound of claim 27 wherein a is 0.

29. The compound of claim 21 wherein a is 0, g is 0, V is NH and h is 1.

30. The compound of claim 21 wherein b is 2 or 3.

31. The compound of claim 30 wherein at least one of Cα or Cβ is in the S configuration.

32. The compound of claim 21 wherein T has the formula —CH$_2$—CH$_2$—NH—.

33. The compound of claim 21 wherein T has the formula —CH$_2$—.

34. The compound of claim 21 wherein T has the formula —CH$_2$—CH.

35. The compound of claim 21 wherein T has the formula —O—CH—CH$_2$—.

36. The compound of claim 21 wherein T has the formula —O—CH$_2$—CH$_2$—CH$_2$—.

37. The compound of claim 21 wherein W is —(CH$_2$)$_m$—.

38. The compound of claim 37 wherein m is 2.

39. The compound of claim 21 wherein W has the formula:

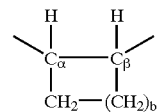

40. The compound of claim 39 wherein b is 2.

41. The compound of claim 39 wherein b is 3.

42. The compound of claim 21 having SEQ ID NO: 44.

* * * * *

UNITED STATES PATENT AND TRADEMARK OFFICE
CERTIFICATE OF CORRECTION

PATENT NO. : 6,632,919 B1 Page 1 of 10
DATED : October 14, 2003
INVENTOR(S) : Peter E. Nielsen, Gerald Haaima and Anne B. Eldrup It is certified that error appears in the above-identified patent and that said Letters Patent is hereby corrected as shown below:

Column 95, lines 11 thru 65 and Column 96, lines 11 thru 42,
Delete "A compound for binding Watson-Crick base pairs in a double helix having the formula:

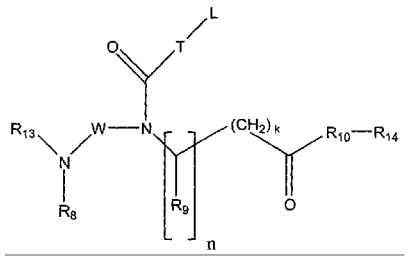

wherein
    $R_8$ is H, $COCH_3$ or an amino protecting group;
    $R_9$ is hydrogen or a side chain of a naturally occurring amino acid;
    $R_{10}$ is O, NH, O-alkylene or a lysine residue;
    W is $-(CH_2)_m-$ where m is from 0 to 6, or

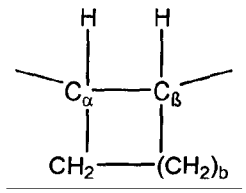

where b is an integer from 0 to 4;
    k is from 0 to 5;
    n is 0 or 1;
    L has the formula

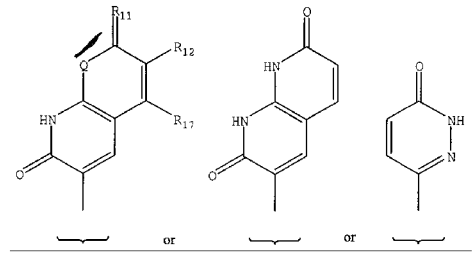

Q is CH or N;
    $R_{17}$ is H or C1-C8 alkyl;
    each $R_{11}$ and $R_{12}$ is, independently, H, C1-C8 alkyl, or halogen;
    or $R_{11}$ and $R_{12}$ together with the carbon atoms to which they are attached form a phenyl group;

UNITED STATES PATENT AND TRADEMARK OFFICE
CERTIFICATE OF CORRECTION

PATENT NO.   : 6,632,919 B1
DATED        : October 14, 2003
INVENTOR(S)  : Peter E. Nielsen, Gerald Haaima and Anne B. Eldrup It is certified that error appears in the above-identified patent and that said Letters Patent is hereby corrected as shown below:

T has the formula:

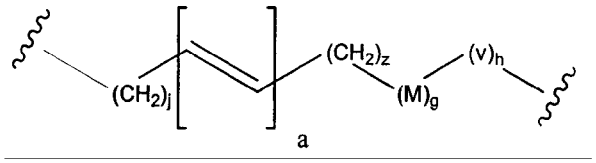

j and z are each, independently, from 0 to 5 with the sum of j and z being from 1 to 7;
M is C(=O), S(O)$_2$, phenyl or P(O)$_2$;
V is NH, S, or CH$_2$;
a, h and g are each, independently, 0 or 1; and
R$_{13}$ and R$_{14}$ are each independently H or a nitrogen or oxygen protecting group."

And insert therefore -- 1.    A compound for binding Watson-Crick base pairs in a double helix having the formula:

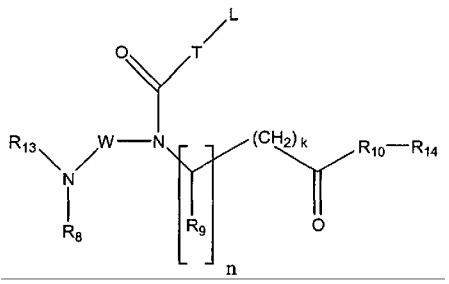

wherein:
R$_8$ is H, COCH$_3$ or an amino protecting group;
R$_9$ is hydrogen or a side chain of naturally occurring amino acid;
R$_{10}$ is O, NH, O-alkylene or a lysine residue;

W is -(CH$_2$)$_m$- where m is from 0 to 6, or

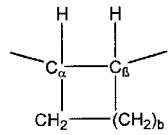

where b is an integer from 0 to 4;
k is from 0 to 5;
n is 0 or 1;
L has the formula

UNITED STATES PATENT AND TRADEMARK OFFICE
CERTIFICATE OF CORRECTION

PATENT NO.   : 6,632,919 B1
DATED        : October 14, 2003
INVENTOR(S)  : Peter E. Nielsen, Gerald Haaima and Anne B. Eldrup It is certified that error appears in the above-identified patent and that said Letters Patent is hereby corrected as shown below:

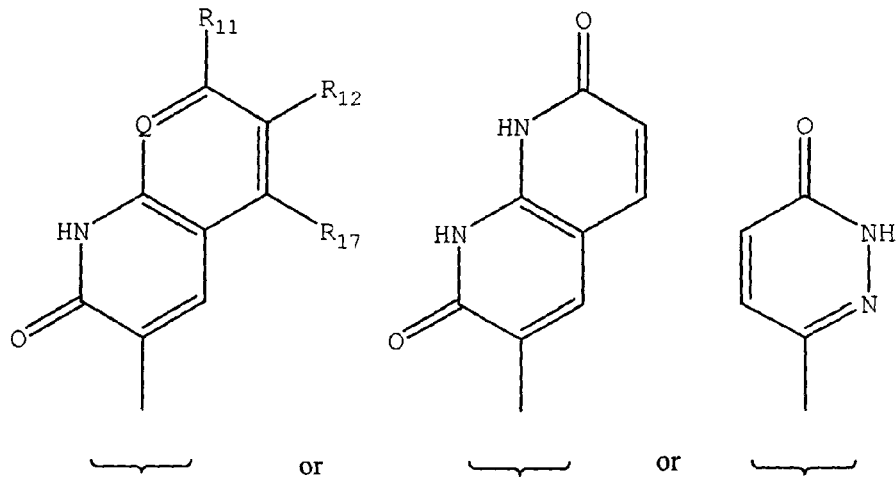

Q is CH or N;
$R_{17}$ is H or $C_1$-$C_8$ alkyl;
each $R_{11}$ and $R_{12}$ is, independently, H, $C_1$-$C_8$ alkyl, or halogen;
or $R_{11}$ and $R_{12}$ together with the carbon atoms to which they are attached form a phenyl group;

T has the formula:

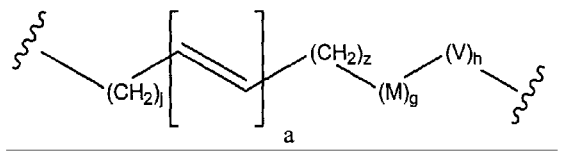

j and z are each, independently, from 0 to 5 with the sum of j and z being from 1 to 7;
M is C(=O), S(O)$_2$, phenyl or P(O)$_2$;
V is NH, S, or CH$_2$;
a, h and g are each, independently, 0 or 1; and
$R_{13}$ and $R_{14}$ are each independently H or a nitrogen or oxygen protecting group --.

UNITED STATES PATENT AND TRADEMARK OFFICE
CERTIFICATE OF CORRECTION

PATENT NO. : 6,632,919 B1
DATED : October 14, 2003
INVENTOR(S) : Peter E. Nielsen, Gerald Haaima and Anne B. Eldrup It is certified that error appears in the above-identified patent and that said Letters Patent is hereby corrected as shown below:

<u>Column 97,</u>
Lines 26 thru 65, delete "The compound of claim 1 wherein L has the formula:

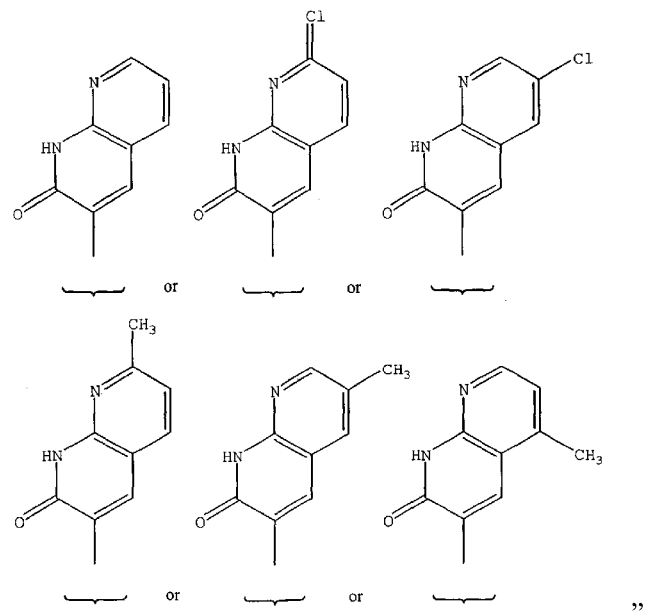

And insert therefore -- 6.   The compound of claim 1 wherein L has the formula:

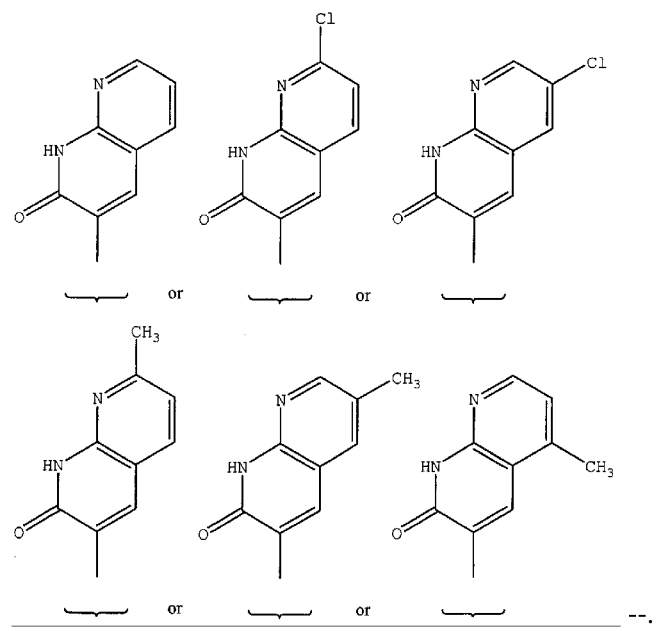

--.

UNITED STATES PATENT AND TRADEMARK OFFICE
CERTIFICATE OF CORRECTION

PATENT NO. : 6,632,919 B1
DATED : October 14, 2003
INVENTOR(S) : Peter E. Nielsen, Gerald Haaima and Anne B. Eldrup It is certified that error appears in the above-identified patent and that said Letters Patent is hereby corrected as shown below:

Column 98,
Line 1, delete "X" and insert therefor -- V --.

Column 98, lines 18 thru 65 and Column 99, lines 1 thru 48,
Delete "A compound consisting of a plurality of peptide nucleic acid oligomers linked by linking groups, wherein at least one of said peptide nucleic acid oligomers comprises a moiety having the formula:

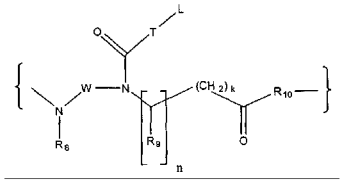

wherein:
  $R_8$ is H, $COCH_3$ or an amino protecting group;
  $R_9$ is hydrogen or a side chain of a naturally occurring amino acid;
  $R_{10}$ is O, NH, O-alkylene or a lysine residue;
  W is $-(CH2)_m-$ where m is from 0 to 6, or

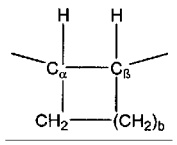

where b is an integer from 0 to 4;
  k is from 0 to 5;
  n is 0 or 1;
  L has the formula

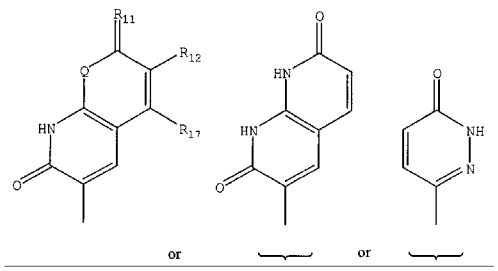

Q is CH or N;
  $R_{17}$ is H or $C_1$-$C_8$ alkyl;
  each $R_{11}$ and $R_{12}$ is, independently, H, $C_1$-$C_8$ alkyl, or halogen;
  or $R_{11}$ and $R_{12}$ together with the carbon atoms to which they are attached form a phenyl group;

UNITED STATES PATENT AND TRADEMARK OFFICE
CERTIFICATE OF CORRECTION

PATENT NO. : 6,632,919 B1
DATED : October 14, 2003
INVENTOR(S) : Peter E. Nielsen, Gerald Haaima and Anne B. Eldrup It is certified that error appears in the above-identified patent and that said Letters Patent is hereby corrected as shown below:

T has the formula:

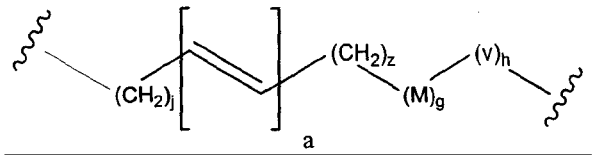

j and z are each, independently, from 0 to 5 with the sum of j and z being from 1 to 7;
M is C(=O), S(O)$_2$, phenyl or P(O)$_2$;
V is NH, S, or CH$_2$; and
a, h and g are each, independently, 0 or 1."

And insert therefor -- 17. A compound consisting of a plurality of peptide nucleic acid oligomers linked by linking groups, wherein at least one of said peptide nucleic acid oligomers comprises a moiety having the formula:

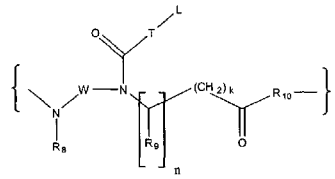

wherein:
$R_8$ is H, COCH$_3$ or an amino protecting group;
$R_9$ is hydrogen or a side chain of a naturally occurring amino acid;
$R_{10}$ is O, NH, O-alkylene or a lysine residue;
W is -( CH$_2$ ) $_m$- where m is from 0 to 6, or

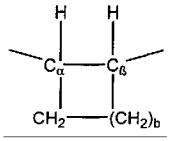

where b is an integer from 0 to 4;
k is from 0 to 5;
n is 0 or 1;
L has the formula

UNITED STATES PATENT AND TRADEMARK OFFICE
CERTIFICATE OF CORRECTION

PATENT NO. : 6,632,919 B1
DATED : October 14, 2003
INVENTOR(S) : Peter E. Nielsen, Gerald Haaima and Anne B. Eldrup It is certified that error appears in the above-identified patent and that said Letters Patent is hereby corrected as shown below:

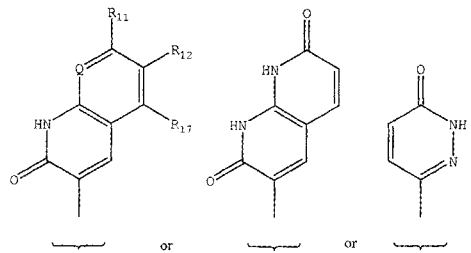

Q is CH or N;
$R_{17}$ is H or $C_1$-$C_8$ alkyl;
each $R_{11}$ and $R_{12}$ is, independently, H, $C_1$-$C_8$ alkyl, or halogen;
or $R_{11}$ and $R_{12}$ together with the carbon atoms to which they are attached form a phenyl group;

T has the formula:

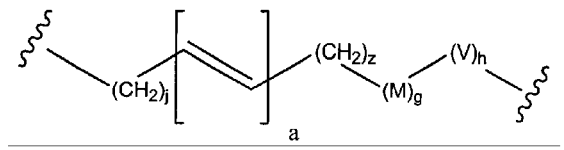

j and z are each, independently, from 0 to 5 with the sum of j and z being from 1 to 7;
M is C(=O), S(O)$_2$, phenyl or P(O)$_2$;
V is NH, S, or CH$_2$; and
a, h and g are each, independently, 0 or 1 --.

UNITED STATES PATENT AND TRADEMARK OFFICE
CERTIFICATE OF CORRECTION

PATENT NO. : 6,632,919 B1
DATED : October 14, 2003
INVENTOR(S) : Peter E. Nielsen, Gerald Haaima and Anne B. Eldrup It is certified that error appears in the above-identified patent and that said Letters Patent is hereby corrected as shown below:

Column 101, lines 1 thru 65 and Column 102, lines 1 thru 14,
Delete "An oligomeric compound for binding Watson-Crick base pairs in a double helix wherein said compound comprises at least one monomeric unit having the fomula:

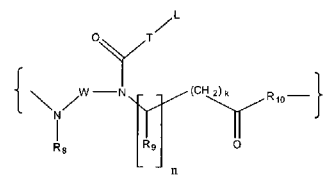

wherein:
$R_8$ is H, $COCH_3$ or an amino protecting group;
$R_9$ is hydrogen or a side chain of a naturally occurring amino acid;
$R_{10}$ is O, NH, O-alkylene or a lysine residue;
W is $-(CH_2)_m-$ where m is from 0 to 6, or

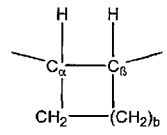

where b is an integer from 0 to 4;
k is from 0 to 5;
n is 0 or 1;
L has the formula

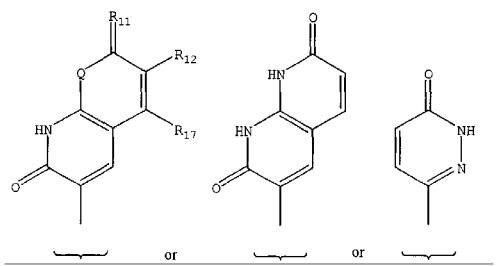

Q is CH or N;
$R_{17}$ is H or $C_1$-$C_8$ alkyl;
each $R_{11}$ and $R_{12}$ is, independently, H, $C_1$-$C_8$ alkyl, or halogen;
or $R_{11}$ and $R_{12}$ together with the carbon atoms to which they are attached form a phenyl group;

UNITED STATES PATENT AND TRADEMARK OFFICE
CERTIFICATE OF CORRECTION

PATENT NO. : 6,632,919 B1
DATED : October 14, 2003
INVENTOR(S) : Peter E. Nielsen, Gerald Haaima and Anne B. Eldrup It is certified that error appears in the above-identified patent and that said Letters Patent is hereby corrected as shown below:

T has the formula:

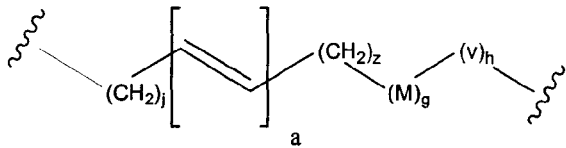

j and z are each, independently, from 0 to 5 with the sum of j and z being from 1 to 7;
M is $C(=O)$, $S(O)_2$, phenyl or $P(O)_2$;
V is NH, S, or $CH_2$; and
a, h and g are each, independently, 0 or 1."

And insert therefor -- 21. An oligomeric compound for binding Watson-Crick base pairs in a double helix wherein said compound comprises at least one monomeric unit having the fomula:

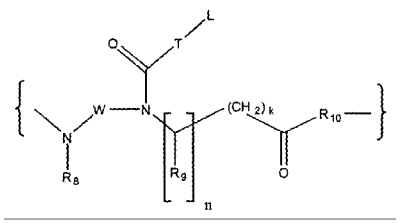

wherein:
$R_8$ is H, $COCH_3$ or an amino protecting group;
$R_9$ is hydrogen or a side chain of a naturally occurring amino acid;
$R_{10}$ is O, NH, O-alkylene or a lysine residue;
W is $-(CH_2)_m-$ where m is from 0 to 6, or

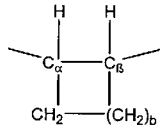

where b is an integer from 0 to 4;
k is from 0 to 5;
n is 0 or 1;
L has the formula:

UNITED STATES PATENT AND TRADEMARK OFFICE
CERTIFICATE OF CORRECTION

PATENT NO. : 6,632,919 B1
DATED : October 14, 2003
INVENTOR(S) : Peter E. Nielsen, Gerald Haaima and Anne B. Eldrup It is certified that error appears in the above-identified patent and that said Letters Patent is hereby corrected as shown below:

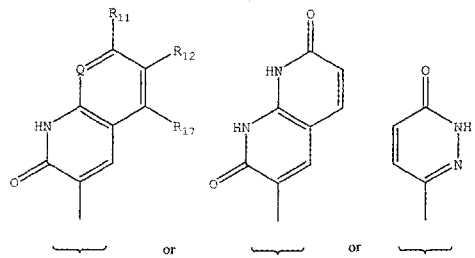

Q is CH or N;
$R_{17}$ is H or $C_1$-$C_8$ alkyl;
each $R_{11}$ and $R_{12}$ is, independently, H, $C_1$-$C_8$ alkyl, or halogen;
or $R_{11}$ and $R_{12}$ together with the carbon atoms to which they are attached form a phenyl group;

T has the formula:

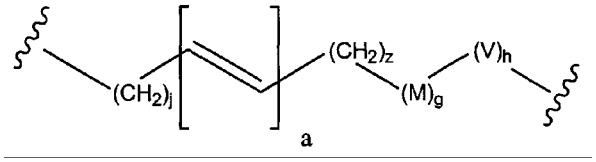

j and z are each, independently, from 0 to 5 with the sum of j and z being from 1 to 7;
M is C(=O), S(O)$_2$, phenyl or P(O)$_2$;
V is NH, S, or CH$_2$; and
a, h and g are each, independently, 0 or 1 --.

Signed and Sealed this

Twenty-third Day of March, 2004

JON W. DUDAS
*Acting Director of the United States Patent and Trademark Office*